US008187325B2

(12) United States Patent
Zadno-Azizi et al.

(10) Patent No.: US 8,187,325 B2
(45) Date of Patent: *May 29, 2012

(54) MATERIALS FOR USE IN ACCOMMODATING INTRAOCULAR LENS SYSTEM

(75) Inventors: Gholam-Reza Zadno-Azizi, Fremont, CA (US); Tuan Anh Nguyen, Orange, CA (US)

(73) Assignee: Visiogen, Inc., Santa Ana, CA (US)

( * ) Notice: Subject to any disclaimer, the term of this patent is extended or adjusted under 35 U.S.C. 154(b) by 1225 days.

This patent is subject to a terminal disclaimer.

(21) Appl. No.: 11/406,821

(22) Filed: Apr. 19, 2006

(65) Prior Publication Data

US 2006/0271187 A1 Nov. 30, 2006

Related U.S. Application Data

(63) Continuation of application No. 10/207,717, filed on Jul. 25, 2002, now abandoned, which is a continuation-in-part of application No. 10/020,853, filed on Dec. 11, 2001, now Pat. No. 7,118,596.

(60) Provisional application No. 60/337,343, filed on Nov. 9, 2001, provisional application No. 60/283,856, filed on Apr. 13, 2001, provisional application No. 60/264,179, filed on Jan. 25, 2001, provisional application No. 60/337,343, filed on Nov. 9, 2001.

(51) Int. Cl.
*A61F 2/16* (2006.01)

(52) U.S. Cl. ...................................... 623/6.34; 623/6.37

(58) Field of Classification Search .................. 623/6.34
See application file for complete search history.

(56) References Cited

U.S. PATENT DOCUMENTS

| 1,483,509 | A | 2/1924 | Bugbee |
| 2,129,305 | A | 9/1938 | Feinbloom |
| 2,274,142 | A | 2/1942 | Houchin |
| 2,405,989 | A | 8/1946 | Beach |
| 2,511,517 | A | 6/1950 | Spiegel |
| 3,031,927 | A | 5/1962 | Wesley |
| 3,034,403 | A | 5/1962 | Neefe |
| RE25,286 | E | 11/1962 | de Carte |

(Continued)

FOREIGN PATENT DOCUMENTS

AU 3225789 10/1989

(Continued)

OTHER PUBLICATIONS

Tsutomu Hara et al., "Accommodative Intraocular Lens with Spring Action Part 1. Design and Placement in an Excised Animal Eye," Opthalmic Surgery, Feb. 1990, vol. 21, No. 2, pp. 128-133.

(Continued)

*Primary Examiner* — David H. Willse
(74) *Attorney, Agent, or Firm* — Visiogen, Inc.

(57) ABSTRACT

There is disclosed an accommodating intraocular lens for implantation in an eye having an optical axis. The lens comprises an anterior portion which in turn comprises an anterior viewing element and an anterior biasing element. The lens further comprises a posterior portion which in turn comprises a posterior viewing element in spaced relationship to the anterior viewing element and a posterior biasing element. The anterior portion and posterior portion meet at first and second apices of the intraocular lens. The anterior portion and the posterior portion and/or the apices are responsive to force thereon to cause the separation between the viewing elements to change. Additional embodiments and methods are also disclosed.

21 Claims, 66 Drawing Sheets

U.S. PATENT DOCUMENTS

| | | |
|---|---|---|
| 3,210,894 A | 10/1965 | Bentley et al. |
| 3,222,432 A | 12/1965 | Grandperret |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaltre |
| 3,760,045 A | 9/1973 | Thiele et al. |
| 3,922,728 A | 12/1975 | Krasnov |
| 3,932,148 A | 1/1976 | Krewalk, Sr. |
| 4,055,378 A | 10/1977 | Feneberg |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,163 A | 12/1980 | Galin |
| 4,240,719 A | 12/1980 | Gullino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,426,741 A | 1/1984 | Bittner |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshort |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,655,770 A | 4/1987 | Gupta et al. |
| 4,666,445 A | 5/1987 | Tillay |
| 4,676,792 A | 6/1987 | Praeger |
| 4,681,102 A | 7/1987 | Bartell |
| 4,687,484 A | 8/1987 | Kaplan |
| 4,693,572 A | 9/1987 | Tsuetaki et al. |
| RE32,525 E | 10/1987 | Pannu |
| 4,702,244 A | 10/1987 | Mazzocco |
| 4,704,016 A | 11/1987 | de Carle |
| 4,720,286 A | 1/1988 | Bailey et al. |
| 4,725,278 A | 2/1988 | Shearing |
| 4,731,078 A | 3/1988 | Stoy et al. |
| 4,752,123 A | 6/1988 | Blaker |
| 4,759,762 A | 7/1988 | Grendahl |
| 4,769,033 A | 9/1988 | Nordan |
| 4,780,154 A | 10/1988 | Mori et al. |
| 4,790,847 A | 12/1988 | Woods |
| 4,813,955 A | 3/1989 | Achatz et al. |
| 4,830,481 A | 5/1989 | Futhey et al. |
| 4,834,094 A | 5/1989 | Patton et al. |
| 4,842,601 A | 6/1989 | Smith |
| 4,862,885 A | 9/1989 | Cumming |
| 4,881,804 A | 11/1989 | Cohen |
| 4,883,485 A | 11/1989 | Patel |
| 4,888,012 A | 12/1989 | Horn et al. |
| 4,888,015 A | 12/1989 | Domino |
| 4,890,912 A | 1/1990 | Visser |
| 4,890,913 A | 1/1990 | de Carle |
| 4,892,543 A | 1/1990 | Turley |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,130 A | 4/1990 | Stoy et al. |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,082 A | 2/1991 | Richards et al. |
| 4,994,083 A | 2/1991 | Sule et al. |
| 5,000,559 A | 3/1991 | Takahashi et al. |
| 5,002,382 A | 3/1991 | Seidner |
| 5,002,979 A | 3/1991 | Stoyan |
| 5,019,098 A | 5/1991 | Mercier |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,098,439 A | 3/1992 | Hill et al. |
| 5,112,351 A | 5/1992 | Christie et al. |
| 5,123,905 A | 6/1992 | Kelman |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,712 A | 11/1992 | Portney |
| 5,171,266 A | 12/1992 | Wiley et al. |
| 5,171,319 A | 12/1992 | Keates et al. |
| 5,171,320 A | 12/1992 | Nishi |
| 5,173,723 A | 12/1992 | Volk |
| 5,190,552 A | 3/1993 | Kelman |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,275,604 A | 1/1994 | Rheinish et al. |
| 5,275,623 A | 1/1994 | Sarfarazi |
| 5,326,347 A | 7/1994 | Cumming |
| 5,354,335 A | 10/1994 | Lipshitz et al. |
| 5,358,520 A | 10/1994 | Patel |
| 5,391,202 A | 2/1995 | Lipshitz et al. |
| 5,425,734 A | 6/1995 | Blake |
| RE34,998 E | 7/1995 | Langerman |
| 5,443,506 A | 8/1995 | Garabet |
| 5,468,246 A | 11/1995 | Blake |
| 5,474,562 A | 12/1995 | Orchowski |
| 5,476,514 A | 12/1995 | Cumming |
| 5,480,428 A | 1/1996 | Fedorov et al. |
| 5,489,302 A | 2/1996 | Skottun |
| 5,494,484 A | 2/1996 | Feingold |
| 5,496,328 A | 3/1996 | Nakajima et al. |
| 5,499,987 A | 3/1996 | Feingold |
| 5,503,165 A | 4/1996 | Schachar |
| 5,507,806 A | 4/1996 | Blake |
| 5,522,891 A | 6/1996 | Klaas |
| 5,549,760 A | 8/1996 | Becker |
| 5,562,731 A | 10/1996 | Cumming |
| 5,578,081 A | 11/1996 | McDonald |
| 5,582,614 A | 12/1996 | Feingold |
| 5,607,472 A | 3/1997 | Thompson |
| 5,616,148 A | 4/1997 | Eagles et al. |
| 5,620,450 A | 4/1997 | Eagles et al. |
| 5,620,720 A | 4/1997 | Glick et al. |
| 5,628,795 A | 5/1997 | Langerman |
| 5,628,796 A | 5/1997 | Suzuki |
| 5,652,014 A | 7/1997 | Galin et al. |

| Patent No. | Date | Inventor |
|---|---|---|
| 5,652,638 A | 7/1997 | Roffman et al. |
| 5,653,754 A | 8/1997 | Nakajima et al. |
| 5,682,223 A | 10/1997 | Menezes et al. |
| 5,684,560 A | 11/1997 | Roffman et al. |
| 5,725,576 A | 3/1998 | Fedorov et al. |
| 5,728,102 A | 3/1998 | Feingold |
| 5,766,244 A | 6/1998 | Binder |
| 5,769,890 A | 6/1998 | McDonald |
| 5,776,191 A | 7/1998 | Mazzocco |
| 5,776,192 A | 7/1998 | McDonald |
| 5,800,442 A | 9/1998 | Wolf et al. |
| 5,800,533 A | 9/1998 | Eggleston et al. |
| 5,807,400 A | 9/1998 | Chambers et al. |
| 5,814,103 A | 9/1998 | Lipshitz et al. |
| 5,824,074 A | 10/1998 | Koch |
| 5,843,188 A | 12/1998 | McDonald |
| 5,860,984 A | 1/1999 | Chambers et al. |
| 5,873,879 A | 2/1999 | Figueroa et al. |
| 5,876,440 A | 3/1999 | Feingold |
| 5,876,442 A | 3/1999 | Lipshitz et al. |
| 5,921,989 A | 7/1999 | Deacon et al. |
| 5,928,245 A | 7/1999 | Wolf et al. |
| 5,928,283 A | 7/1999 | Gross et al. |
| 5,941,886 A | 8/1999 | Feingold |
| 5,944,725 A | 8/1999 | Cicenas et al. |
| 5,947,975 A | 9/1999 | Kikuchi et al. |
| 5,968,094 A | 10/1999 | Werblin et al. |
| 5,984,962 A | 11/1999 | Anello et al. |
| 6,013,101 A | 1/2000 | Israel |
| 6,106,554 A | 8/2000 | Bretton |
| 6,113,633 A | 9/2000 | Portney |
| 6,117,171 A | 9/2000 | Skottun |
| 6,120,538 A | 9/2000 | Rizzo et al. |
| 6,129,733 A | 10/2000 | Brady et al. |
| 6,136,026 A | 10/2000 | Israel |
| 6,162,229 A | 12/2000 | Feingold et al. |
| 6,176,878 B1 | 1/2001 | Gwon et al. |
| 6,197,058 B1 | 3/2001 | Portney |
| 6,197,059 B1 | 3/2001 | Cumming |
| 6,200,342 B1 | 3/2001 | Tassignon |
| 6,217,612 B1 | 4/2001 | Woods |
| 6,228,094 B1 | 5/2001 | Erdman |
| 6,231,603 B1 | 5/2001 | Lang et al. |
| 6,238,433 B1 | 5/2001 | Portney |
| 6,258,123 B1 | 7/2001 | Young et al. |
| 6,277,146 B1 | 8/2001 | Peyman et al. |
| 6,280,471 B1 | 8/2001 | Peyman et al. |
| RE37,387 E | 9/2001 | Brady et al. |
| 6,299,641 B1 | 10/2001 | Woods |
| 6,327,772 B1 | 12/2001 | Zadno-Azizi et al. |
| 6,334,862 B1 | 1/2002 | Vidal et al. |
| 6,342,073 B1 | 1/2002 | Cumming et al. |
| 6,358,280 B1 | 3/2002 | Herrick |
| 6,387,126 B1 | 5/2002 | Cumming |
| 6,406,494 B1 | 6/2002 | Laguette et al. |
| 6,423,094 B1 | 7/2002 | Sarfarazi |
| 6,443,985 B1 | 9/2002 | Woods |
| 6,450,642 B1 | 9/2002 | Jethmalani et al. |
| 6,454,802 B1 | 9/2002 | Bretton et al. |
| 6,464,725 B2 | 10/2002 | Skottun |
| 6,468,282 B2 | 10/2002 | Kikuchi et al. |
| 6,478,821 B1 | 11/2002 | Laguette et al. |
| 6,488,708 B2 | 12/2002 | Sarfarazi |
| 6,503,275 B1 | 1/2003 | Cumming |
| 6,524,340 B2 | 2/2003 | Israel |
| 6,524,350 B2 | 2/2003 | Buentello et al. |
| 6,533,813 B1 | 3/2003 | Lin et al. |
| 6,547,822 B1 | 4/2003 | Lang |
| 6,551,354 B1 | 4/2003 | Ghazizadeh et al. |
| 6,554,859 B1 | 4/2003 | Lang et al. |
| 6,558,420 B2 | 5/2003 | Green |
| 6,599,317 B1 | 7/2003 | Weinschenk, III et al. |
| 6,616,691 B1 | 9/2003 | Tran |
| 6,616,692 B1 | 9/2003 | Glick et al. |
| 6,645,246 B1 | 11/2003 | Weinschenk et al. |
| 6,660,035 B1 | 12/2003 | Lang et al. |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,934 B2 | 9/2004 | Zadno-Azizi et al. |
| 6,818,017 B1 | 11/2004 | Shu |
| 6,818,158 B2 | 11/2004 | Pham et al. |
| 6,846,326 B2 | 1/2005 | Zadno-Azizi et al. |
| 6,858,040 B2 | 2/2005 | Nguyen et al. |
| 6,884,261 B2 | 4/2005 | Zadno-Azizi et al. |
| 6,884,263 B2 | 4/2005 | Valyunin et al. |
| 6,899,732 B2 | 5/2005 | Zadno-Azizi et al. |
| 6,926,736 B2 | 8/2005 | Peng et al. |
| 7,041,134 B2 | 5/2006 | Nguyen et al. |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,125,422 B2 | 10/2006 | Woods et al. |
| 7,198,640 B2 | 4/2007 | Nguyen |
| 7,226,478 B2 | 6/2007 | Ting et al. |
| 7,238,201 B2 | 7/2007 | Portney et al. |
| 7,662,180 B2 | 2/2010 | Paul et al. |
| 2001/0020171 A1 | 9/2001 | Heyman et al. |
| 2002/0002404 A1 | 1/2002 | Sarfarazi |
| 2002/0004682 A1 | 1/2002 | Zhou et al. |
| 2002/0045937 A1 | 4/2002 | Sarfarazi |
| 2002/0072795 A1 | 6/2002 | Green |
| 2002/0077633 A1 | 6/2002 | Kikuchi et al. |
| 2002/0082609 A1 | 6/2002 | Green |
| 2002/0095212 A1 | 7/2002 | Boehm |
| 2002/0120329 A1 | 8/2002 | Lang et al. |
| 2002/0138140 A1 | 9/2002 | Hanna |
| 2002/0143395 A1 | 10/2002 | Skottun |
| 2002/0188351 A1 | 12/2002 | Laguette |
| 2003/0002404 A1 | 1/2003 | Maekawa |
| 2003/0018384 A1 | 1/2003 | Valyunin et al. |
| 2003/0033013 A1 | 2/2003 | Callahan et al. |
| 2003/0050695 A1 | 3/2003 | Lin et al. |
| 2003/0050696 A1 | 3/2003 | Cumming |
| 2003/0050697 A1 | 3/2003 | Paul |
| 2003/0060878 A1 | 3/2003 | Shadduck |
| 2003/0060881 A1 | 3/2003 | Glick et al. |
| 2003/0078657 A1 | 4/2003 | Zadno-Azizi et al. |
| 2003/0078658 A1 | 4/2003 | Zadno-Azizi et al. |
| 2003/0083744 A1 | 5/2003 | Khoury |
| 2003/0093149 A1 | 5/2003 | Glazier |
| 2003/0105522 A1 | 6/2003 | Glazier |
| 2003/0114927 A1 | 6/2003 | Nagamoto |
| 2003/0130732 A1 | 7/2003 | Sarfarazi |
| 2003/0187504 A1 | 10/2003 | Weinschenk, III et al. |
| 2003/0204255 A1 | 10/2003 | Peng et al. |
| 2004/0015236 A1 | 1/2004 | Sarfarazi |
| 2004/0020597 A1 | 2/2004 | Hashiguchi |
| 2004/0158322 A1 | 8/2004 | Shen |
| 2004/0160575 A1 | 8/2004 | Ayton et al. |
| 2005/0049700 A1 | 3/2005 | Zadno-Azizi et al. |
| 2005/0165410 A1 | 7/2005 | Zadno-Azizi et al. |
| 2005/0182419 A1 | 8/2005 | Tsai |
| 2005/0228401 A1 | 10/2005 | Zadno-Azizi et al. |
| 2005/0234547 A1 | 10/2005 | Nguyen et al. |
| 2005/0267575 A1 | 12/2005 | Nguyen et al. |
| 2006/0100703 A1 | 5/2006 | Evans et al. |
| 2006/0178741 A1 | 8/2006 | Zadno-Azizi et al. |
| 2006/0184244 A1 | 8/2006 | Nguyen et al. |
| 2006/0238702 A1 | 10/2006 | Glick et al. |
| 2006/0259139 A1 | 11/2006 | Zadno-Azizi et al. |
| 2007/0027540 A1 | 2/2007 | Zadno-Azizi et al. |
| 2007/0032866 A1 | 2/2007 | Portney |
| 2007/0050025 A1 | 3/2007 | Nguyen et al. |
| 2007/0078515 A1 | 4/2007 | Brady |
| 2007/0106377 A1 | 5/2007 | Smith et al. |
| 2007/0108643 A1 | 5/2007 | Zadno-Azizi et al. |
| 2010/0324673 A1 | 12/2010 | Nguyen et al. |

FOREIGN PATENT DOCUMENTS

| | | |
|---|---|---|
| DE | 3246306 | 6/1984 |
| DE | 19501444 | 7/1996 |
| DE | 10125829 | 11/2002 |
| EP | 0162573 | 11/1985 |

| | | |
|---|---|---|
| EP | 0212616 | 3/1987 |
| EP | 246216 | 11/1987 |
| EP | 0329981 | 8/1989 |
| EP | 0337390 A2 | 10/1989 |
| EP | 0337390 A3 | 10/1989 |
| EP | 0342895 | 11/1989 |
| EP | 0351471 | 1/1990 |
| EP | 0420549 | 4/1991 |
| EP | 0336877 | 10/1993 |
| EP | 0566170 | 10/1993 |
| EP | 0691109 | 1/1996 |
| EP | 0897702 | 2/1999 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| JP | 02-126847 | 5/1990 |
| RU | 2014038 | 6/1994 |
| RU | 2014039 | 6/1994 |
| WO | WO 84/04449 | 11/1984 |
| WO | WO 85/04566 A1 * | 10/1985 |
| WO | WO 86/03961 | 7/1986 |
| WO | WO 87/00299 | 1/1987 |
| WO | WO 87/07496 | 12/1987 |
| WO | WO 89/02251 | 3/1989 |
| WO | WO 89/11672 | 11/1989 |
| WO | WO 94/16648 | 8/1994 |
| WO | WO 95/03783 | 2/1995 |
| WO | WO 95/13022 | 5/1995 |
| WO | WO 96/15734 | 5/1996 |
| WO | WO 97/43984 | 11/1997 |
| WO | WO 99/03427 | 1/1999 |
| WO | WO 99/20206 | 4/1999 |
| WO | WO 00/21467 | 4/2000 |
| WO | WO 00/27315 | 5/2000 |
| WO | WO 00/61036 | 10/2000 |
| WO | WO 00/66037 | 11/2000 |
| WO | WO 01/19289 | 3/2001 |
| WO | WO 01/34067 | 5/2001 |
| WO | WO 01/64136 | 9/2001 |
| WO | WO 01/66042 | 9/2001 |
| WO | WO 02/071983 | 9/2002 |
| WO | WO 03/009051 | 1/2003 |
| WO | WO 03/015657 | 2/2003 |
| WO | WO 03/059196 | 7/2003 |
| WO | WO 03/084441 | 10/2003 |
| WO | WO 03/092552 | 11/2003 |
| WO | WO 04/000171 | 12/2003 |
| WO | WO 2004/073559 | 9/2004 |

OTHER PUBLICATIONS

Seward Commentary: Folding Intraocular Lenses: Materials and Methods, British Journal of Opthalmology, 81: 340-341, 1997, at col. 1.

Cohen, Allen Louis, "Diffractive Bifocal Lens Design", *Optometry and Vision Science*, vol. 70, No. 6, 1993, American Academy of Optometry, pp. 461-468.

Klien, Stanely A., "Understanding the Diffractive Bifocal Contact Lens," *Optometry and Vision Science*, vol. 70, No. 6, 1993, American Academy of Optometry, pp. 439-460.

U.S. Appl. No. 11/564,482, filed Nov. 29, 2006.

"AMO Specs Model AC-21B", AMO Classic Series. PMM IntraOcular Lenses. 1992. 5 pages.

ASCRS Symposium of Cataracts IOL and Refractive Surgery. ASOA Congress on Ophthalmic Practice Management. Clinical & Surgical Staff Program. Partical Program re: ASCRS Symposium, Showing Video Tape Shown between Apr. 10-14, 1999, 2 pages.

Menezo, et al. "Endothelial study of iris-claw phakic lens: Four year follow-up". Journal Cataract Refract Surgery, vol. 24, Aug. 1998, pp. 1039-1049.

U.S. Appl. No. 09/656,661, filed Sep. 7, 2000.

U.S. Appl. No. 09/721,072, filed Nov. 22, 2000.

Chiron, Clemente Optifit Model SPSP525 Brochure Translation, Dec. 1998, 14 pages.

Chiron Vision, Nunta Mar. 20, 1997. 5 pages.

U.S. Appl. No. 12/658,947, filed Feb. 16, 2010.

New Elliptical Accommodating IOL for Cataract Surgery shown at ASCRS Symposium on Apr. 1, 1999 (Digital Video Disc).

International Search Report for PCT/US 03/23077 mailed Mar. 26, 2004 in 9 pages.

International Search Report for PCT/US 02/02473 mailed Apr. 22, 2003 in 8 pages.

European search report in related Application No. 06015136.2, dated Oct. 27, 2006, 6 pp.

European search report in related Application No. 06015132.1, dated Oct. 27, 2006, 6 pp.

Adler-Grinberg, Deborah, "Questioning Our Classical Understanding of Accommodation and Presbyopia," *American Journal of Optometry & Physiological Optics* 1986; 63: 571-580.

Altman, Griffith E. Wavefront-customized intraocular lenses, *Current Opinion in Ophthalmology 2004*, 15:358-364, 7 pages, XP009075917.

Nio, Ying-Khay, Effect of intraocular lens implantation on visual acuity, contrast sensitivity, and depth of focus, *Journal Cataract and Refractive Surgery*, vol. 29, Nov. 2003, pp. 2073-2081, XP09065364.

* cited by examiner

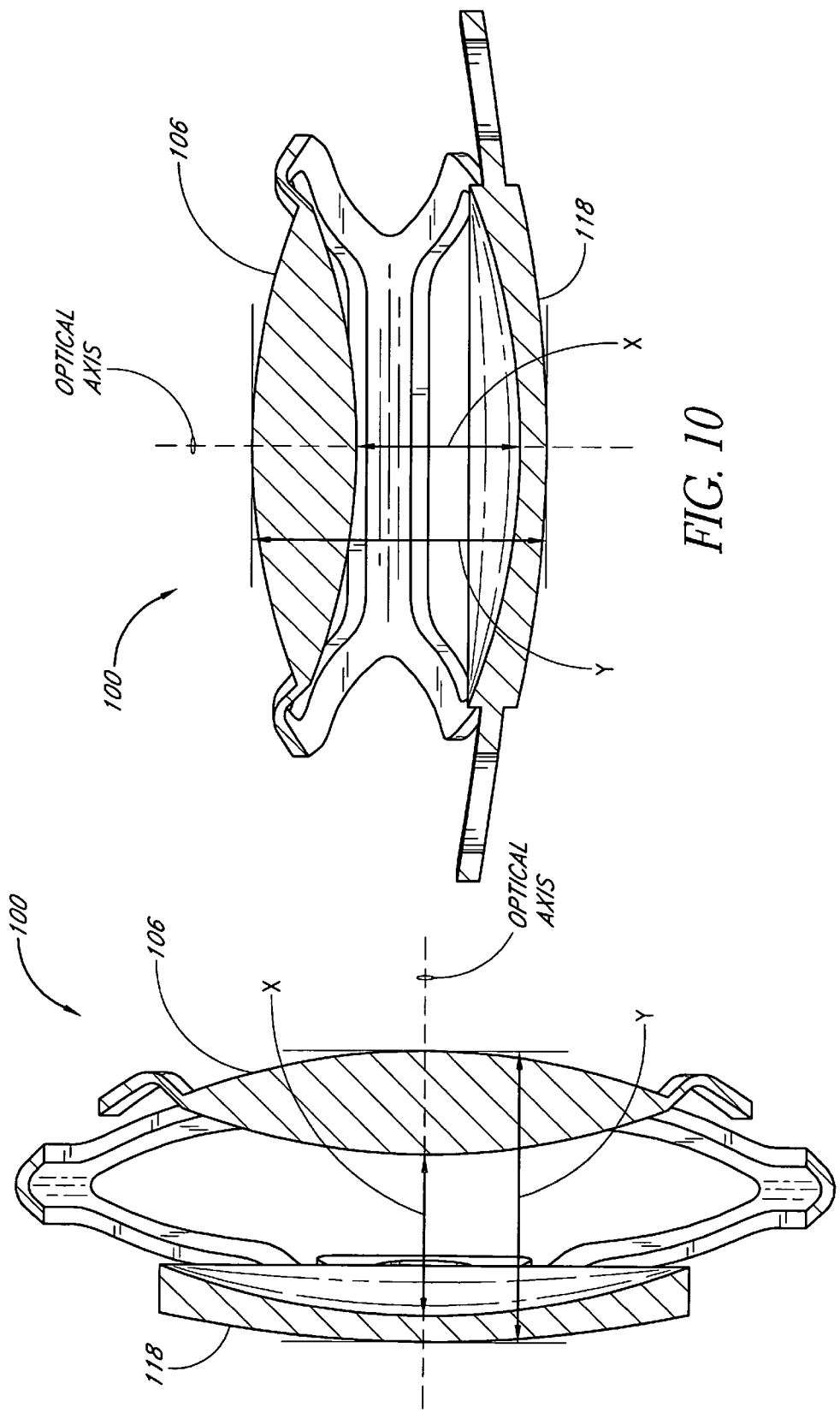

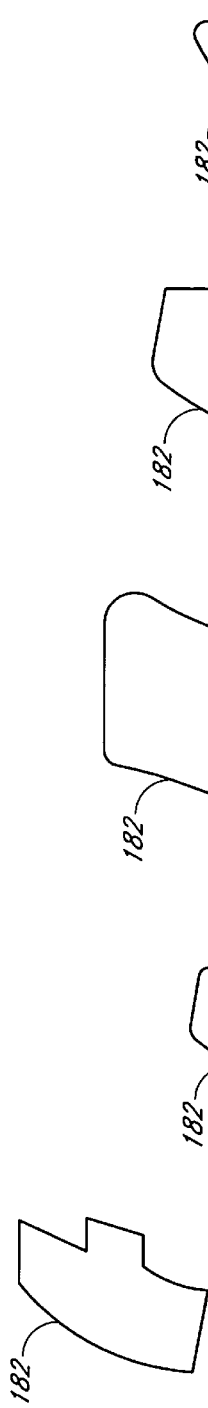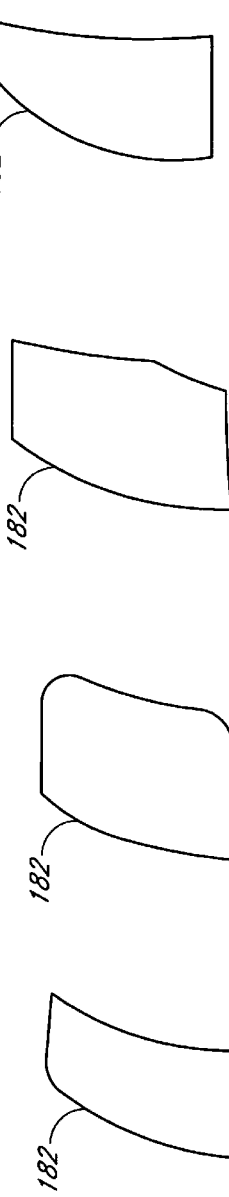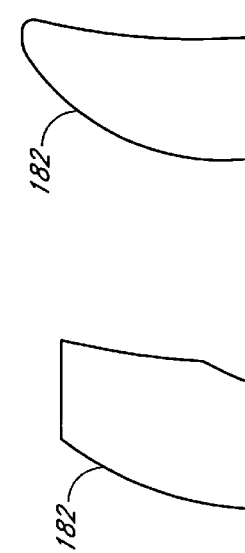

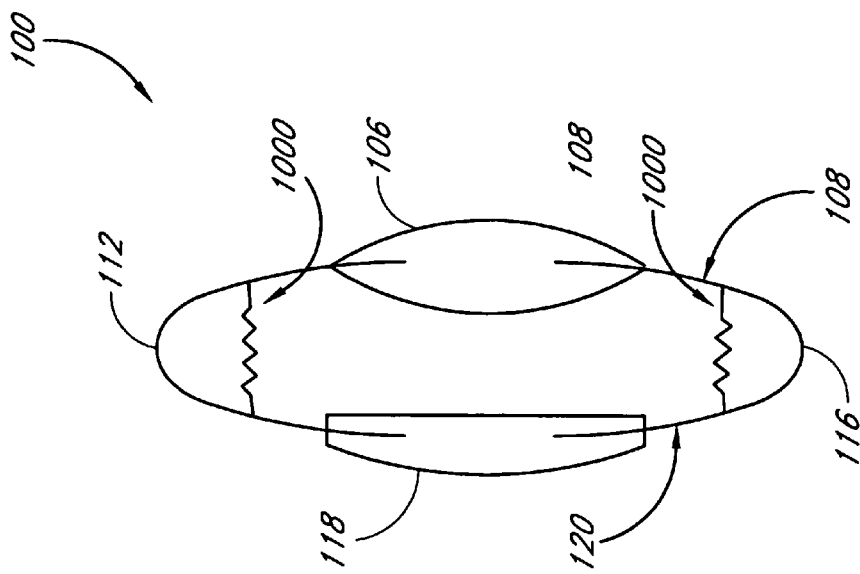
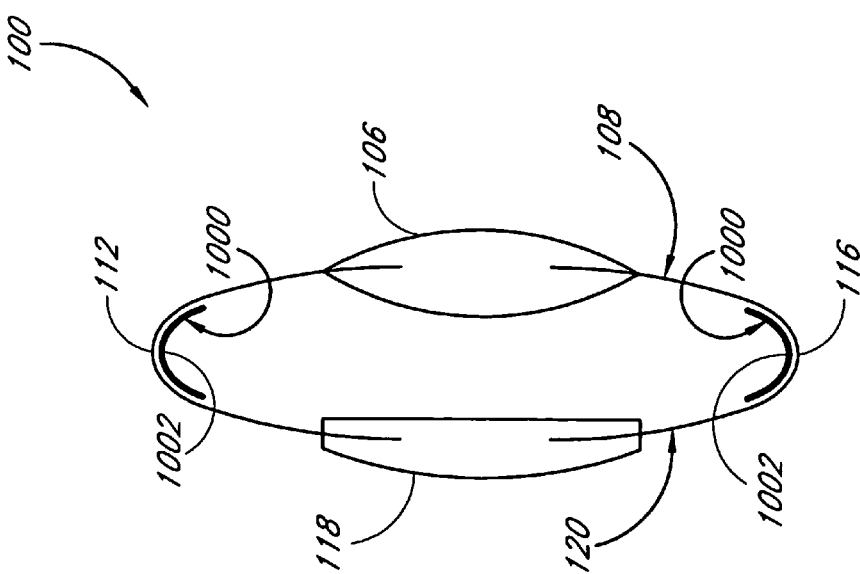

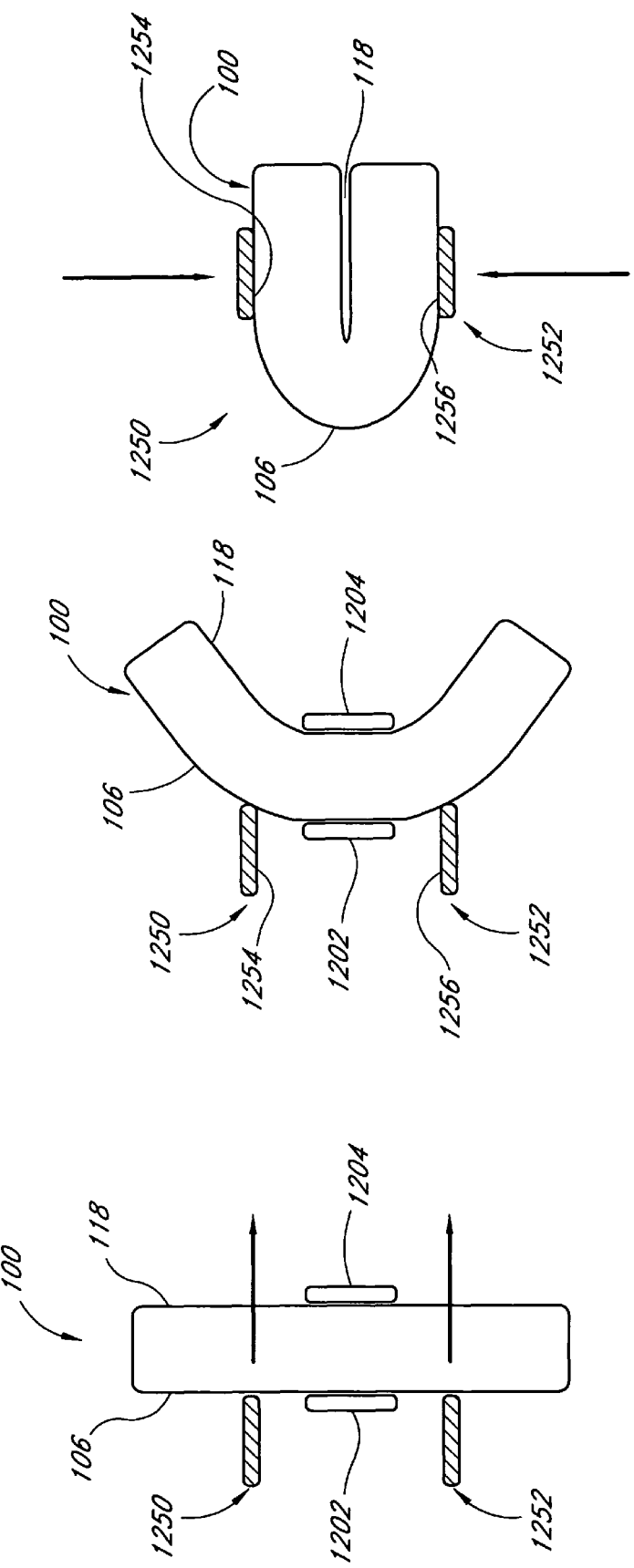

MATERIALS FOR USE IN ACCOMMODATING INTRAOCULAR LENS SYSTEM

RELATED APPLICATIONS

The present application is a continuation of U.S. patent application Ser. No. 10/207,717 (published as U.S. Patent Application Publication No. 2003/0078657), filed Jul. 25, 2002, titled MATERIALS FOR USE IN ACCOMMODATING INTRAOCULAR LENS SYSTEM, now abandoned, which is a continuation-in-part of U.S. patent application Ser. No. 10/020,853, filed Dec. 11, 2001, titled ACCOMMODATING INTRAOCULAR LENS SYSTEM, now U.S. Pat. No. 7,118,596, which claims the benefit of U.S. Provisional Patent Application Ser. No. 60/337,343, filed Nov. 9, 2001 and titled ACCOMMODATING INTRAOCULAR LENS SYSTEM; Ser. No. 60/283,856, filed Apr. 13, 2001 and titled ACCOMMODATING INTRAOCULAR LENS SYSTEM; and Ser. No. 60/264,179, filed Jan. 25, 2001 and titled ACCOMMODATING INTRAOCULAR LENS SYSTEM. In addition, the above-noted application Ser. No. 10/207,717 claims the benefit of U.S. Provisional Patent Application Ser. No. 60/337,343, filed Nov. 9, 2001 and titled ACCOMMODATING INTRAOCULAR LENS SYSTEM. The entire disclosure of all of the above-mentioned provisional and non-provisional patent applications, and of the above-mentioned publication, is hereby incorporated by reference herein and made a part of this specification.

BACKGROUND OF THE INVENTION

1. Field of the Invention

This invention relates to intraocular lenses and, more particularly, to intraocular lenses that alter the refractive power of the eye in response to changes in the tension of the ciliary muscle of the eye.

2. Description of the Related Art

The vast majority of cataract operations involve the implantation of an artificial lens following cataract removal. Typically these lenses have a fixed focal length or, in the case of bifocal or multifocal lenses, have several different fixed focal lengths. Such fixed focal-length lenses lack the ability of the natural lens to dynamically change the refractive power of the eye. The various embodiments of the intraocular lens disclosed herein provide an accommodating lens system which alters the refractive power of the eye in response to changes in tension of the ciliary muscle, thereby allowing the lens system to bring into focus on the retina images of objects that are both near and far from the eye.

SUMMARY OF THE INVENTION

One aspect of the invention is an accommodating intraocular lens for implantation in an eye having an optical axis. The lens comprises an anterior portion which in turn comprises an anterior viewing element comprised of an optic having refractive power and an anterior biasing element comprising first and second anterior translation members extending from the anterior viewing element. The lens further comprises a posterior portion which in turn comprises a posterior viewing element in spaced relationship to the anterior viewing element and a posterior biasing element comprising first and second posterior translation members extending from the posterior viewing element. The anterior portion and posterior portion meet at first and second apices of the intraocular lens such that a plane perpendicular to the optical axis and passing through the apices is closer to one of said viewing elements than to the other of said viewing elements. The anterior portion and the posterior portion are responsive to force thereon to cause the separation between the viewing elements to change.

Another aspect of the invention is an accommodating intraocular lens for implantation in an eye having an optical axis. The lens comprises an anterior portion, which in turn comprises an anterior viewing element comprised of an optic having refractive power, and an anterior biasing element comprising first and second anterior translation members extending from the anterior viewing element. The lens further comprises a posterior portion which in turn comprises a posterior viewing element in spaced relationship to the anterior viewing element, and a posterior biasing element comprising first and second posterior translation members extending from the posterior viewing element. The anterior portion and posterior portion meet at first and second apices of the intraocular lens. The anterior portion and the posterior portion are responsive to force thereon to cause the separation between the viewing elements to change. The first anterior translation member forms a first anterior biasing angle, as the lens is viewed from the side, with respect to a plane perpendicular to the optical axis and passing through the apices. The first posterior translation member forms a first posterior biasing angle, as the lens is viewed from the side, with respect to the plane. The first anterior biasing angle and the first posterior biasing angle are unequal.

Another aspect of the invention is an accommodating intraocular lens comprising an anterior viewing element comprised of an optic having refractive power of less than 55 diopters and a posterior viewing element comprised of an optic having refractive power. The optics provide a combined power of 15-25 diopters and are mounted to move relative to each other along the optical axis in response to a contractile force by the ciliary muscle of the eye upon the capsular bag of the eye. The relative movement corresponds to change in the combined power of the optics of at least one diopter. Alternatively, the accommodating intraocular lens can further comprise a posterior viewing element comprised of an optic having a refractive power of zero to minus 25 diopters.

A further aspect of the invention is an accommodating intraocular lens comprising an anterior portion which in turn comprises an anterior viewing element which has a periphery and is comprised of an optic having refractive power. The anterior portion further comprises an anterior biasing element comprising first and second anterior translation members extending from the anterior viewing element. The lens further comprises a posterior portion which in turn comprises a posterior viewing element having a periphery, the posterior viewing element being in spaced relationship to the anterior viewing element, and a posterior biasing element comprising first and second posterior translation members extending from the posterior viewing element. The first anterior translation member and the first posterior translation member meet at a first apex of the intraocular lens, and the second anterior translation member and the second posterior translation member meet at a second apex of the intraocular lens, such that force on the anterior portion and the posterior portion causes the separation between the viewing elements to change. Each of the translation members is attached to one of the viewing elements at at least one attachment location. All of the attachment locations are further away from the apices than the peripheries of the viewing elements are from the apices.

A further aspect of the invention is an accommodating intraocular lens comprising an anterior portion comprised of a viewing element. The viewing element is comprised of an optic having refractive power. The lens further comprises a posterior portion comprised of a viewing element. The viewing elements are mounted to move relative to each other along the optical axis in response to force generated by the ciliary muscle of the eye. The lens further comprises a distending portion comprised of a distending member having a fixed end attached to the posterior portion and a free end sized and oriented to distend a portion of the lens capsule such that coupling of forces between the lens capsule and the intraocular lens is modified by the distending portion.

A further aspect of the invention is an accommodating intraocular lens. The lens comprises an anterior portion comprised of an anterior viewing element and an anterior biasing element connected to the anterior viewing element. The anterior viewing element is comprised of an optic having refractive power. The lens further comprises a posterior portion comprised of a posterior viewing element and a posterior biasing element connected to the posterior viewing element. The lens has an optical axis which is adapted to be substantially coincident with the optical axis of the eye upon implantation of the lens. The anterior and posterior viewing elements are mounted to move relative to each other along the optical axis in response to force generated by the ciliary muscle of the eye. The biasing elements are joined at first and second apices which are spaced from the optical axis of the lens. The lens further comprises a distending member extending between the first and second apices.

A further aspect of the invention is an accommodating intraocular lens comprising an anterior portion comprised of a viewing element. The viewing element is comprised of an optic having refractive power. The lens further comprises a posterior portion comprised of a viewing element. The viewing elements are mounted to move relative to each other along the optical axis in response to force generated by the ciliary muscle of the eye. The lens further comprises a retention portion comprised of a retention member having a fixed end attached to the anterior portion and a free end sized and oriented to contact a portion of the lens capsule such that extrusion of the implanted lens through the lens capsule opening is inhibited.

A further aspect of the invention is an accommodating intraocular lens. The lens comprises an anterior portion comprised of a viewing element, the viewing element comprised of an optic having refractive power, and a posterior portion comprised of a viewing element. The viewing elements are mounted to move relative to each other along the optical axis in response to force generated by the ciliary muscle of the eye. The lens further comprises a distending portion comprised of a distending member attached to one of the portions, and oriented to distend the lens capsule such that the distance between a posterior side of the posterior viewing element and an anterior side of the anterior viewing element along the optical axis is less than 3 mm when the ciliary muscle is relaxed and the lens is in an unaccommodated state.

A further aspect of the invention is an accommodating intraocular lens. The lens comprises an anterior portion comprised of a viewing element, the viewing element comprised of an optic having refractive power, and a posterior portion comprised of a viewing element. The viewing elements are mounted to move relative to each other along the optical axis in response to force generated by the ciliary muscle of the eye. The lens further comprises a distending portion comprised of a distending member attached to one of the portions, and oriented to distend the lens capsule. The distending causes the lens capsule to act on at least one of the posterior and anterior portions such that separation between the viewing elements is reduced when the ciliary muscle is relaxed and the lens is in an unaccommodated state.

A further aspect of the invention is an accommodating intraocular lens. The lens comprises an anterior portion comprised of a viewing element, the viewing element comprised of an optic having refractive power, and a posterior portion comprised of a viewing element. The viewing elements are mounted to move relative to each other along the optical axis in response to force generated by the ciliary muscle of the eye. The lens further comprises a distending member attached to the posterior portion. The distending member is separate from the biasing members and reshapes the lens capsule such that force coupling between the ciliary muscle and the lens is modified to provide greater relative movement between the viewing elements when the lens moves between an unaccommodated state and an accommodated state in response to the ciliary muscle.

A further aspect of the invention is an accommodating intraocular lens. The lens comprises an anterior portion comprised of an anterior viewing element and an anterior biasing element connected to the anterior viewing element, the anterior viewing element being comprised of an optic having refractive power. The lens further comprises a posterior portion comprised of a posterior viewing element and a posterior biasing element connected to the posterior viewing element. The lens has an optical axis which is adapted to be substantially coincident with the optical axis of the eye upon implantation of the lens. The anterior and posterior viewing elements are mounted to move relative to each other along the optical axis in response to force generated by the ciliary muscle of the eye. The biasing elements are joined at first and second apices which are spaced from the optical axis of the lens. The lens further comprises first and second distending members. Each of the members is attached to one of the anterior and posterior portions and extends away from the optical axis. The first member is disposed between the apices on one side of the intraocular lens and the second member is disposed between the apices on the opposite side of the intraocular lens. The distending members are oriented to distend portions of the lens capsule such that the viewing elements are relatively movable through a range of at least 1.0 mm in response to contraction of the ciliary muscle.

A further aspect of the invention is an accommodating intraocular lens comprising an anterior portion which is in turn comprised of a viewing element. The anterior viewing element is comprised of an optic having a diameter of approximately 3 mm or less and a refractive power of less than 55 diopters. The lens further comprises a posterior portion comprised of a viewing element. The viewing elements are mounted to move relative to each other along the optical axis in response to force generated by the ciliary muscle of the eye. The lens further comprises a distending portion comprised of a distending member having a fixed end attached to the posterior portion and a free end sized and oriented to distend a portion of the lens capsule such that coupling of forces between the lens capsule and the intraocular lens is increased.

A further aspect of the invention is an accommodating intraocular lens. The lens comprises an anterior portion comprised of a viewing element, the anterior viewing element being comprised of an optic having a refractive portion with a refractive power of less than 55 diopters. The lens further comprises a posterior portion comprised of a viewing element. The lens has an optical axis which is adapted to be substantially coincident with the optical axis of the eye upon implantation of the lens. The posterior viewing element comprises an optic arranged substantially coaxially with the anterior optic on the optical axis of the lens. The posterior optic has a larger diameter than the refractive portion of the anterior optic. The posterior optic comprises a peripheral portion having positive refractive power and extending radially away from the optical axis of the lens beyond the periphery of the refractive portion of the anterior optic, so that at least a portion of the light rays incident upon the posterior optic can bypass the refractive portion of the anterior optic.

A further aspect of the invention is an accommodating intraocular lens. The lens comprises an anterior portion comprised of a viewing element, the anterior viewing element being comprised of an optic having a refractive power of less than 55 diopters. The lens further comprises a posterior portion comprised of a viewing element. The lens has an optical axis which is adapted to be substantially coincident with the optical axis of the eye upon implantation of the lens. The posterior viewing element comprises an optic arranged substantially coaxially with the anterior optic on the optical axis of the lens. The posterior optic has a larger diameter than the anterior optic. The posterior optic comprises a peripheral portion having positive refractive power and extending radially away from the optical axis of the lens beyond the periphery of the anterior optic, so that at least a portion of the light rays incident upon the posterior optic can bypass the anterior optic.

A further aspect of the invention is an intraocular lens. The lens comprises an optic and a pair of elongate members extending from the optic. The members are comprised of a shape memory alloy.

A further aspect of the invention is an accommodating intraocular lens for implantation in an eye having an optical axis and a lens capsule having a capsule opening for receiving the lens. The lens comprises a posterior portion comprised of a posterior viewing element, and an anterior portion comprised of an anterior viewing element. The anterior viewing element is comprised of an optic having refractive power. The viewing elements are mounted to move relative to each other along the optical axis in response to force generated by the ciliary muscle of the eye. The anterior portion is adapted to contact portions of the lens capsule while being spaced from the lens capsule in at least one location so as to provide a fluid flow channel that extends from a region between the viewing elements to a region outside the capsule.

A further aspect of the invention is an accommodating intraocular lens. The lens comprises an anterior portion which in turn comprises an anterior viewing element having a periphery and comprised of an optic having refractive power, and an anterior biasing element comprising at least one anterior translation member attached to a first attachment area on the periphery of the anterior viewing element. The first attachment area has a thickness in a direction substantially perpendicular to the periphery and a width in a direction substantially parallel to the periphery. The ratio of the width to the thickness is equal to or greater than 3.

A further aspect of the invention is a method of manufacturing an intraocular lens having anterior and posterior viewing elements arranged along a common optical axis. The method comprises defining an anterior viewing element mold space and a posterior viewing element mold space, arranging the anterior viewing element mold space and the posterior viewing element mold space along a mold axis substantially coincident with the optical axis of the lens, and molding the anterior viewing element in the anterior viewing element mold space while the anterior viewing element mold space and the posterior viewing element mold space are arranged substantially along the mold axis.

A further aspect of the invention is a method of preparing an accommodating intraocular lens having an optical axis for subsequent implantation. The method comprises providing an intraocular lens having first and second viewing elements interconnected by plural members. At least a portion of the members are disposed from the optical axis by a distance greater than a periphery of at least one of the viewing elements. This distance is measured orthogonal to the optical axis. The method further comprises drawing the members inwardly toward the optical axis by relatively rotating the first and second viewing elements. In one variation of the method, the first and second viewing elements are relatively rotated about the optical axis.

A further aspect of the invention is an accommodating intraocular lens, which comprises an anterior portion having an anterior viewing element, and a posterior portion having a posterior viewing element. The viewing elements are positioned to move relative to each other along an optical axis in response to action of the ciliary muscle of the eye. The anterior and posterior portions comprise a single piece of material.

A further aspect of the invention is an accommodating intraocular lens, which comprises first and second optics. At least one of the optics has refractive power. The optics are mounted by an articulated frame to move relative to each other along an optical axis in response to action of a ciliary muscle. The frame is formed of a single piece of material. In one variation of the lens, at least one of the optics is formed of a material which is different from the material of the frame.

A further aspect of the invention is an accommodating intraocular lens, which comprises an anterior portion having an anterior viewing element comprising an optic having refractive power. The lens further comprises a posterior portion having a posterior viewing element. The viewing elements are positioned to move relative to each other along an optical axis in response to action of the ciliary muscle of the eye. At least one of the anterior and posterior portions has at least one separation member with a contact surface. The at least one separation member is configured to prevent contact between the anterior viewing element and the posterior viewing element by inhibiting relative movement of the anterior and posterior portions toward each other beyond a minimum separation distance. The contact surface contacts an opposing surface of the intraocular lens over a contact area when the portions are at the minimum separation distance. At least one of the surfaces has an adhesive affinity for the other of the surfaces. The contact area is sufficiently small to prevent adhesion between the surfaces when the anterior portion and the posterior portion are separated by the minimum separation distance. In one variation of the lens, the contact surface and the opposing surface are comprised of the same material.

A further aspect of the invention is an intraocular lens, which comprises first and second interconnected viewing elements mounted to move relative to each other along an optical axis in response to action of a ciliary muscle. At least one of the viewing elements includes an optic having refractive power. The lens is formed by the process of providing a first outer mold and a second outer mold, and an inner mold therebetween. The first outer mold and the inner mold define a first mold space, and the second outer mold and the inner mold define a second mold space. The process further comprises molding the viewing elements and the optic as a single piece by filling the first and second mold spaces with a material, such that the first viewing element is formed in the first mold space and the second viewing element is formed in the second mold space. The process further comprises removing the first and second outer molds from the lens while the inner mold remains between the viewing elements, and removing the inner mold from between the viewing elements while the viewing elements remain interconnected.

A further aspect of the invention is a method of making an intraocular lens having first and second interconnected viewing elements wherein at least one of the viewing elements includes an optic having refractive power. The method comprises providing a first outer mold and a second outer mold, and an inner mold therebetween. The first outer mold and the inner mold define a first mold space, and the second outer mold and the inner mold define a second mold space. The process further comprises molding the viewing elements and the optic as a single piece by filling the first and second mold spaces with a material, such that the first viewing element is formed in the first mold space and the second viewing element is formed in the second mold space. The process further comprises removing the first and second outer molds from the lens while the inner mold remains between the viewing elements, and removing the inner mold from between the viewing elements while the viewing elements remain interconnected. In one variation, providing the inner mold may comprise molding the inner mold. In another variation, the inner mold has a first inner mold face and a second inner mold face opposite the first inner mold face, and providing the inner mold comprises machining the inner mold, which in turn comprises machining the first inner mold face and the second inner mold face in a single piece of material.

A further aspect of the invention is an accommodating intraocular lens, which comprises first and second optics. At least one of the optics has refractive power. The optics are mounted to move relative to each other along an optical axis in response to action of a ciliary muscle. The first optic is formed of a first polymer having a number of recurring units including first-polymer primary recurring units, and the second optic is formed of a second polymer having a number of recurring units including second-polymer primary recurring units. No more than about 10 mole percent of the recurring units of the first polymer are the same as the second-polymer primary recurring units and no more than about 10 mole percent of the recurring units of the second polymer are the same as the first-polymer primary recurring units. In one variation, the first optic may comprise an anterior optic, the second optic may comprise a posterior optic, the first polymer may comprise silicone, and the second polymer may comprise acrylic. In another variation, the first optic may comprise an anterior optic, the second optic may comprise a posterior optic, the first polymer may comprise high-refractive-index silicone, and the second polymer may comprise hydrophobic acrylic.

All of these aspects are intended to be within the scope of the invention herein disclosed. These and other aspects of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention, certain preferred embodiments and modifications thereof will become apparent to those skilled in the art from the detailed description herein having reference to the figures that follow, of which:

FIG. 9 is a side sectional view of the lens system.

FIG. 10 is a top sectional view of the lens system.

FIGS. 17C-17L are sectional views of other embodiments of the arm of the lens system.

FIG. 38C is a schematic view of biasers installed in the lens system.

FIG. 38D is a schematic view of another type of biasers installed in the lens system.

FIG. 40D illustrates another stage of the folding technique.
FIG. 40E illustrates another stage of the folding technique.
FIG. 40F illustrates another stage of the folding technique.

DETAILED DESCRIPTION OF THE PREFERRED EMBODIMENT

I. The Human Eye and Accommodation

Figure 1:
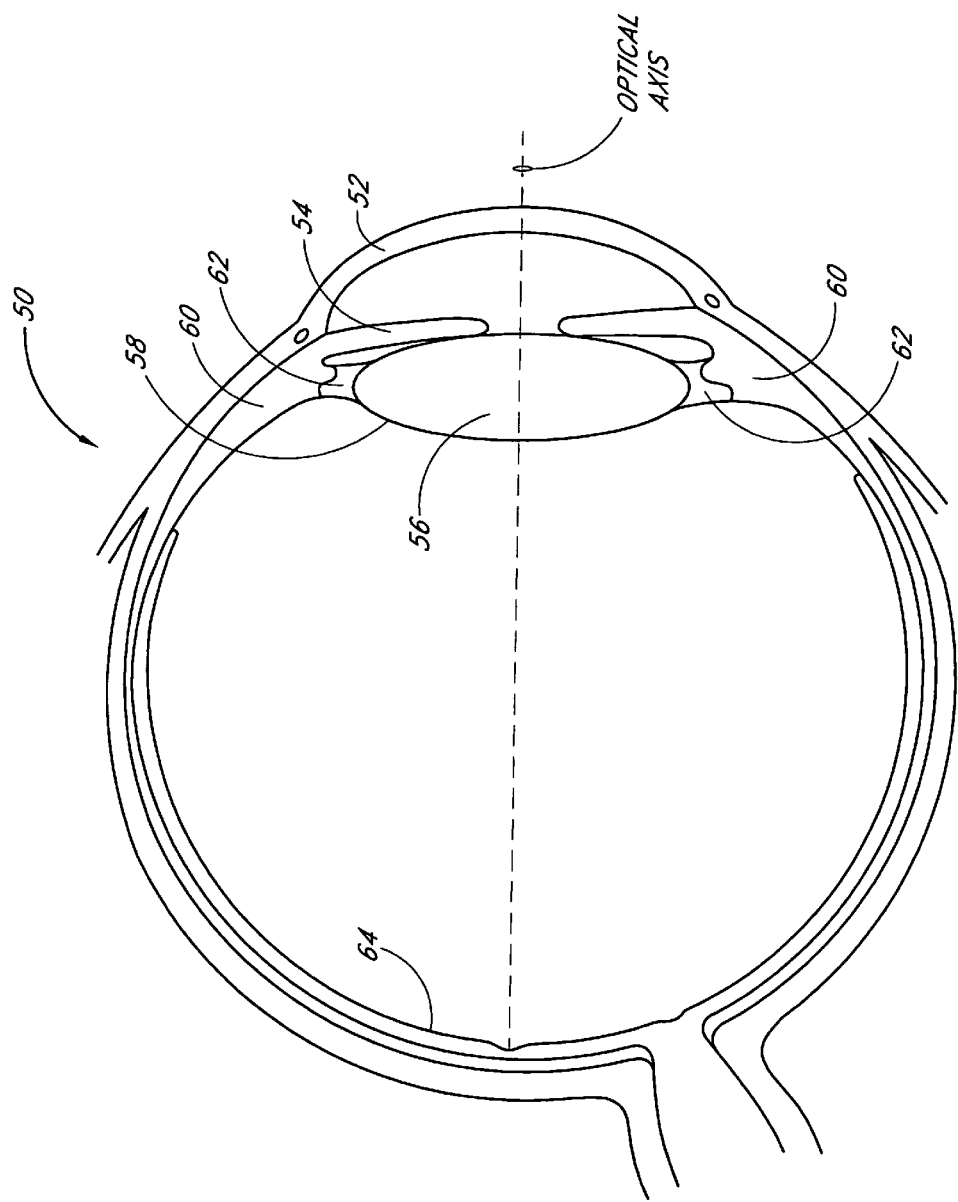
FIG. 1 is a sectional view of the human eye, with the lens in the unaccommodated state.
Figure 2:
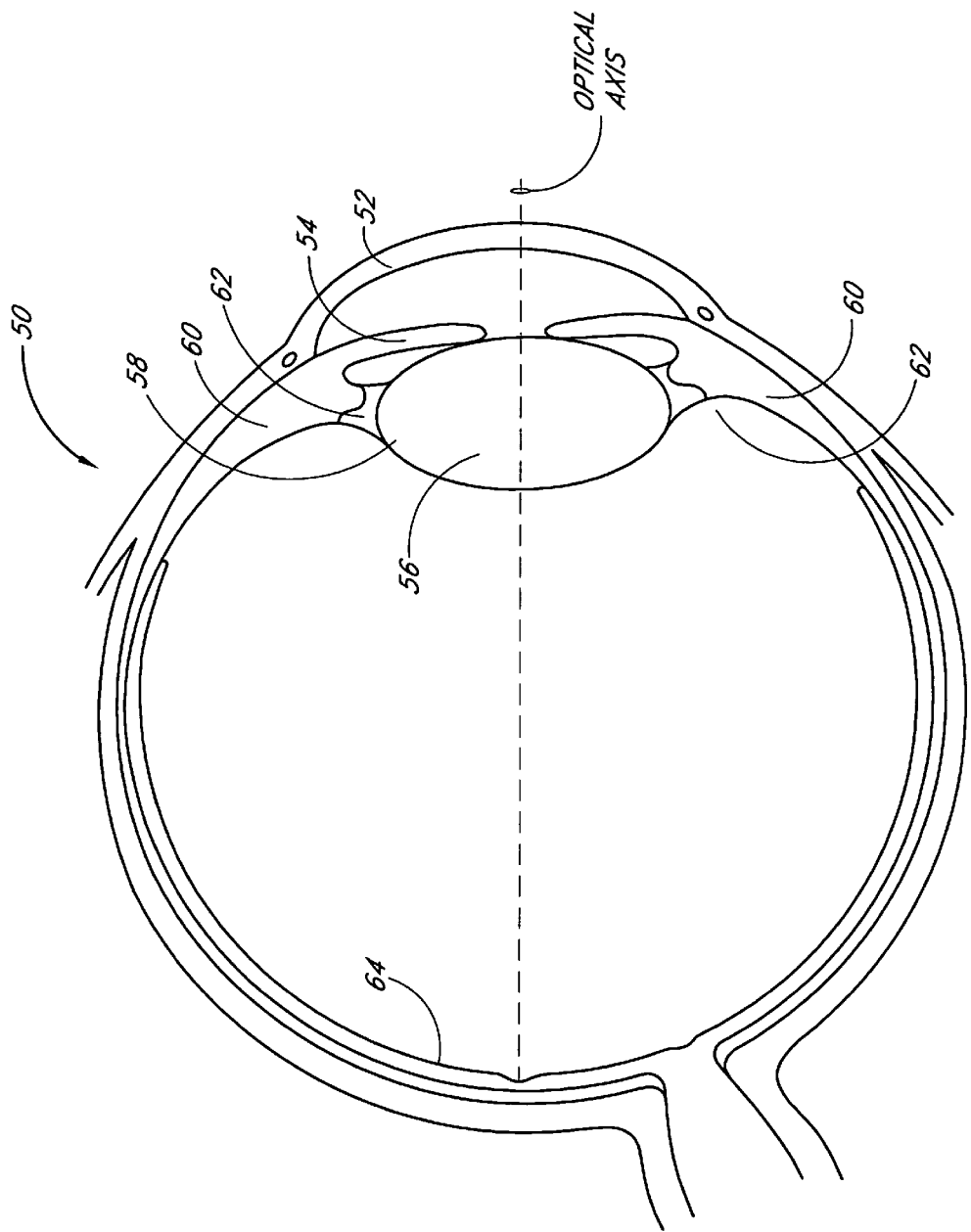
FIG. 2 is a sectional view of the human eye, with the lens in the accommodated state.

FIGS. 1 and 2 show the human eye 50 in section. Of particular relevance to the present disclosure are the cornea 52, the iris 54 and the lens 56, which is situated within the elastic, membranous capsular bag or lens capsule 58. The capsular bag 58 is surrounded by and suspended within the ciliary muscle 60 by ligament-like structures called zonules 62.

As light enters the eye 50, the cornea 52 and the lens 56 cooperate to focus the incoming light and form an image on the retina 64 at the rear of the eye, thus facilitating vision. In the process known as accommodation, the shape of the lens 56 is altered (and its refractive properties thereby adjusted) to allow the eye 50 to focus on objects at varying distances. A typical healthy eye has sufficient accommodation to enable focused vision of objects ranging in distance from infinity (generally defined as over 20 feet from the eye) to very near (closer than 10 inches).

The lens 56 has a natural elasticity, and in its relaxed state assumes a shape that in cross-section resembles a football. Accommodation occurs when the ciliary muscle 60 moves the lens from its relaxed or "unaccommodated" state (shown in FIG. 1) to a contracted or "accommodated" state (shown in FIG. 2). Movement of the ciliary muscle 60 to the relaxed/unaccommodated state increases tension in the zonules 62 and capsular bag 58, which in turn causes the lens 56 to take on a thinner (as measured along the optical axis) or taller shape as shown in FIG. 1. In contrast, when the ciliary muscle 60 is in the contracted/accommodated state, tension in the zonules 62 and capsular bag 58 is decreased and the lens 56 takes on the fatter or shorter shape shown in FIG. 2. When the ciliary muscles 60 contract and the capsular bag 58 and zonules 62 slacken, some degree of tension is maintained in the capsular bag 58 and zonules 62.

II. The Lens System: Structure

Figure 3:
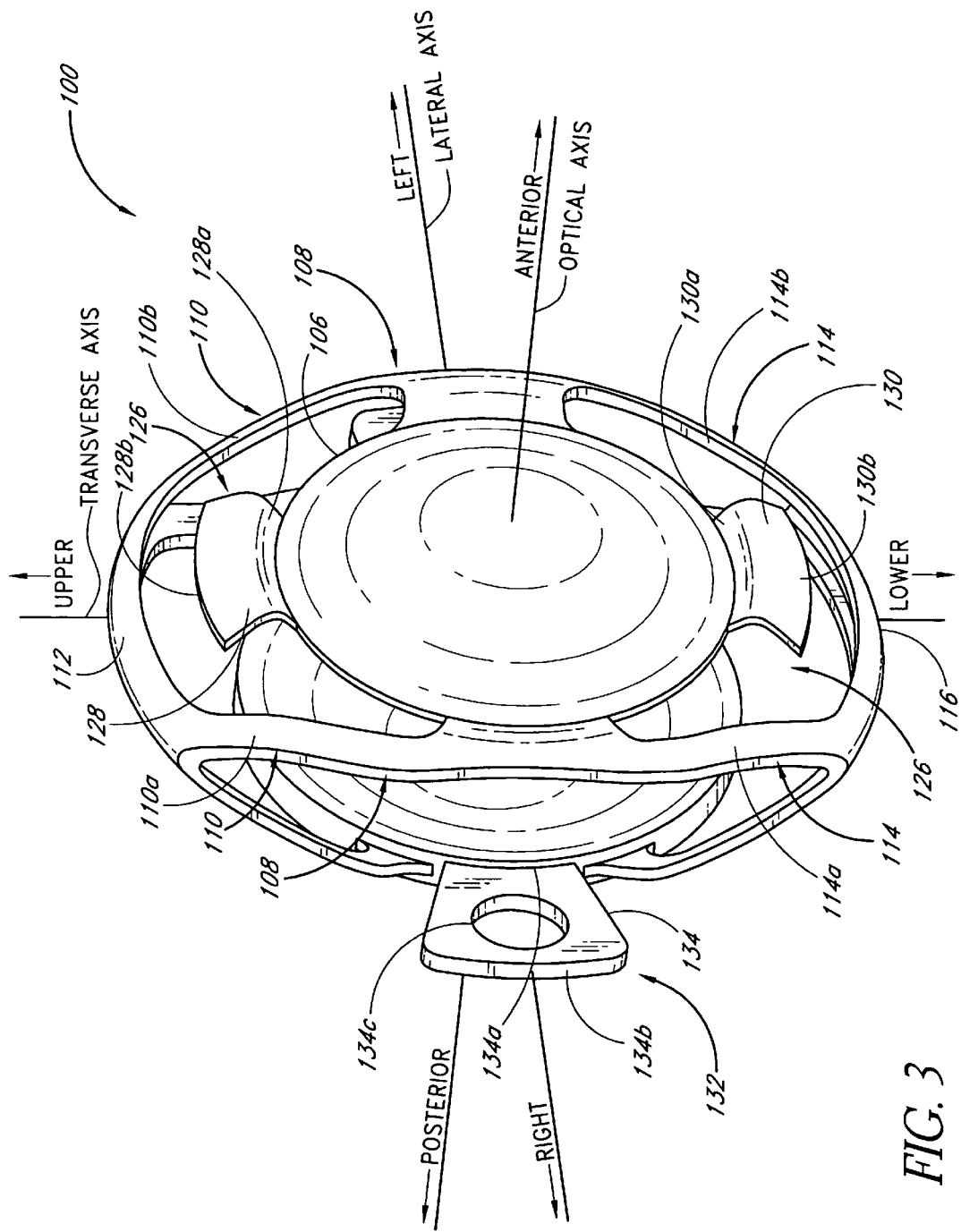
FIG. 3 is a perspective view of one embodiment of an intraocular lens system.

FIGS. 3-17 depict one embodiment of an intraocular lens system 100 which is configured for implantation into the capsular bag 58 in place of the natural lens 56, and is further configured to change the refractive properties of the eye in response to the eye's natural process of accommodation. With reference to FIG. 3, a set of axes is included to illustrate the sense of directional terminology which will be used herein to describe various features of the lens system 100. The terms "anterior" and "posterior" refer to the depicted directions on the optical axis of the lens 100 shown in FIG. 3. When the lens 100 is implanted in an eye, the anterior direction extends toward the cornea and the posterior direction extends toward the retina, with the optical axis of the lens substantially coincident with the optical axis of the eye shown in FIGS. 1 and 2. The terms "left" and "right" refer to the directions shown on the lateral axis, which is orthogonal to the optical axis. In addition, the terms "upper" and "lower" refer to the directions depicted on the transverse axis which is orthogonal to both of the optical axis and the lateral axis.

This system of axes is depicted purely to facilitate description herein; thus, it is not intended to limit the possible orientations which the lens system 100 may assume during use. For example, the lens system 100 may rotate about, or may be displaced along, the optical axis during use without detracting from the performance of the lens. It is clear that, should the lens system 100 be so rotated about the optical axis, the transverse axis may no longer have an upper-lower orientation and the lateral axis may no longer have a left-right orientation, but the lens system 100 will continue to function as it would when oriented as depicted in FIG. 3. Accordingly, when the terms "upper," "lower," "left" or "right" are used in describing features of the lens system 100, such use should not be understood to require the described feature to occupy the indicated position at any or all times during use of the lens system 100. Similarly, such use should not be understood to require the lens system 100 to maintain the indicated orientation at any or all times during use.

Figure 4:
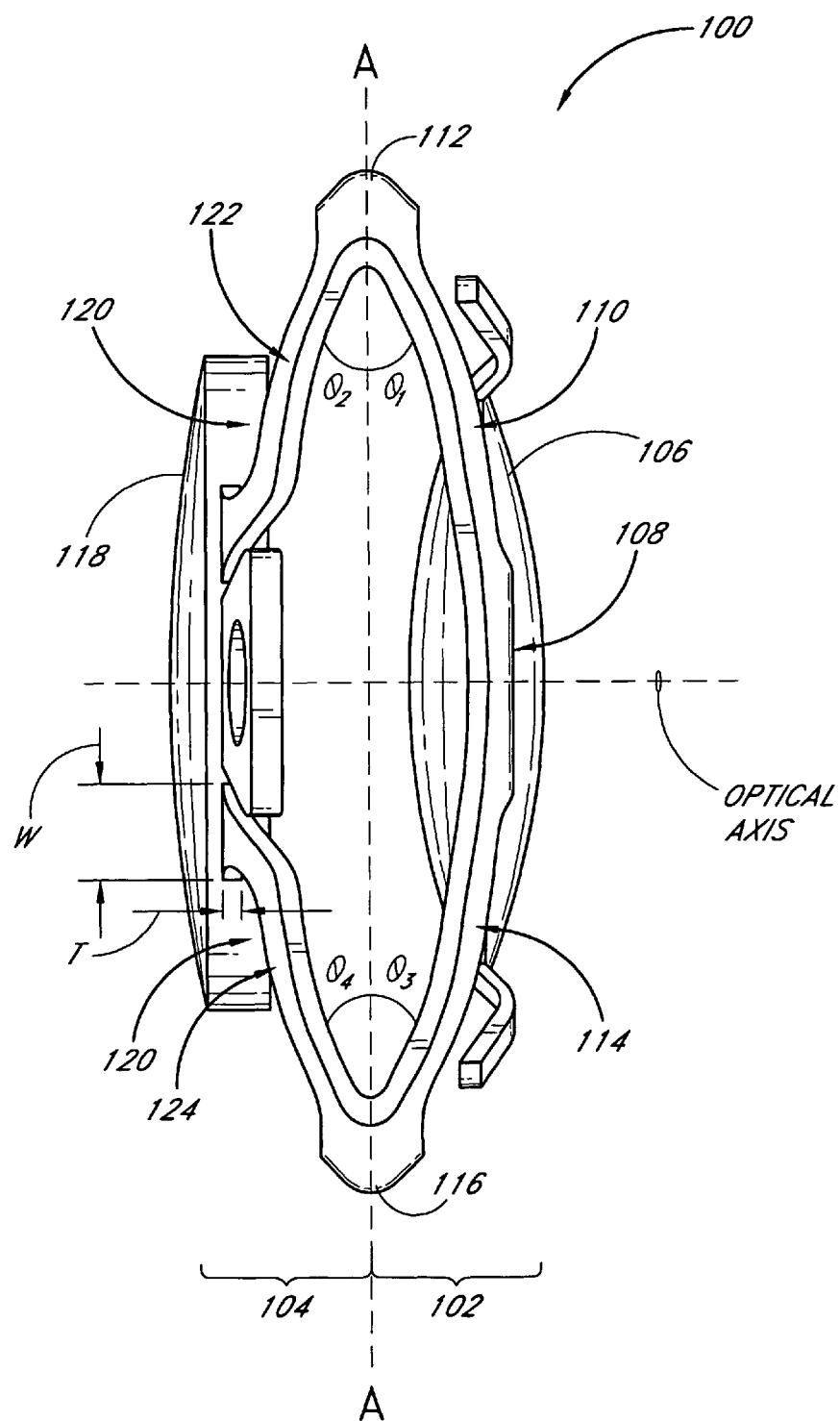
FIG. 4 is a side view of the lens system.

As best seen in FIG. 4, the lens system 100 has an anterior portion 102 which is anterior or forward of the line A-A (which represents a plane substantially orthogonal to the optical axis and intersecting first and second apices 112, 116) and a posterior portion 104 which is posterior or rearward of the line A-A. The anterior portion 102 comprises an anterior viewing element 106 and an anterior biasing element 108. The anterior biasing element 108 in turn comprises a first anterior translation member 110 which extends from the anterior viewing element 106 to the first apex 112 and a second anterior translation member 114 which extends from the anterior viewing element 106 to the second apex 116. In the illustrated embodiment the first anterior translation member 110 comprises a right arm 110a and a left arm 110b (see FIG. 3). In addition, the depicted second anterior translation member 114 comprises a right arm 114a and a left arm 114b. However, in other embodiments either or both of the first and second anterior translation members 110, 114 may comprise a single arm or member, or more than two arms or members.

Figure 5:
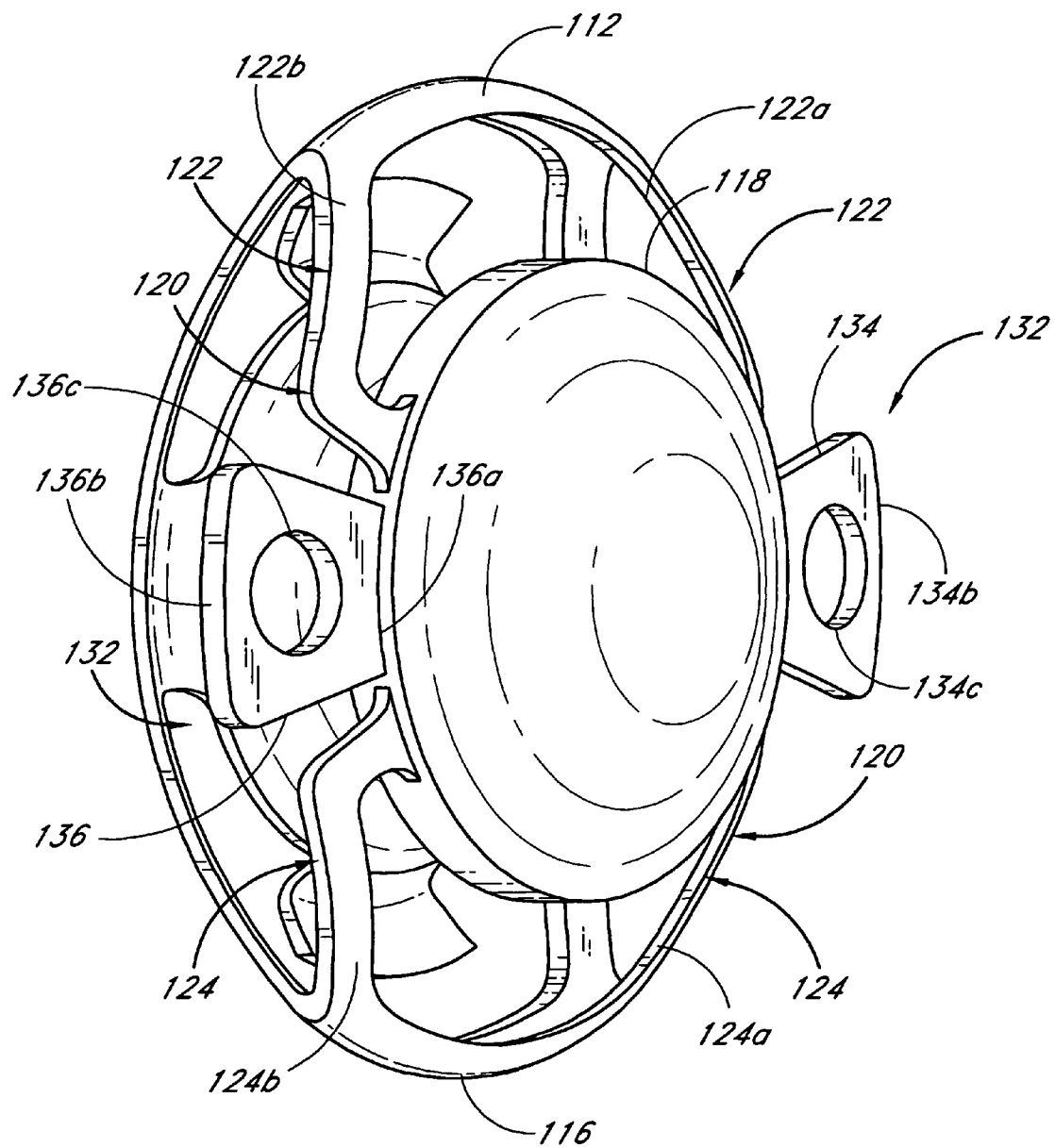
FIG. 5 is a rear perspective view of the lens system.
Figure 7:
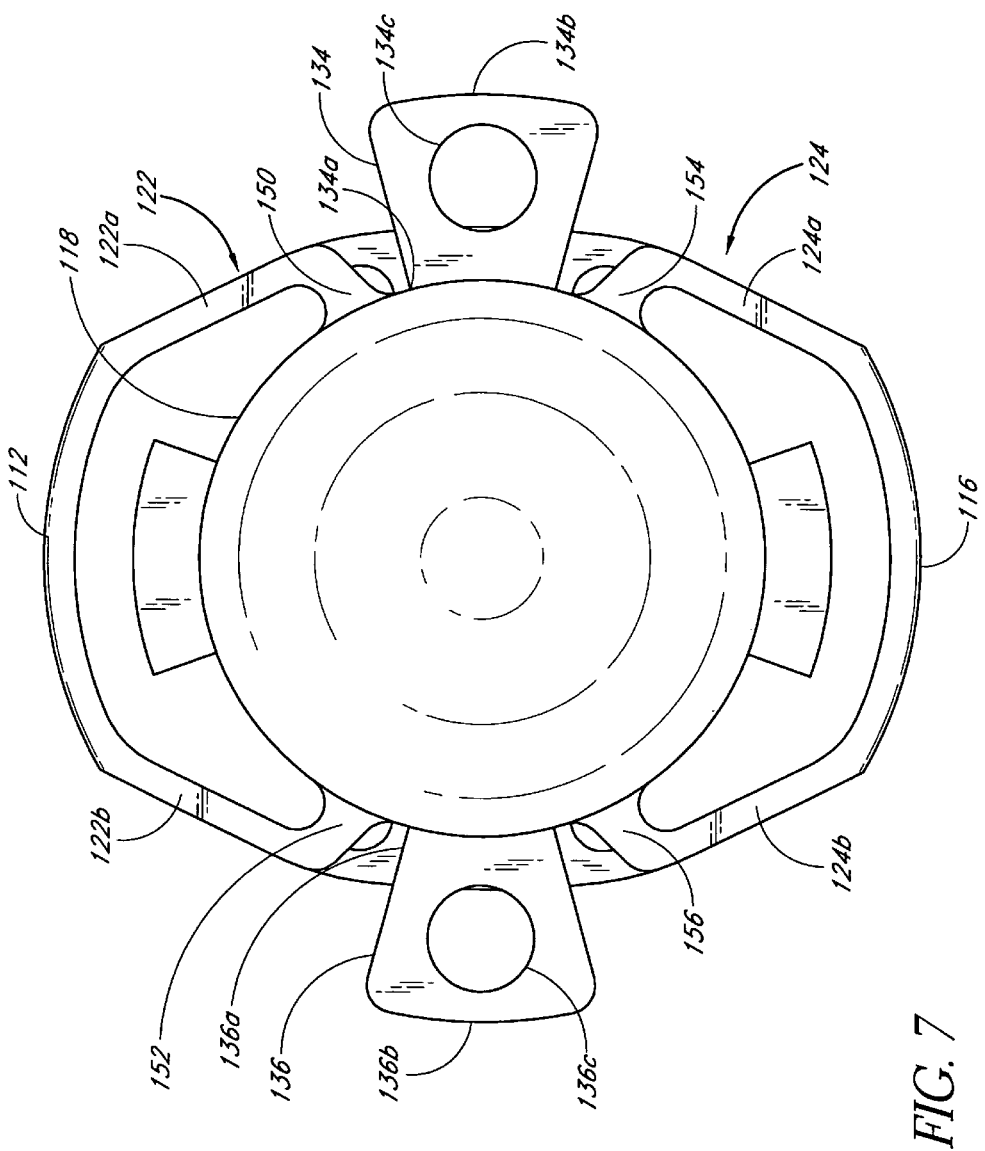
FIG. 7 is a rear view of the lens system.
Figure 8:
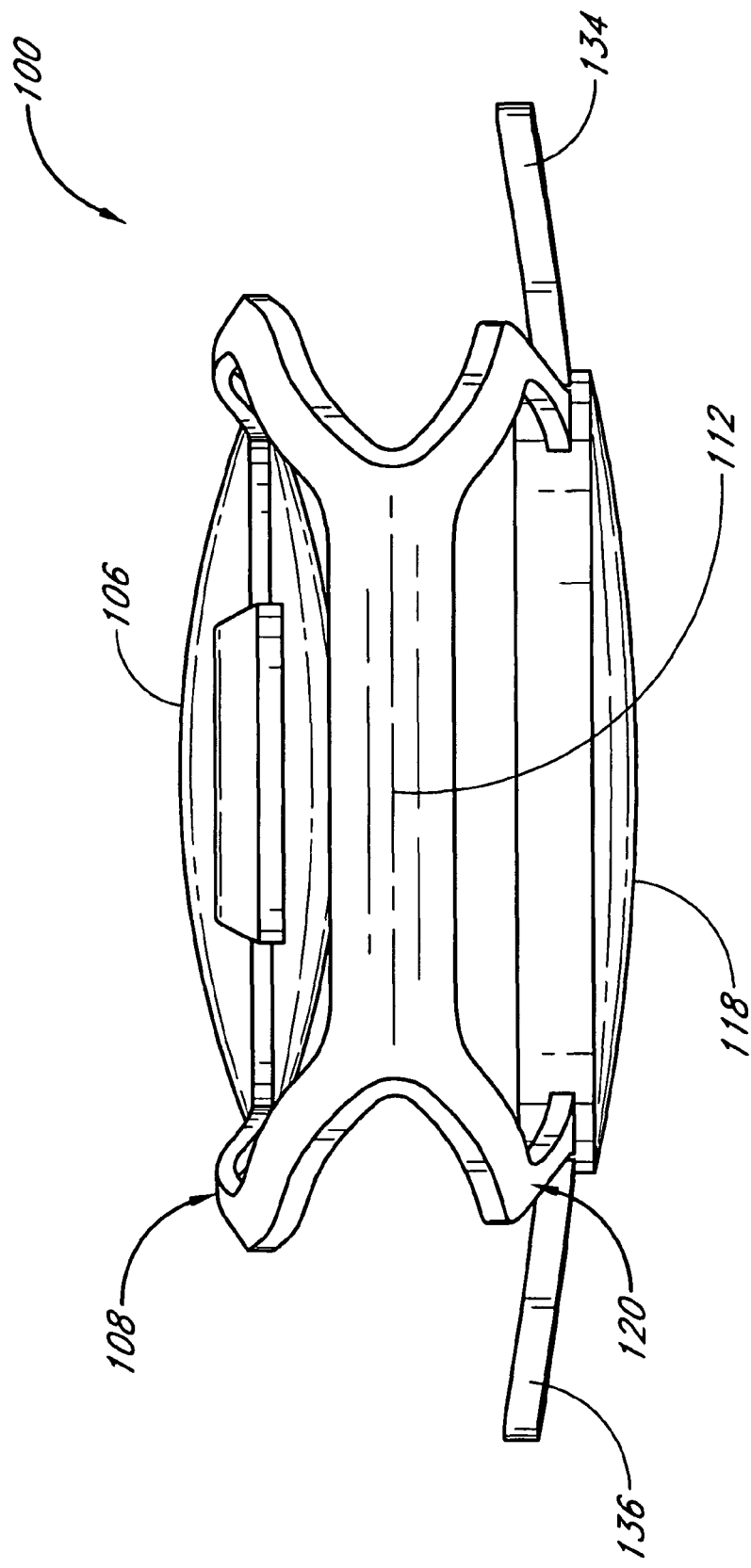
FIG. 8 is a top view of the lens system.
Figure 11:
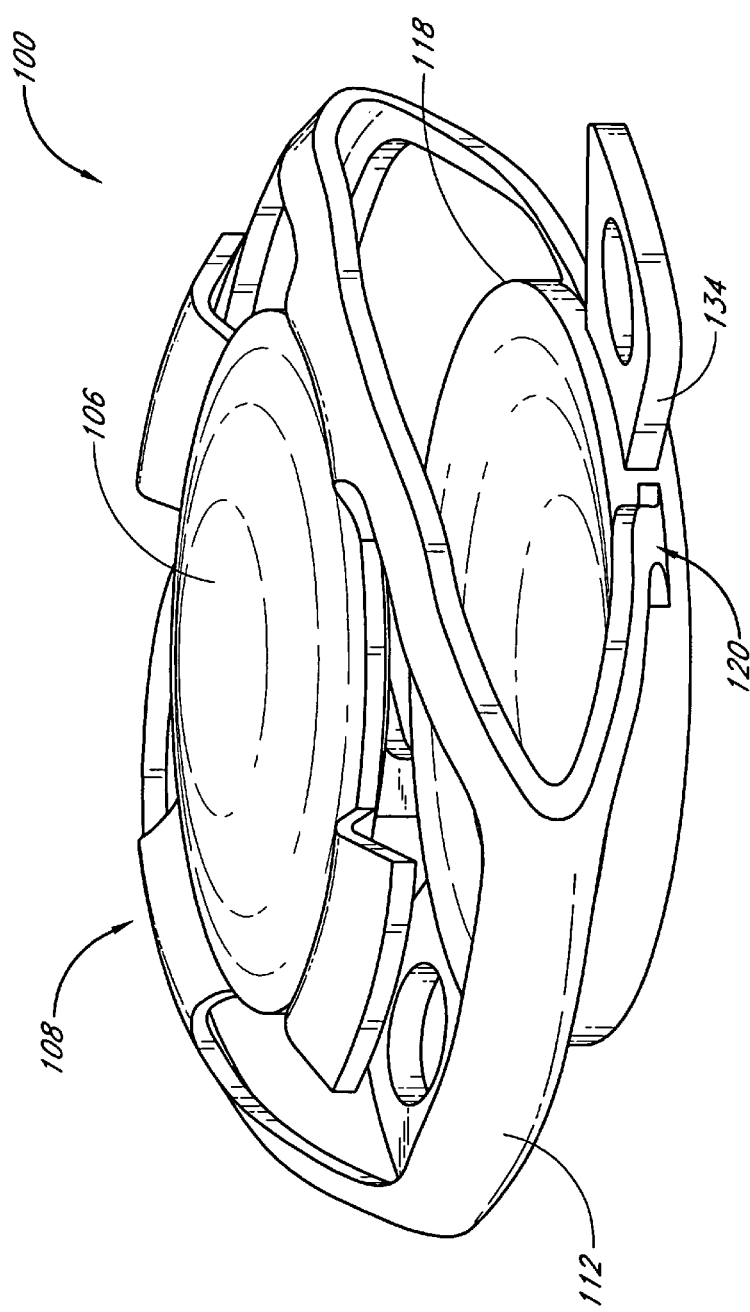
FIG. 11 is a second perspective view of the lens system.
Figure 12:
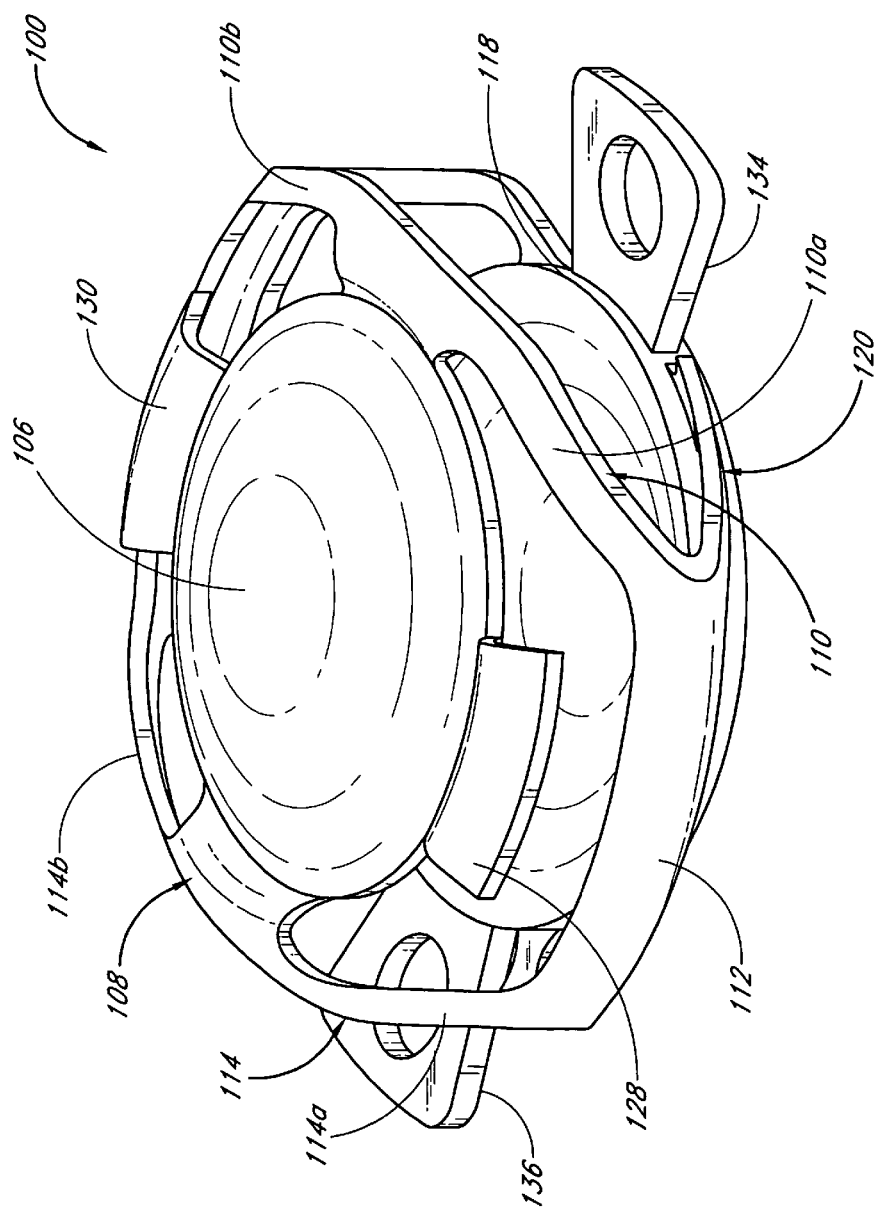
FIG. 12 is a third perspective view of the lens system.
Figure 14:
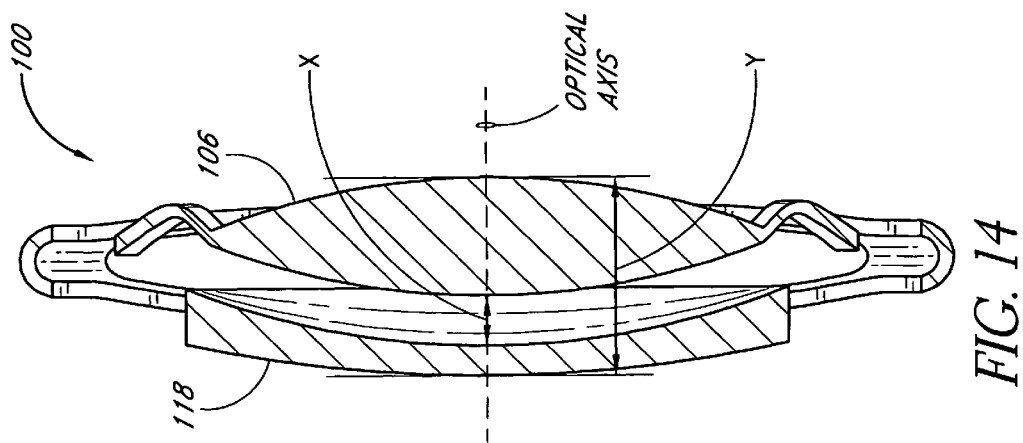
FIG. 14 is a side sectional view of the lens system in the unaccommodated state.
Figure 13:
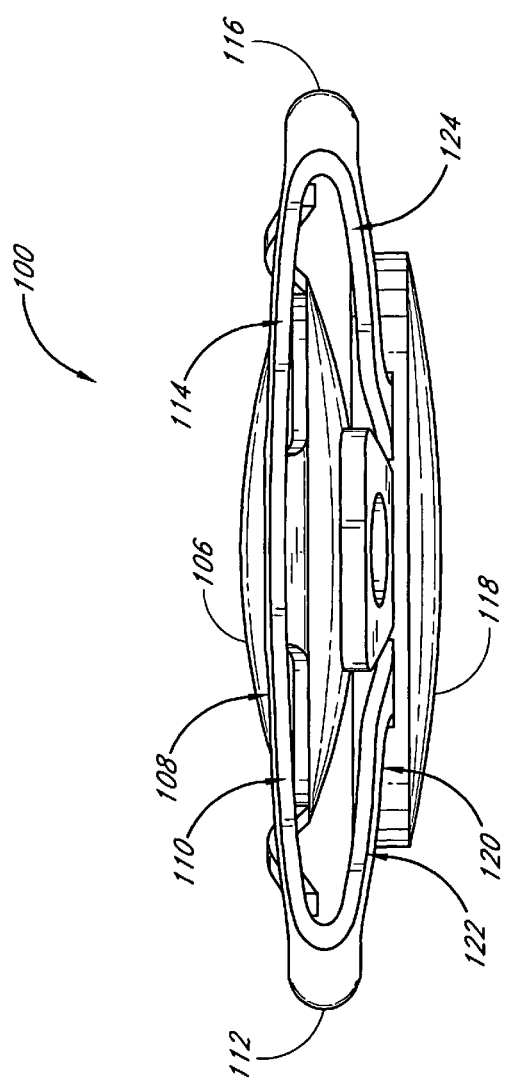
FIG. 13 is a side view of the lens system in the unaccommodated state.
Figure 15:
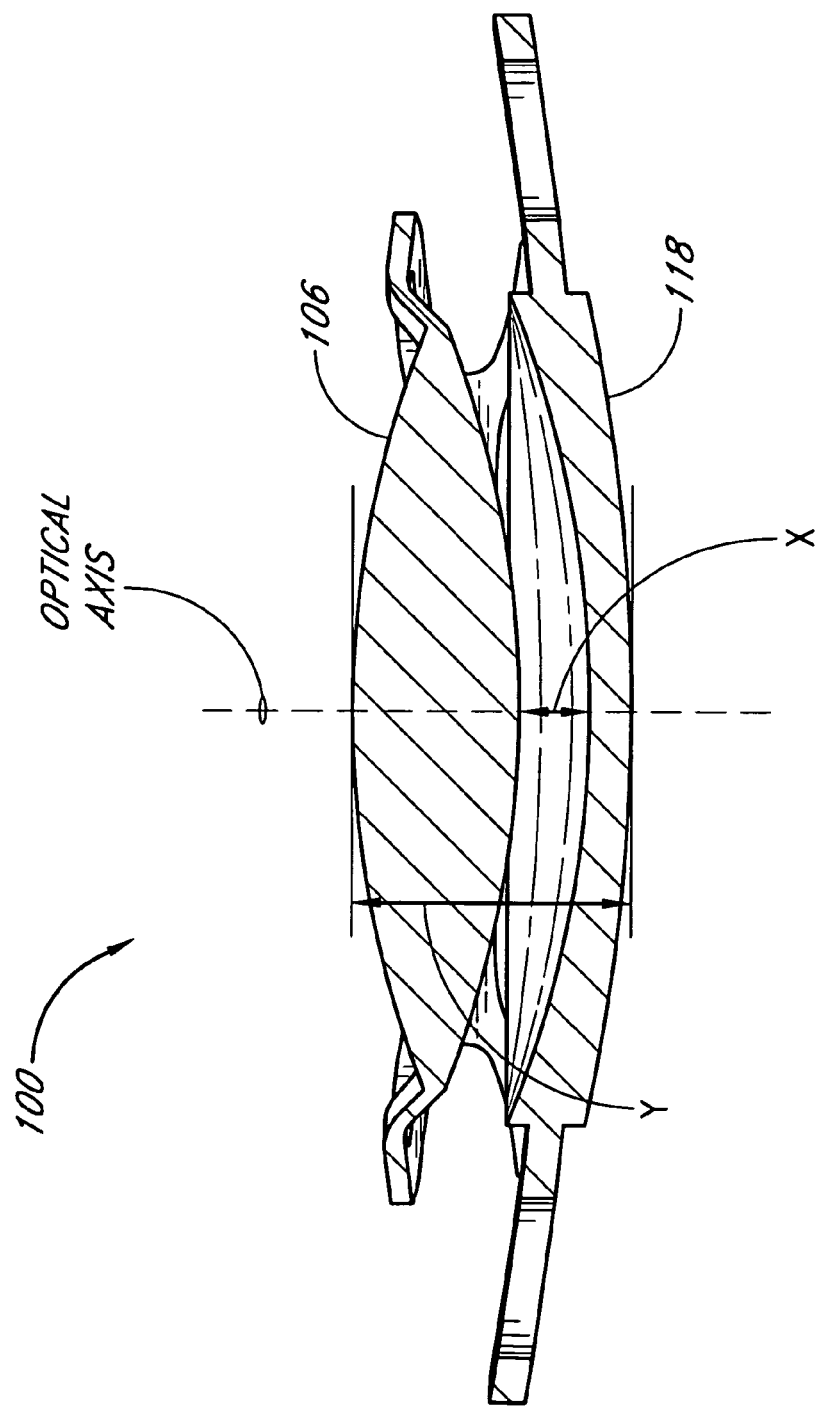
FIG. 15 is a top sectional view of the lens system in the unaccommodated state.
Figure 16:
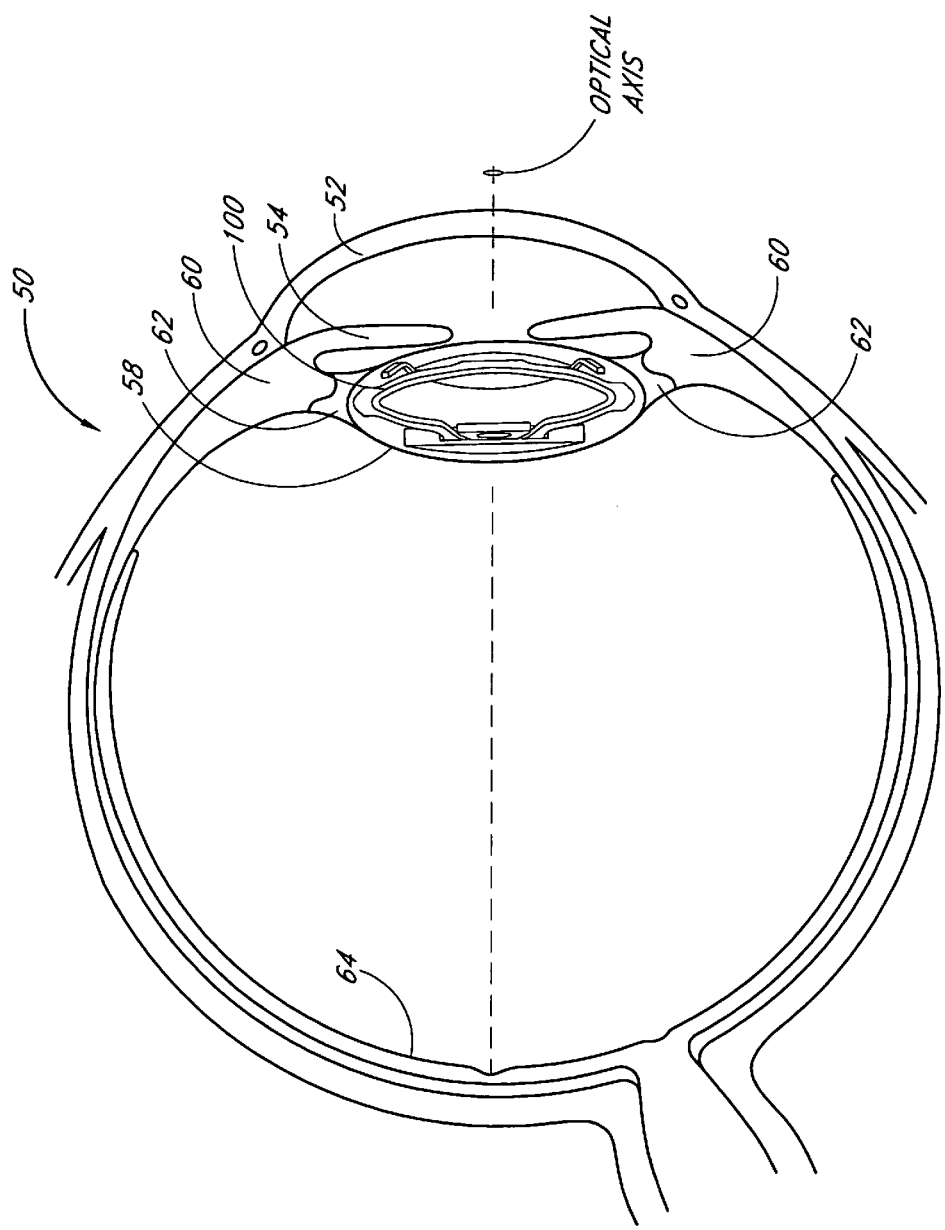
FIG. 16 is a sectional view of the human eye with the lens system implanted in the capsular bag and the lens system in the accommodated state.

As best seen in FIGS. 4, 5 and 7, the posterior portion 104 includes a posterior viewing element 118 and a posterior biasing element 120. The posterior biasing element 120 includes a first posterior translation member 122 extending from the posterior viewing element 118 to the first apex 112 and a second posterior translation member 124 extending from the posterior viewing element 118 to the second apex 116. In the illustrated embodiment, the first posterior translation member comprises a right arm 122a and a left arm 122b. Likewise, the depicted second posterior translation member 124 comprises a right arm 124a and a left arm 124b. However, in other embodiments either or both of the first and second posterior translation members 122, 124 may comprise a single arm or member, or more than two arms or members.

In the embodiment shown in FIG. 4, the anterior biasing element 108 and the posterior biasing element are configured symmetrically with respect to the plane A-A as the lens system 100 is viewed from the side. As used herein to describe the biasing elements 108, 120, "symmetric" or "symmetrically" means that, as the lens system 100 is viewed from the side, the first anterior translation member 110 and the first posterior translation member 122 extend from the first apex 112 at substantially equal first anterior and posterior biasing angles $\theta_1$, $\theta_2$ with respect to the line A-A (which, again, represents the edge of a plane which is substantially orthogonal to the optical axis and intersects the first and second apices 112, 116) and/or that the second anterior translation member 114 and the second posterior translation member 124 extend from the second apex 116 at substantially equal second anterior and posterior biasing angles $\theta_3$, $\theta_4$ with respect to the line A-A. Alternative or asymmetric configurations of the biasing elements are possible, as will be discussed in further detail below. It should be further noted that a symmetric configuration of the biasing elements 108, 120 does not dictate symmetric positioning of the viewing elements with respect to the line A-A; in the embodiment shown in FIG. 4 the anterior viewing element 106 is closer to the line A-A than is the posterior viewing element.

Preferably, both the anterior viewing element 106 and the posterior viewing element 118 comprise an optic or lens having refractive power. (As used herein, the term "refractive" or "refractive power" shall include "diffractive" or "diffractive power".) The preferred power ranges for the optics are discussed in detail below. In alternative embodiments one or both of the anterior and posterior viewing elements 106, 118 may comprise an optic with a surrounding or partially surrounding perimeter frame member or members, with some or all of the biasing elements/translation members attached to the frame member(s). As a further alternative, one of the viewing elements 106, 118 may comprise a perimeter frame with an open/empty central portion or void located on the optical axis (see FIG. 20 and discussion below), or a perimeter frame member or members with a zero-power lens or transparent member therein. In still further variations, one of the viewing elements 106, 118 may comprise only a zero-power lens or transparent member.

In a presently preferred embodiment, a retention portion 126 is coupled to the anterior portion 102, preferably at the anterior viewing element 106. The retention portion 126 preferably includes a first retention member 128 and a second retention member 130, although in alternative embodiments the retention portion 126 may be omitted altogether, or may comprise only one retention member or more than two retention members. The first retention member 128 is coupled to the anterior viewing element 106 at a fixed end 128a and also includes a free end 128b opposite the fixed end 128a. Likewise, the second retention member 130 includes a fixed end 130a and a free end 130b. The retention members 128, 130 are illustrated as being coupled to the anterior viewing element 106 at the upper and lower edges thereof; however, the retention members 128, 130 may alternatively be attached to the anterior viewing element 106 at other suitable edge locations.

In the preferred embodiment, the posterior portion 104 includes a distending portion 132, preferably attached to the posterior viewing element 118. The preferred distending portion 132 includes a first distending member 134 which in turn includes a fixed end 134a, a free end 134b opposite the fixed end 134a and preferably also includes an opening 134c formed therein. The preferred distending portion 132 also comprises a second distending member 136 with a fixed end 136a, a free end 136b and preferably an opening 136c formed therein. In alternative embodiments, the distending portion 132 may be omitted altogether, or may comprise a single distending member or more than two distending members. To optimize their effectiveness, the preferred location for the distending members 134, 136 is 90 degrees away (about the optical axis) from the apices 112, 116 on the posterior portion 104. Where the biasing elements form more than two apices (or where two apices are not spaced 180 degrees apart about the optical axis), one or more distending members may be positioned angularly midway between the apices about the optical axis. Alternatively, the distending member(s) may occupy other suitable positions relative to the apices (besides the "angularly midway" positions disclosed above); as further alternatives, the distending member(s) may be located on the anterior portion 102 of the lens system 100, or even on the apices themselves. The functions of the retention portion 126 and the distending portion 132 will be described in greater detail below.

III. The Lens System: Function/Optics

The anterior and posterior biasing elements 108, 120 function in a springlike manner to permit the anterior viewing element 106 and posterior viewing element 118 to move relative to each other generally along the optical axis. The biasing elements 108, 120 bias the viewing elements 106, 118 apart so that the elements 106, 108 separate to the accommodated position or accommodated state shown in FIG. 4. Thus, in the absence of any external forces, the viewing elements are at their maximum separation along the optical axis. The viewing elements 106, 118 of the lens system 100 may be moved toward each other, in response to a ciliary muscle force of up to 2 grams, to provide an unaccommodated position by applying appropriate forces upon the anterior and posterior portions 102, 104 and/or the apices 112, 116.

When the lens system 100 is implanted in the capsular bag 58 (FIGS. 16-17) the above described biasing forces cause the lens system 100 to expand along the optical axis so as to interact with both the posterior and anterior aspects of the capsular bag. Such interaction occurs throughout the entire range of motion of the ciliary muscle 60. At one extreme the ciliary muscle is relaxed and the zonules 62 pull the capsular bag 58 radially so as to cause the bag to become more disk shaped. The anterior and posterior sides of the bag, in turn, apply force to the anterior and posterior portions 102, 104 of the lens system 100, thereby forcing the viewing elements 106, 118 toward each other into the accommodated position. At the other extreme, the ciliary muscle contracts and the zonules 62 move inwardly to provide slack in the capsular bag 58 and allow the bag to become more football-shaped. The slack in the bag is taken up by the lens system due to the biasing-apart of the anterior and posterior viewing elements 106, 118. As the radial tension in the bag is reduced, the viewing elements 106, 118 move away from each other into an accommodated position. Thus, the distance between the viewing elements 106, 118 depends on the degree of contraction or relaxation of the ciliary muscle 60. As the distance between the anterior and posterior viewing elements 106, 118 is varied, the focal length of the lens system 100 changes accordingly. Thus, when the lens system 100 is implanted into the capsular bag (see FIGS. 16-17) the lens system 100 operates in conjunction with the natural accommodation processes of the eye to move between the accommodated (FIG. 16) and unaccommodated (FIG. 17) states in the same manner as would a healthy "natural" lens. Preferably, the lens system 100 can move between the accommodated and unaccommodated states in less than about one second.

The entire lens system 100, other than the optic(s), thus comprises an articulated frame whose functions include holding the optic(s) in position within the capsular bag and guiding and causing movement of the optic(s) between the accommodated and unaccommodated positions.

Advantageously, the entire lens system 100 may comprise a single piece of material, i.e. one that is formed without need to assemble two or more components by gluing, heat bonding, the use of fasteners or interlocking elements, etc. This characteristic increases the reliability of the lens system 100 by improving its resistance to material fatigue effects which can arise as the lens system experiences millions of accommodation cycles throughout its service life. It will be readily appreciated that the molding process and mold tooling discussed herein, lend themselves to the molding of lens systems 100 that comprise a single piece of material. However, any other suitable technique may be employed to manufacture single-piece lens systems.

In those embodiments where the optic(s) are installed into annular or other perimeter frame member(s) (see discussion below), the articulated frame may comprise a single piece of material, to obtain the performance advantages discussed above. It is believed that the assembly of the optic(s) to the articulated frame will not substantially detract from the achievement of these advantages.

The lens system 100 has sufficient dynamic range that the anterior and posterior viewing elements 106, 118 move about 0.54 mm, preferably about 1-3 mm, more preferably about 1-2 mm, and most preferably about 1.5 mm closer together when the lens system 100 moves from the accommodated state to the unaccommodated state. In other words the separation distance X (see FIGS. 9-10, 14-15) between the anterior and posterior viewing elements 106, 118, which distance may for present purposes be defined as the distance along the optical axis (or a parallel axis) between a point of axial intersection with the posterior face of the anterior viewing element 106 and a point of axial intersection with the anterior face of the posterior viewing element 118, decreases by the amount(s) disclosed above upon movement of the lens system 100 to the unaccommodated state. Simultaneously, in the preferred mode the total system thickness Y decreases from about 3.0-4.0 mm in the accommodated state to about 1.5-2.5 mm in the unaccommodated state.

Figure 6:
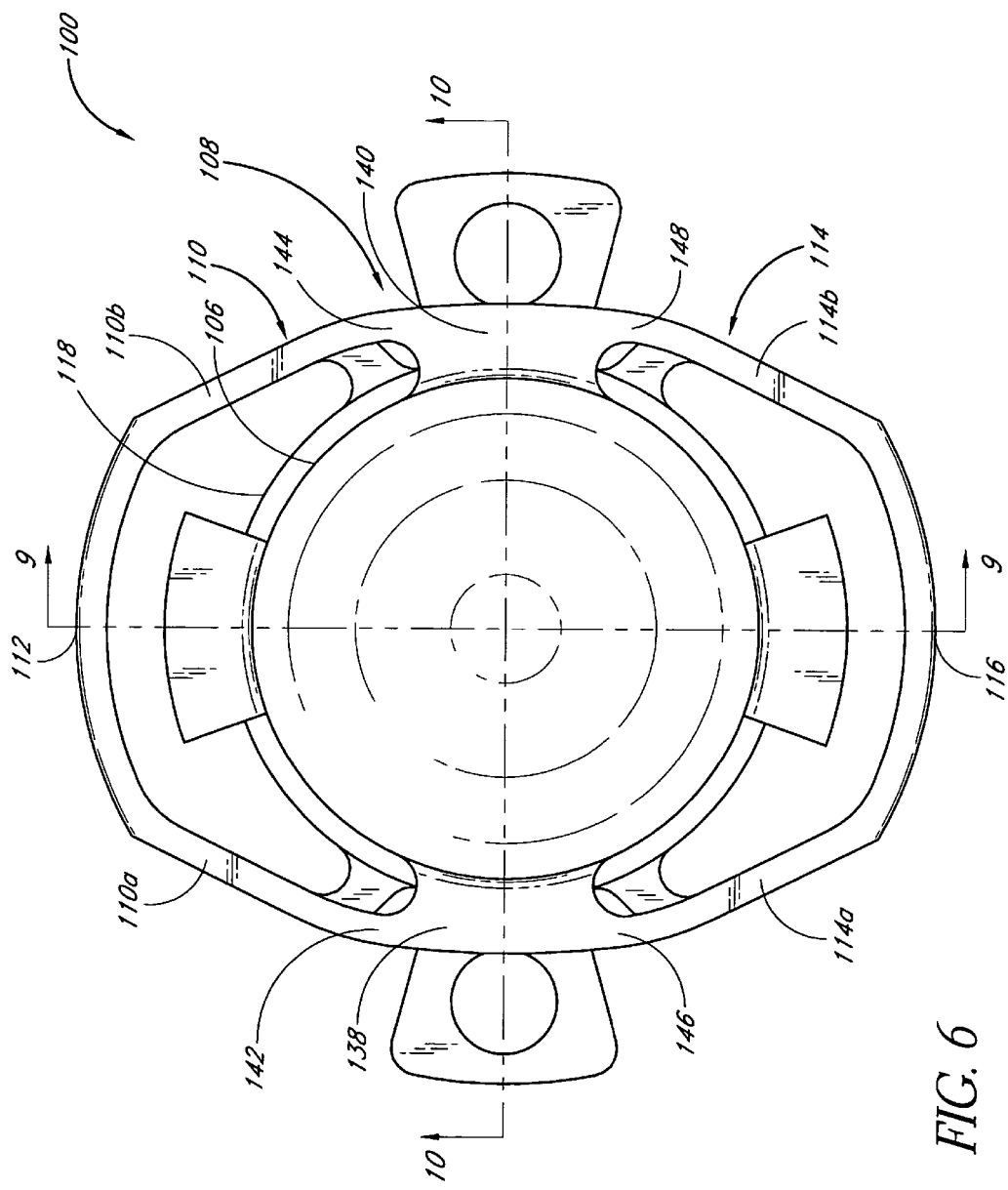
FIG. 6 is a front view of the lens system.

As may be best seen in FIG. 6, the first anterior translation member 110 connects to the anterior viewing element 106 via connection of the left and right arms 110a, 110b to first and second transition members 138, 140 at attachment locations 142, 144. The second anterior translation member 114 connects to the anterior viewing element 106 via connection of left and right arms 114a, 114b to the first and second transition members 138, 140 at attachment locations 146, 148. This is a presently preferred arrangement for the first and second anterior translation members 110, 114; alternatively, the first and second anterior translation members 110, 114 could be connected directly to the anterior viewing element 106, as is the case with the connection of the first and second posterior translation members 122, 124 to the posterior viewing element 118.

However the connection is established between the first and second anterior translation members 110, 114 and the anterior viewing element 106, it is preferred that the attachment locations 142, 144 corresponding to the first anterior translation member 110 be farther away from the first apex 112 than is the closest edge or the periphery of the anterior viewing element 106. This configuration increases the effective length of the first anterior translation member 110/arms 110a, 110b, in comparison to a direct or straight attachment between the apex 112 and the nearest/top edge of the anterior viewing element 106. For the same reasons, it is preferred that the attachment locations 146, 148 associated with the second anterior translation member 114 be farther away from the second apex 116 than is the closest/bottom edge of the anterior viewing element 106.

As best seen in FIG. 7, the first posterior translation member 122 is preferably connected directly to the posterior viewing element 118 via attachment of the left and right arms 122a, 122b to the element 118 at attachment points 150, 152. Likewise, the second posterior translation member 124 is preferably directly connected to the posterior viewing element 118 via connection of the left and right arms 124a, 124b to the element 118 at attachment points 154, 156, respectively. In alternative embodiments, the first and second posterior translation members 124, 122 can be connected to the posterior viewing element via intervening members as is done with the anterior viewing element 106. No matter how these connections are made, it is preferred that the attachment locations 150, 152 be spaced further away from the first apex 112 than is the nearest edge or the periphery of the posterior viewing element 118. Similarly, it is preferred that the attachment locations 154, 156 be spaced further away from the second apex 116 than is the closest edge of the posterior viewing element 118.

By increasing the effective length of some or all of the translation members 110, 114, 122, 124 (and that of the arms 110*a*, 110*b*, 114*a*, 114*b*, 122*a*, 122*b*, 124*a*, 124*b* where such structure is employed), the preferred configuration of the attachment locations 142, 144, 146, 148, 150, 152, 154, 156 relative to the first and second apices 112, 116 enables the anterior and/or posterior viewing elements 106, 118 to move with respect to one another a greater distance along the optical axis, for a given angular displacement of the anterior and/or posterior translation members. This arrangement thus facilitates a more responsive spring system for the lens system 100 and minimizes material fatigue effects associated with prolonged exposure to repeated flexing.

In the illustrated embodiment, the attachment location 142 of the first anterior translation member 110 is spaced from the corresponding attachment location 146 of the second anterior translation member 114 along the periphery of the anterior viewing element, and the same relationship exists between the other pairs of attachment locations 144, 148; 150, 154; and 152, 156. This arrangement advantageously broadens the support base for the anterior and posterior viewing elements 106, 118 and prevents them from twisting about an axis parallel to the lateral axis, as the viewing elements move between the accommodated and unaccommodated positions.

It is also preferred that the attachment locations 142, 144 of the first anterior translation member 110 be located equidistant from the first apex 112, and that the right and left arms 110*a*, 110*b* of the member 110 be equal in length. Furthermore, the arrangement of the attachment locations 146, 148, arms 114*a*, 114*b* and second apex preferably mirrors that recited above regarding the first anterior translation member 110, while the apices 112, 116 are preferably equidistant from the optical axis and are situated 180 degrees apart. This configuration maintains the anterior viewing element 106 orthogonal to the optical axis as the viewing element 106 moves back and forth and the anterior viewing element flexes.

For the same reasons, a like combination of equidistance and equal length is preferred for the first and second posterior translation members 122, 124 and their constituent arms 122*a*, 122*b*, 124*a*, 124*b* and attachment points 150, 152, 154, 156, with respect to the apices 112, 116. However, as shown the arms 122*a*, 122*b*, 124*a*, 124*b* need not be equal in length to their counterparts 110*a*, 110*b*, 114*a*, 114*b* in the first and second anterior translation members 110, 114.

Where any member or element connects to the periphery of the anterior or posterior viewing elements 106, 118, the member defines a connection geometry or attachment area with a connection width W and a connection thickness T (see FIG. 4 and the example illustrated therein, of the connection of the second posterior translation member 124 to the posterior viewing element 118). For purposes of clarity, the connection width is defined as being measured along a direction substantially parallel to the periphery of the viewing element in question, and the connection thickness is defined as measured along a direction substantially perpendicular to the periphery of the viewing element. (The periphery itself is deemed to be oriented generally perpendicular to the optical axis as shown in FIG. 4.) Preferably, no attachment area employed in the lens system 100 has a ratio of width to thickness less than 3. It has been found that such a geometry reduces distortion of the viewing element/optic due to localized forces. For the same reasons, it is also preferred that each of the translation members 110, 114, 122, 124 be connected to the periphery of the respective viewing elements at least two attachment areas, each having the preferred geometry discussed above.

Figure 17:
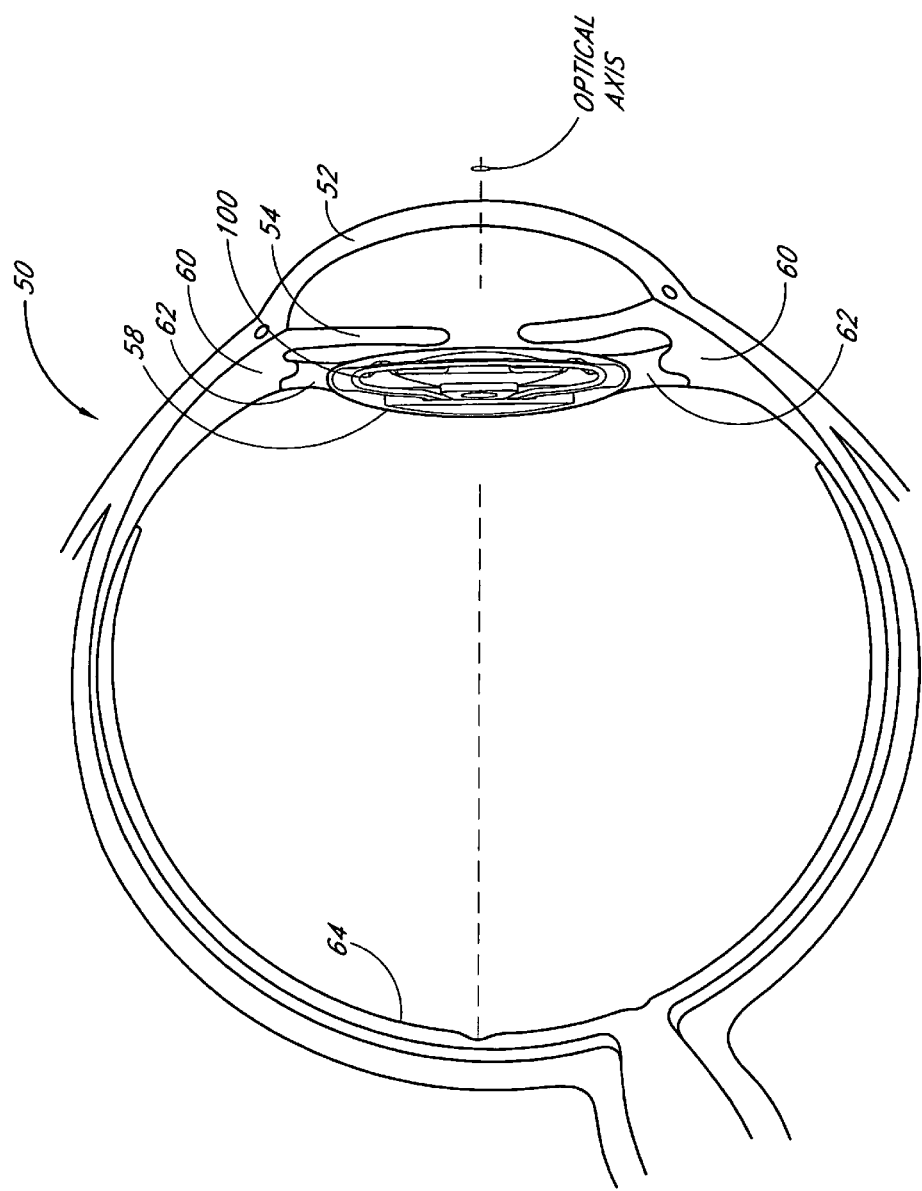
FIG. 17 is a sectional view of the human eye with the lens system implanted in the capsular bag and the lens system in the unaccommodated state.
Figure 17A:
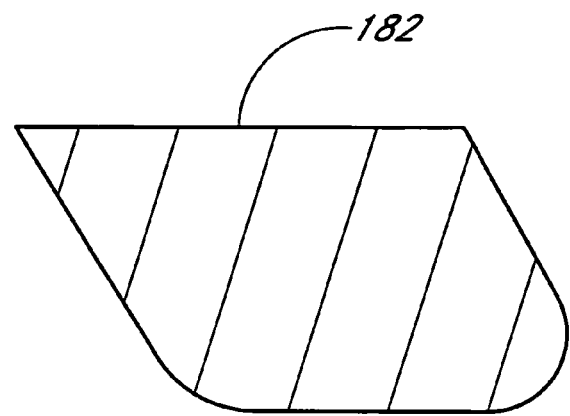
FIG. 17A is a sectional view of an arm of the lens system.
Figure 17B:
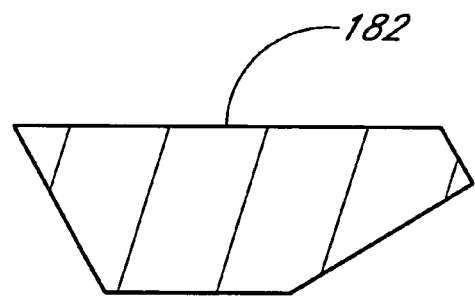
FIG. 17B is a sectional view of another embodiment of the arm of the lens system.

FIGS. 17A and 17B show two preferred cross-sectional configurations which may be used along some or all of the length of the translation members and/or arms 110*a*, 110*b*, 114*a*, 114*b*, 122*a*, 122*b*, 124*a*, 124*b*. The shape is defined by a relatively broad and flat or slightly curved outer surface 182. It is intended that when in use the outer surface faces away from the interior of the lens system and/or toward the capsular bag 58. The remaining surfaces, proportions and dimensions making up the cross-sectional shape can vary widely but may advantageously be selected to facilitate manufacture of the lens system 100 via molding or casting techniques while minimizing stresses in the arms during use of the lens system.

FIGS. 17.C-17L depict a number of alternative cross-sectional configurations which are suitable for the translation members and/or arms 110*a*, 110*b*, 114*a*, 114*b*, 122*a*, 122*b*, 124*a*, 124*b*. As shown, a wide variety of cross-sectional shapes may be used, but preferably any shape includes the relatively broad and flat or slightly curved outer surface 182.

It is further contemplated that the dimensions, shapes, and/or proportions of the cross-sectional configuration of the translation members and/or arms 110*a*, 110*b*, 114*a*, 114*b*, 122*a*, 122*b*, 124*a*, 124*b* may vary along the length of the members/arms. This may be done in order to, for example, add strength to high-stress regions of the arms, fine-tune their spring characteristics, add rigidity or flexibility, etc.

As discussed above, each of the anterior viewing element 106 and the posterior viewing element 118 preferably comprises an optic having refractive power. In one preferred embodiment, the anterior viewing element 106 comprises a biconvex lens having positive refractive power and the posterior viewing element 118 comprises a convexo-concave lens having negative refractive power. The anterior viewing element 106 may comprise a lens having a positive power advantageously less than 55 diopters, preferably less than 40 diopters, more preferably less than 35 diopters, and most preferably less than 30 diopters. The posterior viewing element 118 may comprise a lens having a power which is advantageously between −25 and 0 diopters, and preferably between −25 and −15 diopters. In other embodiments, the posterior viewing element 118 comprises a lens having a power which is between −15 and 0 diopters, preferably between −13 and −2 diopters, and most preferably between −10 and −5 diopters. Advantageously, the total power of the optic(s) employed in the lens system 100 is about 5-35 diopters; preferably, the total power is about 10-30 diopters; most preferably, the total power is about 15-25 diopters. (As used herein, the term "diopter" refers to lens or system power as measured when the lens system 100 has been implanted in the human eye in the usual manner.) It should be noted that if materials having a high index of refraction (e.g., higher than that of silicone) are used, the optics may be made thinner which facilitates a wider range of motion for the optics. This in turn allows the use of lower-power optics than those specified above. In addition, higher-index materials allow the manufacture of a higher-power lens for a given lens thickness and thereby reduce the range of motion needed to achieve a given range of accommodation.

Some lens powers and radii of curvature presently preferred for use with an embodiment of the lens system 100 with optic(s) having a refractive index of about 1.432 are as follows: a +31 diopter, biconvex lens with an anterior radius of curvature of 5.944 mm and a posterior radius of curvature of 5.944 mm; a +28 diopter, biconvex lens with an anterior radius of curvature of 5.656 mm and a posterior radius of curvature of 7.788 mm; a +24 diopter, biconvex lens with an anterior radius of curvature of 6.961 mm and a posterior radius of curvature of 8.5 mm; a −10 diopter, biconcave lens with an anterior radius of curvature of 18.765 mm and a posterior radius of curvature of 18.765 mm; a −8 diopter, concavo-convex lens with an anterior radius of curvature of between 9 mm and 9.534 mm and a posterior radius of curvature of 40 mm; and a −5 diopter, concavo-convex lens with an anterior radius of curvature of between 9 mm and 9.534 mm and a posterior radius of curvature of 20 mm. In one embodiment, the anterior viewing element comprises the +31 diopter lens described above and the posterior viewing element comprises the −10 diopter lens described above. In another embodiment, the anterior viewing element comprises the +28 diopter lens described above and the posterior viewing element comprises the −8 diopter lens described above. In another embodiment, the anterior viewing element comprises the +24 diopter lens described above and the posterior viewing element comprises the −5 diopter lens described above.

The combinations of lens powers and radii of curvature specified herein advantageously minimize image magnification. However, other designs and radii of curvature provide modified magnification when desirable.

The lenses of the anterior viewing element 106 and the posterior viewing element 118 are relatively moveable as discussed above; advantageously, this movement is sufficient to produce an accommodation of at least one diopter, preferably at least two diopters and most preferably at least three diopters. In other words, the movement of the optics relative to each other and/or to the cornea is sufficient to create a difference between (i) the refractive power of the user's eye in the accommodated state and (ii) the refractive power of the user's eye in the unaccommodated state, having a magnitude expressed in diopters as specified above. Where the lens system 100 has a single optic, the movement of the optic relative to the cornea is sufficient to create a difference in focal power as specified above.

Advantageously, the lens system 100 can be customized for an individual patient's needs by shaping or adjusting only one of the four lens faces, and thereby altering the overall optical characteristics of the system 100. This in turn facilitates easy manufacture and maintenance of an inventory of lens systems with lens powers which will fit a large population of patients, without necessitating complex adjustment procedures at the time of implantation. It is contemplated that all of the lens systems in the inventory have a standard combination of lens powers, and that a system is fitted to a particular patient by simply shaping only a designated "variable" lens face. This custom-shaping procedure can be performed to-order at a central manufacturing facility or laboratory, or by a physician consulting with an individual patient. In one embodiment, the anterior face of the anterior viewing element is the designated sole variable lens face. In another embodiment, the anterior face of the posterior viewing element is the only variable face. However, any of the lens faces is suitable for such designation. The result is minimal inventory burden with respect to lens power (all of the lens systems in stock have the same lens powers) without requiring complex adjustment for individual patients (only one of the four lens faces is adjusted in the fitting process).

IV. The Lens System: Alternative Embodiments

Figure 17M:
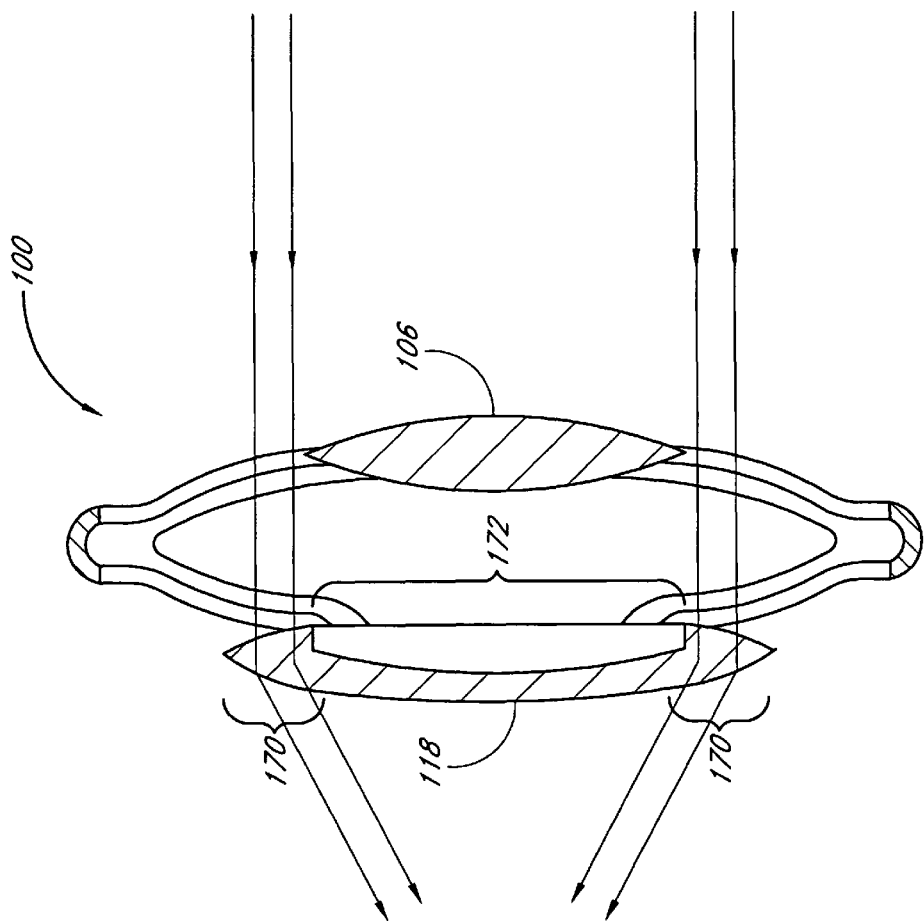
FIG. 17M is a side sectional view of another embodiment of the lens system.

FIG. 17M depicts another embodiment of the lens system 100 in which the anterior viewing element 106 comprises an optic with a smaller diameter than the posterior viewing element 118, which comprises an optic with a peripheral positive-lens portion 170 surrounding a central negative portion 172. This arrangement enables the user of the lens system 100 to focus on objects at infinity, by allowing the (generally parallel) light rays incident upon the eye from an object at infinity to bypass the anterior viewing element 106. The peripheral positive-lens portion 170 of the posterior viewing element 118 can then function alone in refracting the light rays, providing the user with focused vision at infinity (in addition to the range of visual distances facilitated by the anterior and posterior viewing elements acting in concert). In another embodiment, the anterior viewing element 106 comprises an optic having a diameter of approximately 3 millimeters or less. In yet another embodiment, the anterior viewing element 106 comprises an optic having a diameter of approximately 3 millimeters or less and a refractive power of less than 55 diopters, more preferably less than 30 diopters. In still another embodiment, the peripheral positive-lens portion 170 has a refractive power of about 20 diopters.

Figure 17N:
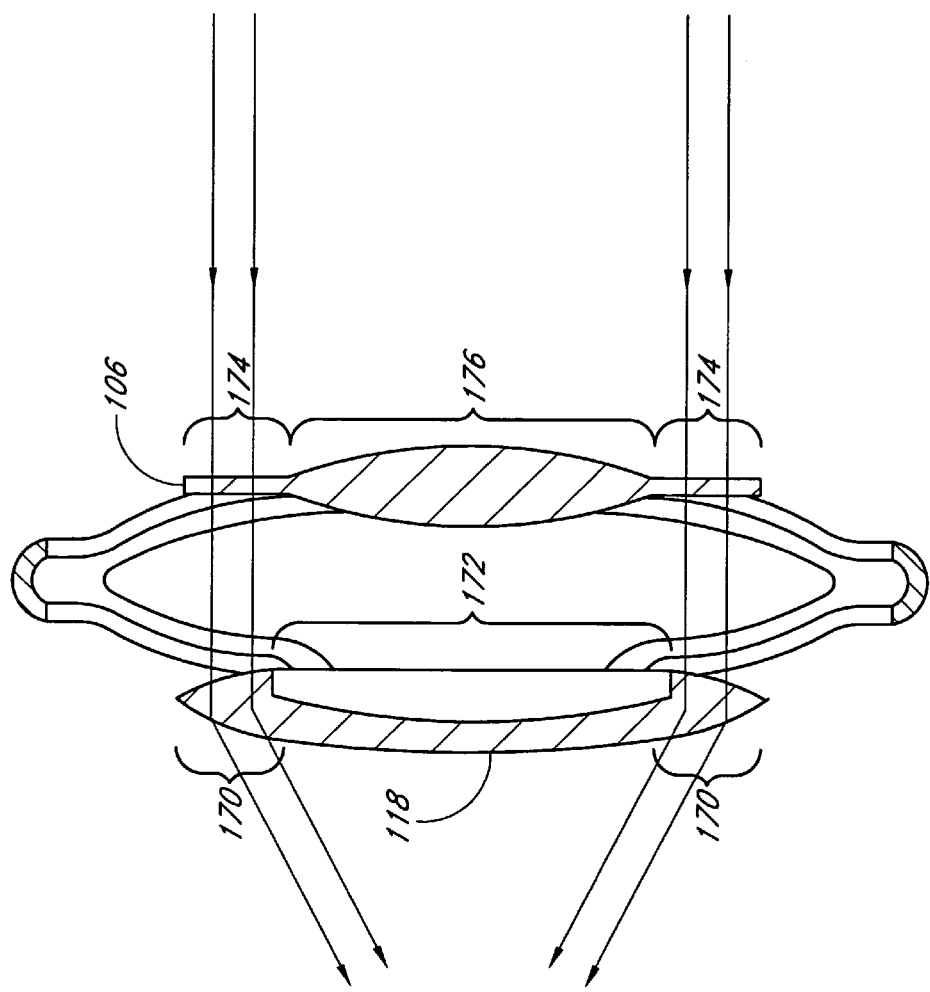
FIG. 17N is a side sectional view of another embodiment of the lens system.

FIG. 17N shows an alternative arrangement in which, the anterior viewing element 106 comprises an optic having a central portion 176 with refractive power, and a surrounding peripheral region 174 having a refractive power of substantially zero, wherein the central region 176 has a diameter smaller than the optic of the posterior viewing element 118, and preferably has a diameter of less than about 3 millimeters. This embodiment also allows some incident light rays to pass the anterior viewing element (though the zero-power peripheral region 174) without refraction, allowing the peripheral positive-lens portion 170 posterior viewing element 118 to function alone as described above.

Figure 18:
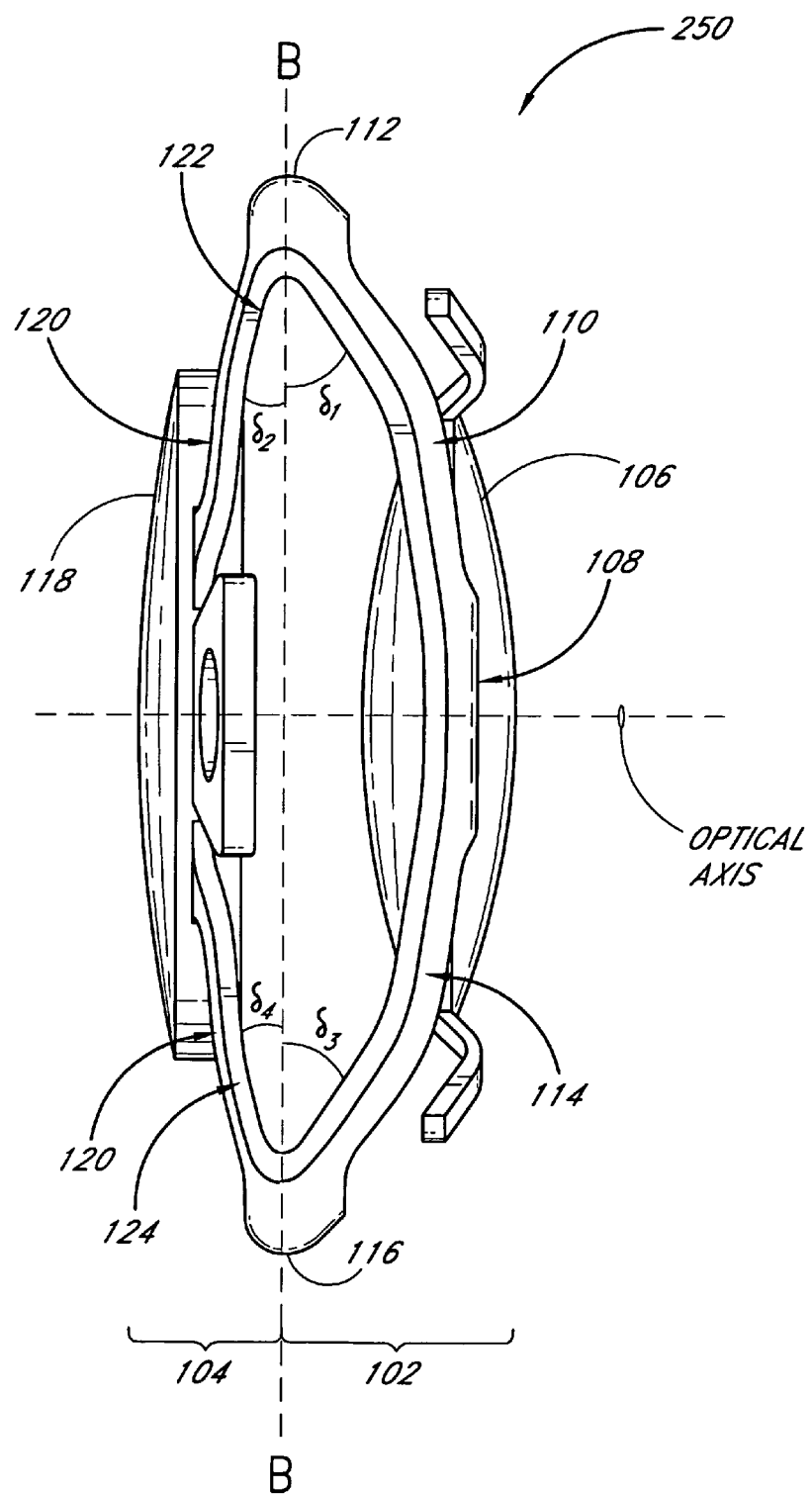
FIG. 18 is a side view of another embodiment of the lens system.
Figure 19:
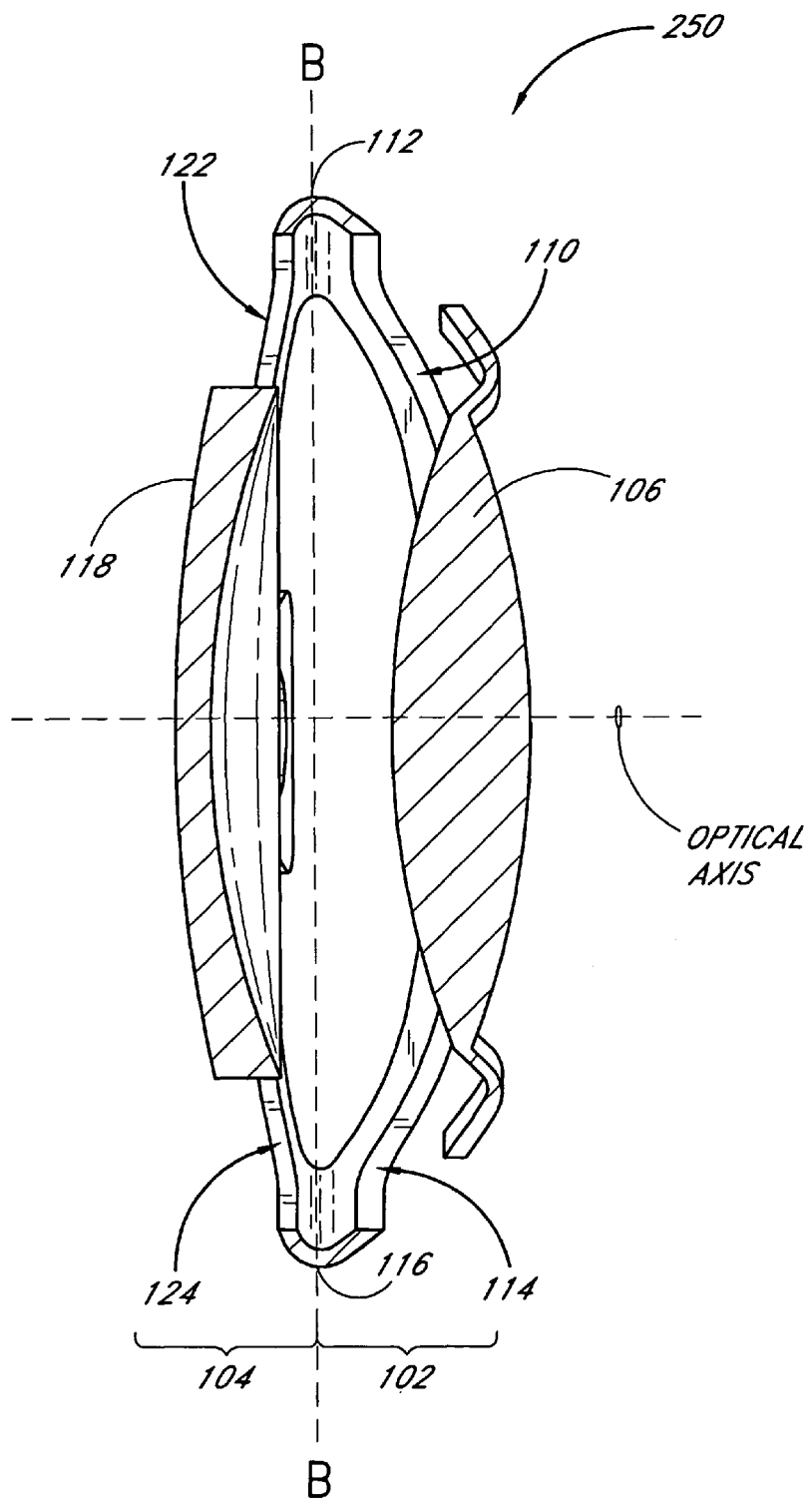
FIG. 19 is a side sectional view of another embodiment of the lens system.

FIGS. 18 and 19 depict another embodiment 250 of the intraocular lens. It is contemplated that, except as noted below, this embodiment 250 is largely similar to the embodiment disclosed in FIGS. 3-17. The lens 250 features an anterior biasing element 108 and posterior biasing element 120 which are arranged asymmetrically as the lens system 100 is viewed from the side. As used herein to describe the biasing elements 108, 120, "asymmetric" or "asymmetrically" means that, as the lens system 100 is viewed from the side, the first anterior translation member 110 and the first posterior translation member 122 extend from the first apex 112 at unequal first anterior and posterior biasing angles $\delta_1$, $\delta_2$ with respect to the line B-B (which represents the edge of a plane which is substantially orthogonal to the optical axis and intersects the first and second apices 112, 116) and/or that the second anterior translation member 114 and the second posterior translation member 124 extend from the second apex 116 at unequal second anterior and posterior biasing angles $\delta_3$, $\delta_4$ with respect to the line B-B.

In the embodiment shown in FIGS. 18-19, the first and second anterior biasing angles $\delta_1$, $\delta_3$ are greater than the corresponding first and second posterior biasing angles $\delta_2$, $\delta_4$. This arrangement advantageously maintains the posterior viewing element 118 and apices 112, 116 in a substantially stationary position. Consequently, the moving mass of the lens system 250 is reduced, and the anterior viewing element 106 can move more quickly over a wider range along the optical axis under a given motive force. (Note that even where the posterior biasing element 120 and its constituent first and second posterior translation members 122, 124 are substantially immobile, they are nonetheless "biasing elements" and "translation members" as those terms are used herein.) In another embodiment, the anterior biasing element 108 and posterior biasing element 120 are arranged asymmetrically in the opposite direction, i.e. such that the first and second anterior biasing angles $\delta_1$, $\delta_3$ are smaller than the corresponding first and second posterior biasing angles $\delta_2$, $\delta_4$. This arrangement also provides for a wider range of relative movement of the viewing elements, in comparison to a "symmetric" system.

It should be further noted that the viewing elements 106, 118 shown in FIGS. 18-19 are asymmetrically positioned in that the posterior viewing element 118 is closer to the line B-B than is the anterior viewing element 106. It has been found that this configuration yields desirable performance characteristics irrespective of the configuration of the biasing elements 108, 120. In alternative embodiments, the viewing elements 106, 118 may be positioned symmetrically with respect to the line B-B, or they may be positioned asymmetrically with the anterior viewing element 106 closer to the line B-B than the posterior viewing element 118 (see FIG. 4 wherein the line in question is denoted A-A). Furthermore, the symmetry or asymmetry of the biasing elements and viewing elements can be selected independently of each other.

Figure 20:
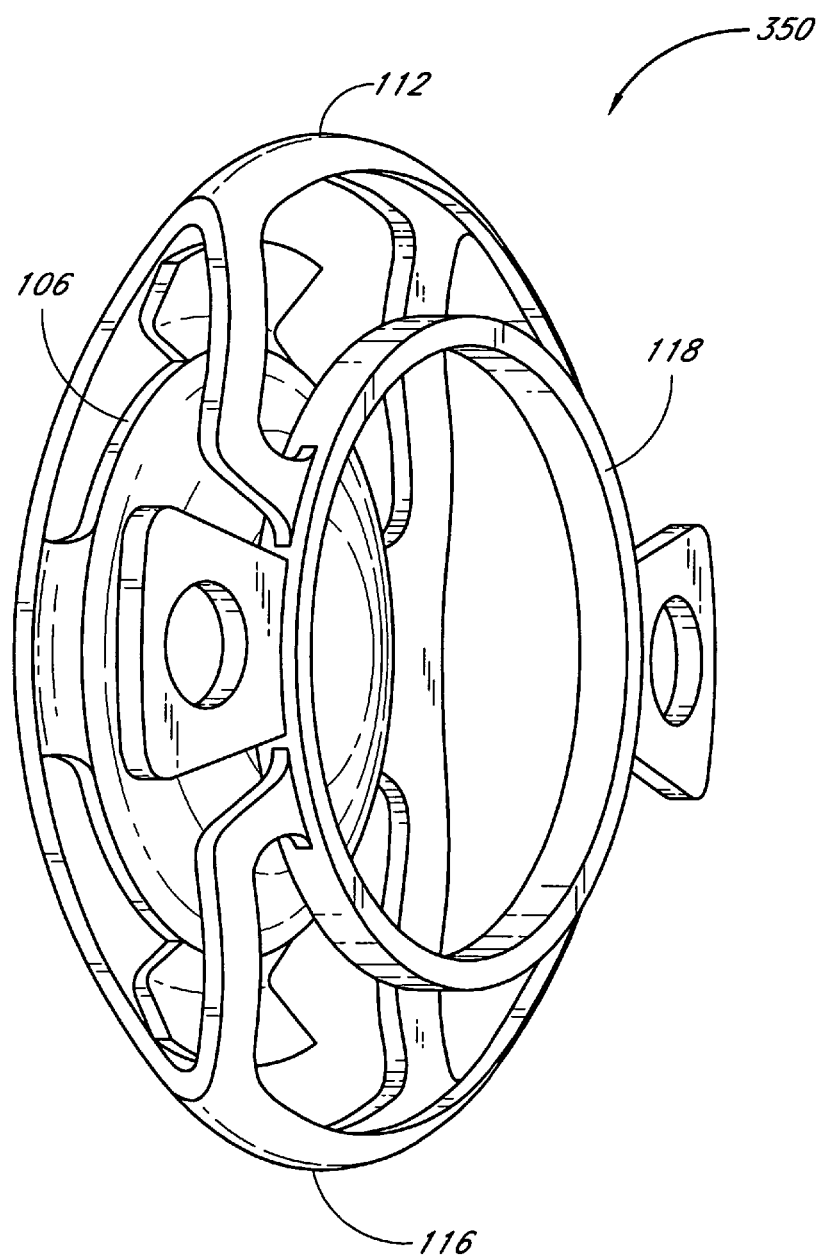
FIG. 20 is a rear perspective view of another embodiment of the lens system.

FIG. 20 shows another embodiment 350 of an intraocular lens in which the posterior viewing element 118 comprises an annular frame member defining a void therein, while the anterior viewing element 106 comprises an optic having refractive power. Alternatively, the posterior viewing element 118 could comprise a zero power lens or a simple transparent member. Likewise, in another embodiment the anterior viewing element 106 could comprise an annular frame member with a void therein or a simple zero power lens or transparent member, with the posterior viewing element 118 comprising an optic having refractive power. As a further alternative, one or both of the anterior and posterior viewing elements 106, 118 may comprise an annular or other perimeter frame member which can receive a removable optic (or a "one-time install" optic) with an interference type fit and/or subsequent adhesive or welding connections. Such a configuration facilitates assembly and/or fine-tuning of the lens system during an implantation procedure, as will be discussed in further detail below.

V. The Lens System: Additional Features

Figure 21:
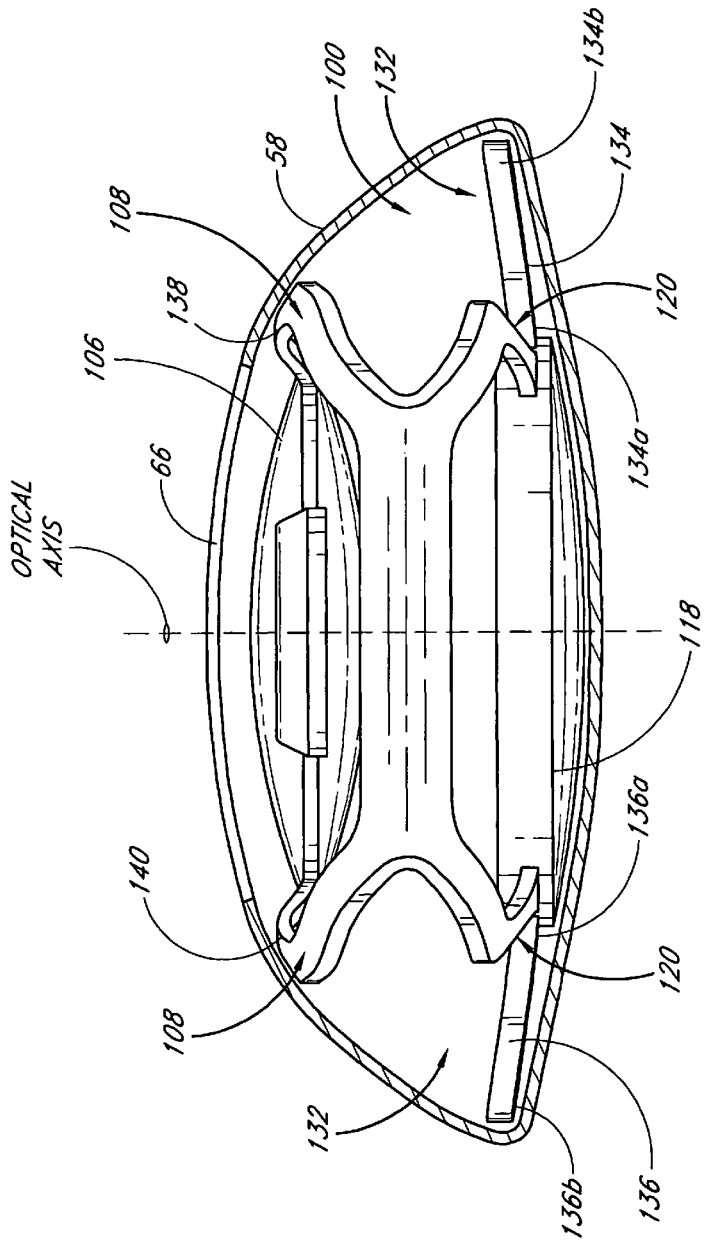
FIG. 21 is a partial top sectional view of another embodiment of the lens system, implanted in the capsular bag.

FIG. 21 depicts the function of the distending portion 132 in greater detail. The lens system 100 is shown situated in the capsular bag 58 in the customary manner with the anterior viewing element 106 and posterior viewing element 118 arranged along the optical axis. The capsular bag 58 is shown with a generally circular anterior opening 66 which may often be cut into the capsular bag during installation of the lens system 100. The first and second distending members 134, 136 of the distending portion 132 distend the capsular bag 58 so that intimate contact is created between the posterior face of the posterior viewing element and/or the posterior biasing element 120. In addition, intimate contact is facilitated between the anterior face of the anterior viewing element 106 and/or anterior biasing element 108. The distending members 134, 136 thus remove any slack from the capsular bag 58 and ensure optimum force coupling between the bag 58 and the lens system 100 as the bag 58 is alternately stretched and released by the action of the ciliary muscle.

Furthermore, the distending members 134, 136 reshape the capsular bag 58 into a taller, thinner configuration along its range of accommodation to provide a wider range of relative motion of the viewing elements 106, 118. When the capsular bag 58 is in the unaccommodated state, the distending members 134, 136 force the capsular bag into a thinner configuration (as measured along the optical axis) in comparison to the unaccommodated configuration of the capsular bag 58 with the natural lens in place. Preferably, the distending members 134, 136 cause the capsular bag 58 to taken on a shape in the unaccommodated state which is about 1.0-2.0 mm thinner, more preferably about 1.5 mm thinner, along the optical axis than it is with the natural lens in place and in the unaccommodated state.

With such a thin "starting point" provided by the distending members 134, 136, the viewing elements 106, 118 of the lens system can move a greater distance apart, and provide a greater range of accommodation, without causing undesirable contact between the lens system and the iris. Accordingly, by reshaping the bag as discussed above the distending members 134, 136 facilitate a range of relative motion of the anterior and posterior viewing elements 106, 118 of about 0.5-4 mm, preferably about 1-3 mm, more preferably about 1-2 mm, and most preferably about 1.5 mm.

The distending portion 132/distending members 134, 136 are preferably separate from the anterior and posterior biasing elements 108, 120; the distending members 134, 136 thus preferably play no part in biasing the anterior and posterior viewing elements 106, 118 apart toward the accommodated position. This arrangement is advantageous because the apices 112, 116 of the biasing elements 108, 120 reach their point of minimum protrusion from the optical axis (and thus the biasing elements reach their minimum potential effectiveness for radially distending the capsular bag) when the lens system 100 is in the accommodated state (see FIG. 16), which is precisely when the need is greatest for a taut capsular bag so as to provide immediate response to relaxation of the ciliary muscles. The preferred distending portion is "static" (as opposed to the "dynamic" biasing members 108, 120 which move while urging the viewing elements 106, 118 to the accommodated position or carrying the viewing elements to the unaccommodated position) in that its member(s) protrude a substantially constant distance from the optical axis throughout the range of motion of the viewing elements 106, 118. Although some degree of flexing may be observed in the distending members 134, 136, they are most effective when rigid. Furthermore, the thickness and/or cross-sectional profile of the distending members 134/136 may be varied over the length of the members as desired to provide a desired degree of rigidity thereto.

The distending portion 132/distending members 132, 134 advantageously reshape the capsular bag 58 by stretching the bag 58 radially away from the optical axis and causing the bag 58 to take on a thinner, taller shape throughout the range of accommodation by the eye. This reshaping is believed to facilitate a broad (as specified above) range of relative motion for the viewing elements of the lens system 100, with appropriate endpoints (derived from the total system thicknesses detailed above) to avoid the need for unacceptably thick optic(s) in the lens system.

If desired, the distending members 134, 136 may also function as haptics to stabilize and fixate the orientation of the lens system 100 within the capsular bag. The openings 134c, 136c of the preferred distending members 134,136 permit cellular ingrowth from the capsular bag upon positioning of the lens system 100 therein. Finally, other methodologies, such as a separate capsular tension ring or the use of adhesives to glue the capsular bag together in selected regions, may be used instead of or in addition to the distending portion 132, to reduce "slack" in the capsular bag.

A tension ring can also act as a physical barrier to cell growth on the inner surface of the capsular bag, and thus can provide additional benefits in limiting posterior capsule opacification, by preventing cellular growth from advancing posteriorly on the inner surface of the bag. When implanted, the tension ring firmly contacts the inner surface of the bag and defines a circumferential barrier against cell growth on the inner surface from one side of the barrier to another.

Figure 21A:
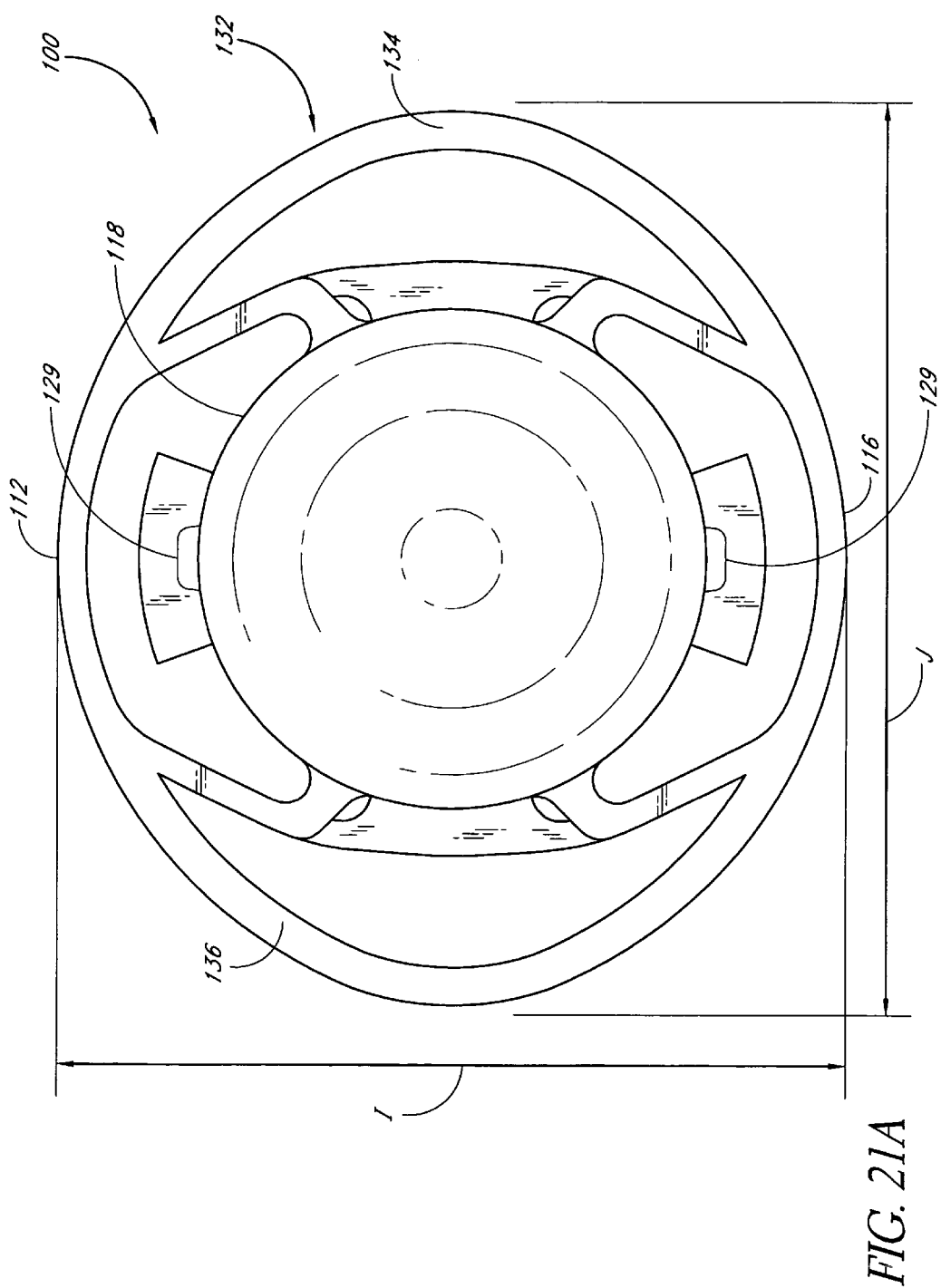
FIG. 21A is a front view of another embodiment of the lens system.

FIG. 21A shows an alternative configuration of the distending portion 132, in which the distending members 134, 136 comprise first and second arcuate portions which connect at either end to the apices 112, 116 to form therewith an integral perimeter member. In this arrangement it is preferred that the distending members and apices form an oval with height I smaller than width J.

Figure 21B:
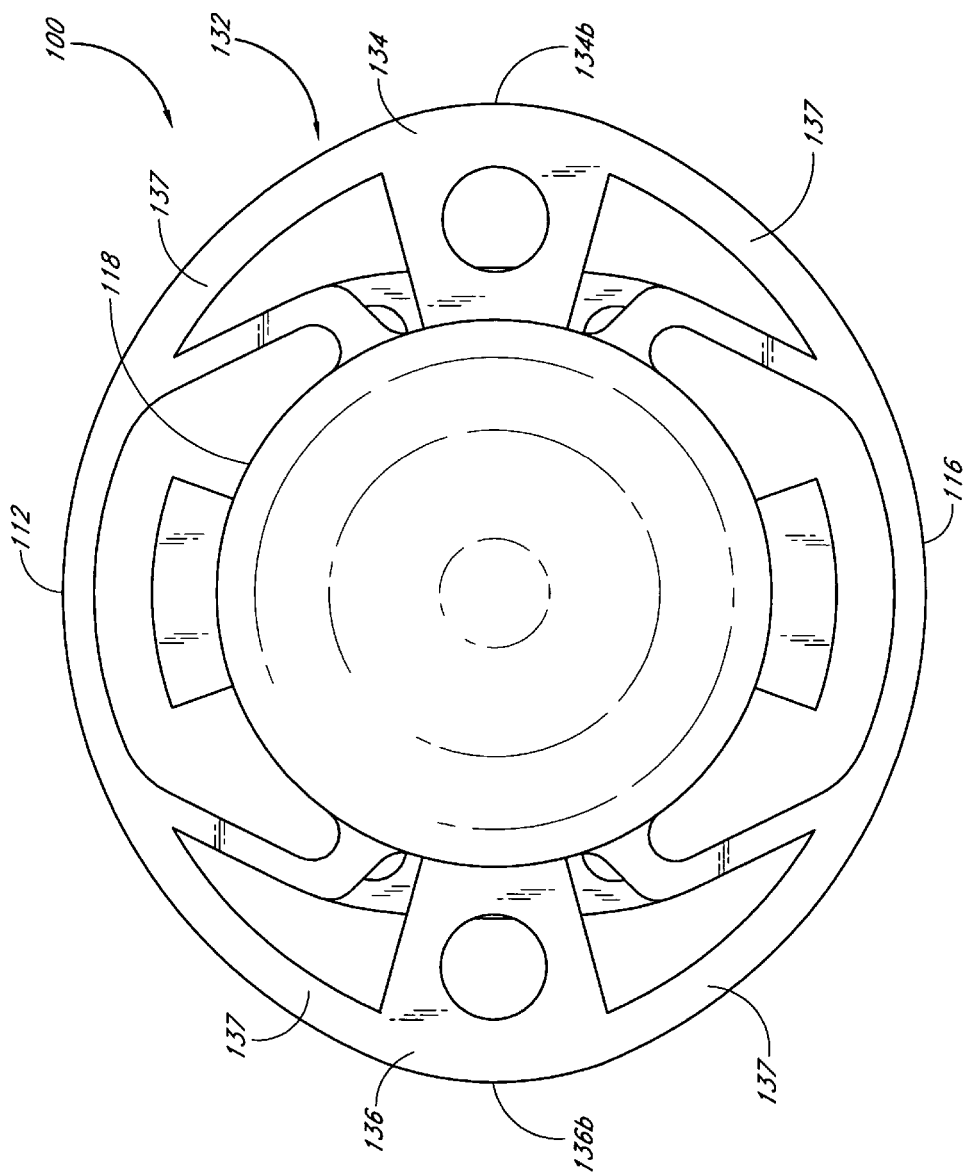
FIG. 21B is a front view of another embodiment of the lens system.

FIG. 21B shows another alternative configuration of the distending portion 132, in which arcuate rim portions 137 interconnect the apices 112, 116 and the free ends 134b, 136b of the distending members 134, 136. Thus is formed an integral perimeter member with generally higher lateral rigidity than the arrangement depicted in FIG. 21A.

Figure 21C:
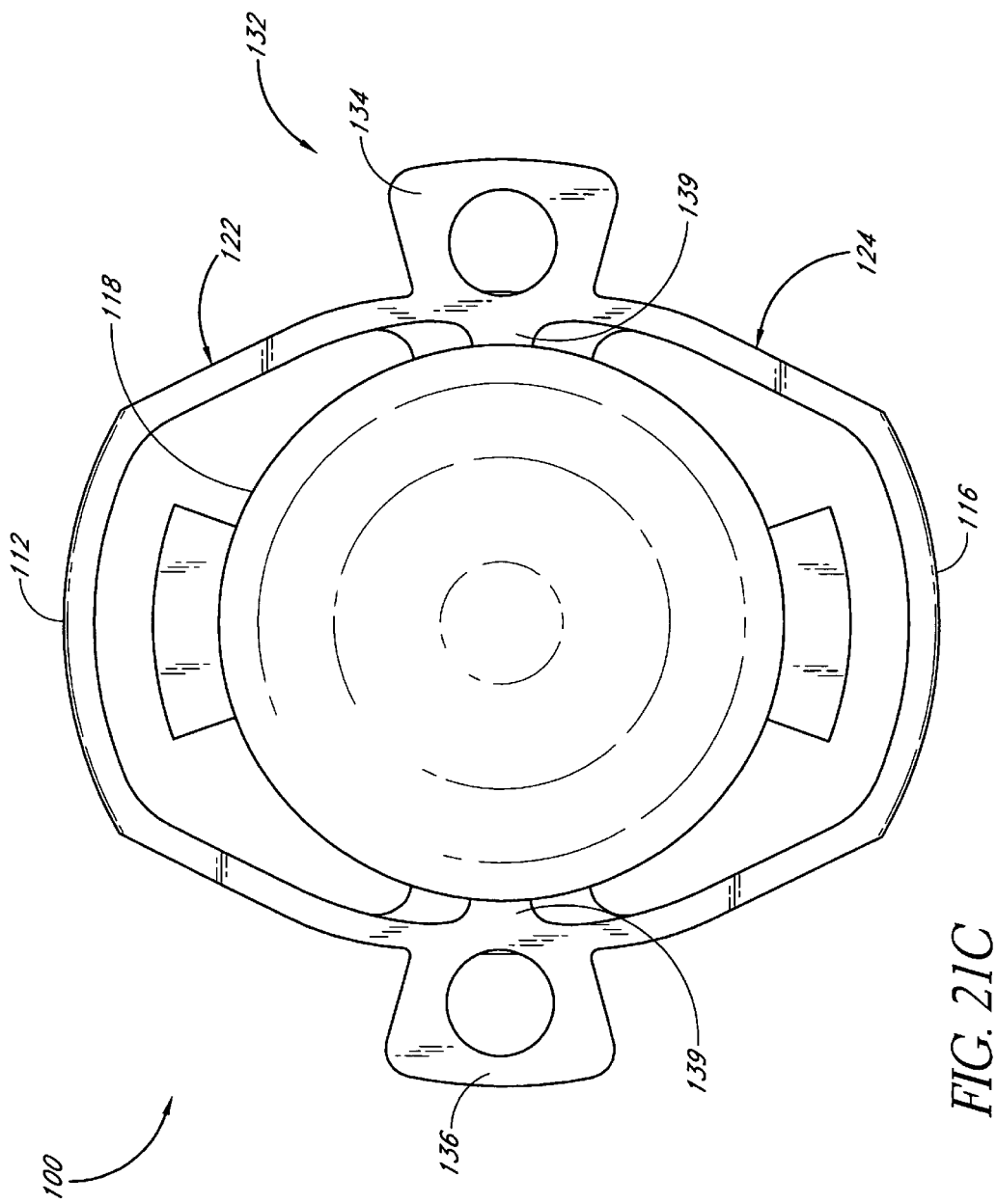
FIG. 21C is a front view of another embodiment of the lens system.

FIG. 21C shows another alternative configuration of the distending portion 132, in which the distending members 134, 136 are integrally formed with the first and second posterior translation members 122, 124. The distending members 134, 136 and translation members 122, 124 thus form common transition members 139 which connect to the periphery of the posterior viewing element 118.

Figure 22:
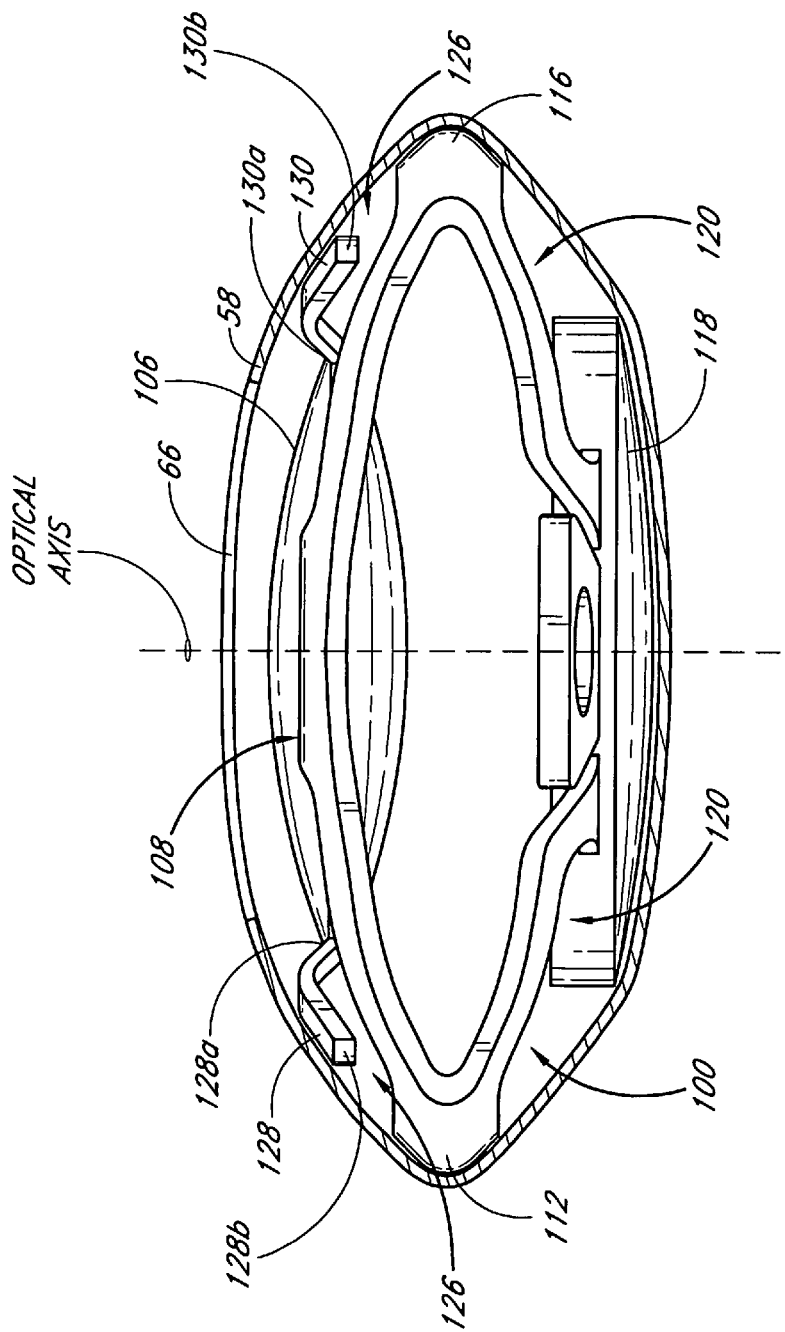
FIG. 22 is a partial side sectional view of another embodiment of the lens system, implanted in the capsular bag.

FIG. 22 shows the function of the retention portion 126 in greater detail. It is readily seen that the first and second retention members 128, 130 facilitate a broad contact base between the anterior portion of the lens system 100 and the anterior aspect of the capsular bag 58. By appropriately spacing the first and second retention members 128, 130, the members prevent extrusion of the anterior viewing element 106 through the anterior opening 66. It is also readily seen that where contact occurs between the anterior aspect of the capsular bag 58 and one or both of the retention members 128, 130, the retention members also participate in force coupling between the bag 58 and the lens system 100 as the bag is stretched and released by the action of the ciliary muscles.

As best seen in FIGS. 21 and 22, the anterior portion 102 of the lens system 100 forms a number of regions of contact with the capsular bag 58, around the perimeter of the anterior viewing element 106. In the illustrated embodiment, at least some of these regions of contact are located on the anteriormost portions of the anterior biasing element 108, specifically at the transition members 138, 140, and at the retention members 128, 130. The transition members and the retention members define spaces therebetween at the edges of the anterior viewing element 106 to permit fluid to flow between the interior of the capsular bag 58 and the portions of the eye anterior of the bag 58. In other words, the anterior portion of the lens system 100 includes at least one location which is spaced from and out of contact with the capsular bag 58 to provide a fluid flow channel extending from the region between the viewing elements 106, 118 to the exterior of the bag 58. Otherwise, if the anterior portion 102 of the lens system 100 seals the anterior opening 66 of the bag 58, the resulting prevention of fluid flow can cause the aqueous humor in the capsular bag to stagnate, leading to a clinically adverse event, and can inhibit the movement of the lens system 100 between the accommodated and unaccommodated states.

If desired, one or both of the retention members 128, 130 may have an opening 129 formed therein to permit fluid flow as discussed above. (See FIG. 21A.)

The retention members 128, 130 and the transition members 138, 140 also prevent contact between the iris and the anterior viewing element 106, by separating the anterior opening 66 from the anterior face of the viewing element 106. In other words, the retention members 128, 130 and the transition members 138, 140 displace the anterior aspect of the capsular bag 58, including the anterior opening 66, anteriorly from the anterior viewing element 106, and maintain this separation throughout the range of accommodation of the lens system. Thus, if contact occurs between the iris and the lens system-capsular bag assembly, no part of the lens system will touch the iris, only the capsular bag itself, in particular those portions of the bag 58 overlying the retention members 128, 130 and/or the transition members 138, 140. The retention members 128, 130 and/or the transition members 138, 140 therefore maintain a separation between the iris and the lens system, which can be clinically adverse if the contacting portion(s) of the lens system are constructed from silicone.

Figure 22A:
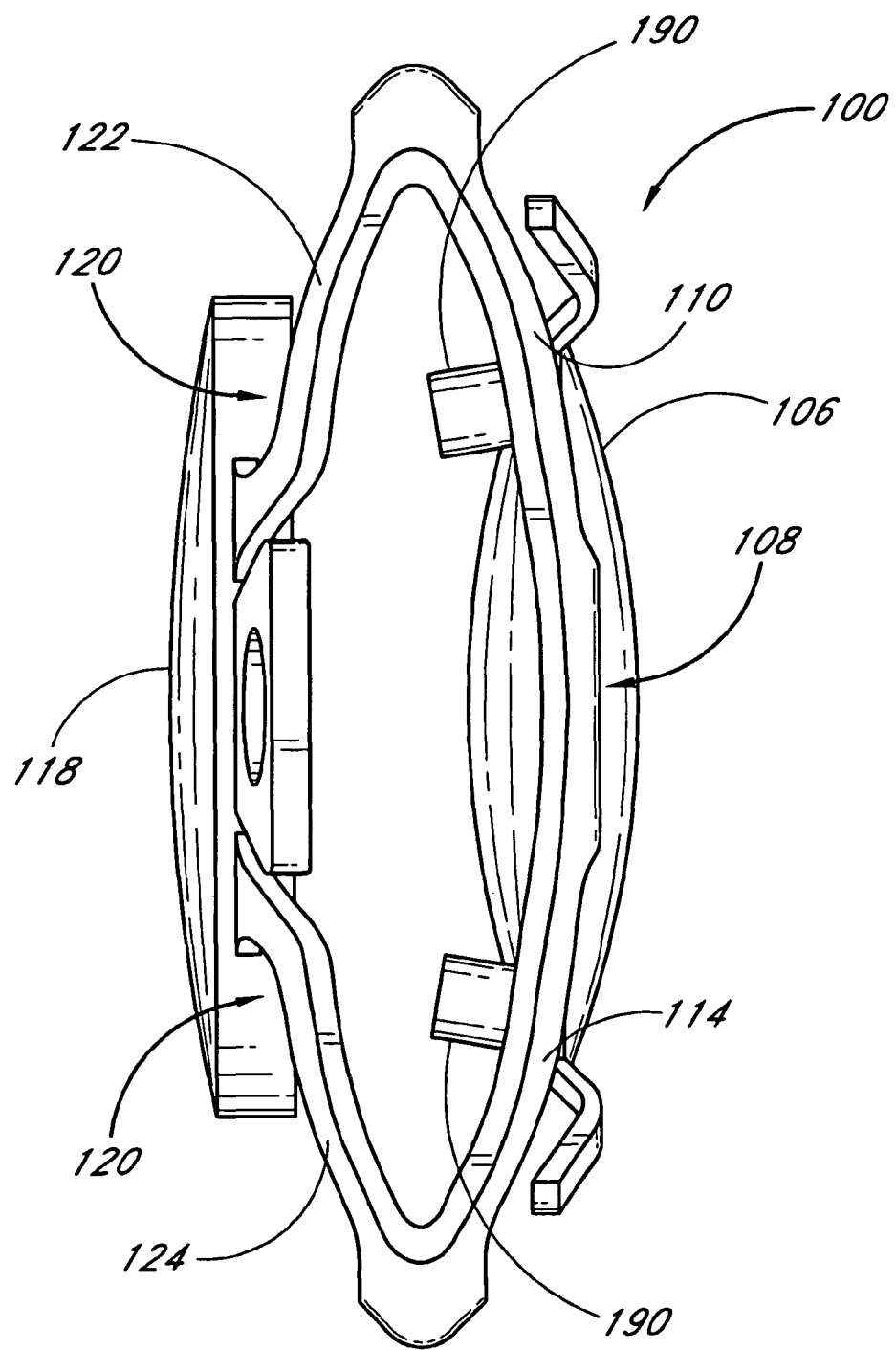
FIG. 22A is a side view of a stop member system employed in one embodiment of the lens system.
Figure 23:
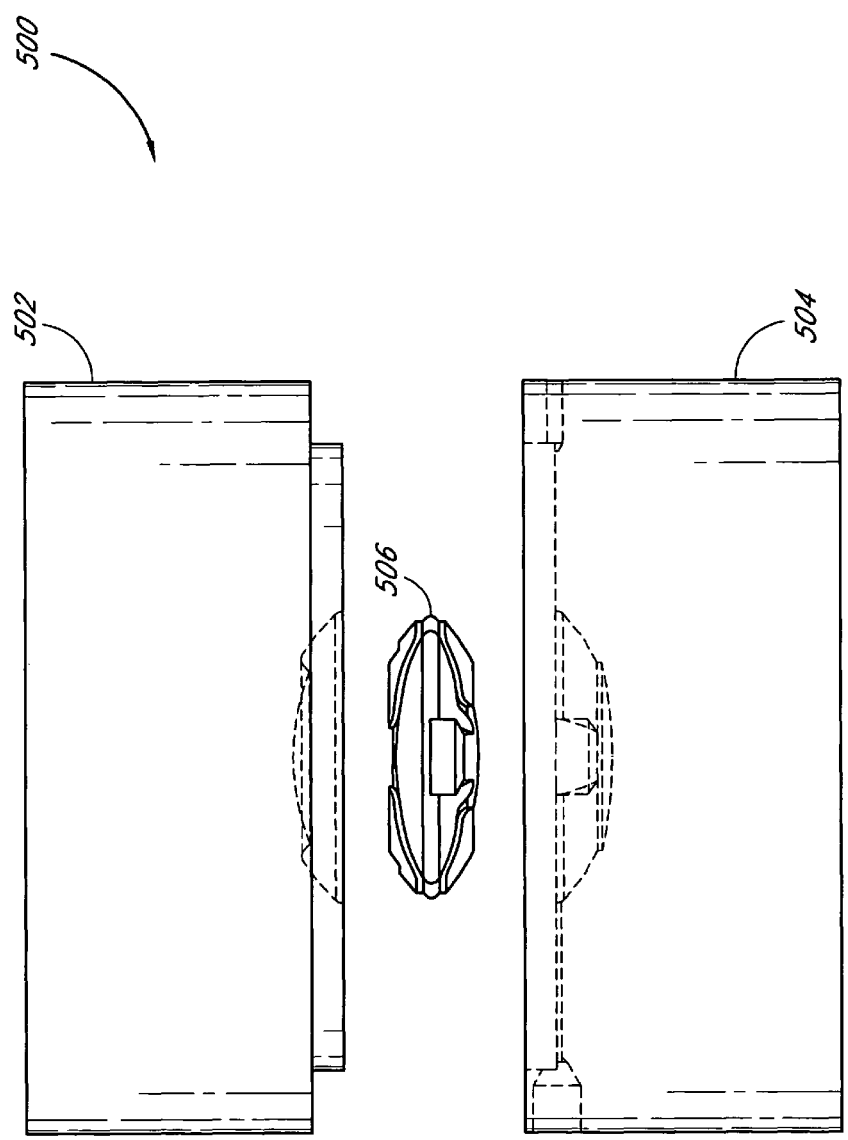
FIG. 23 is a side view of a mold system for forming the lens system.
Figure 24:
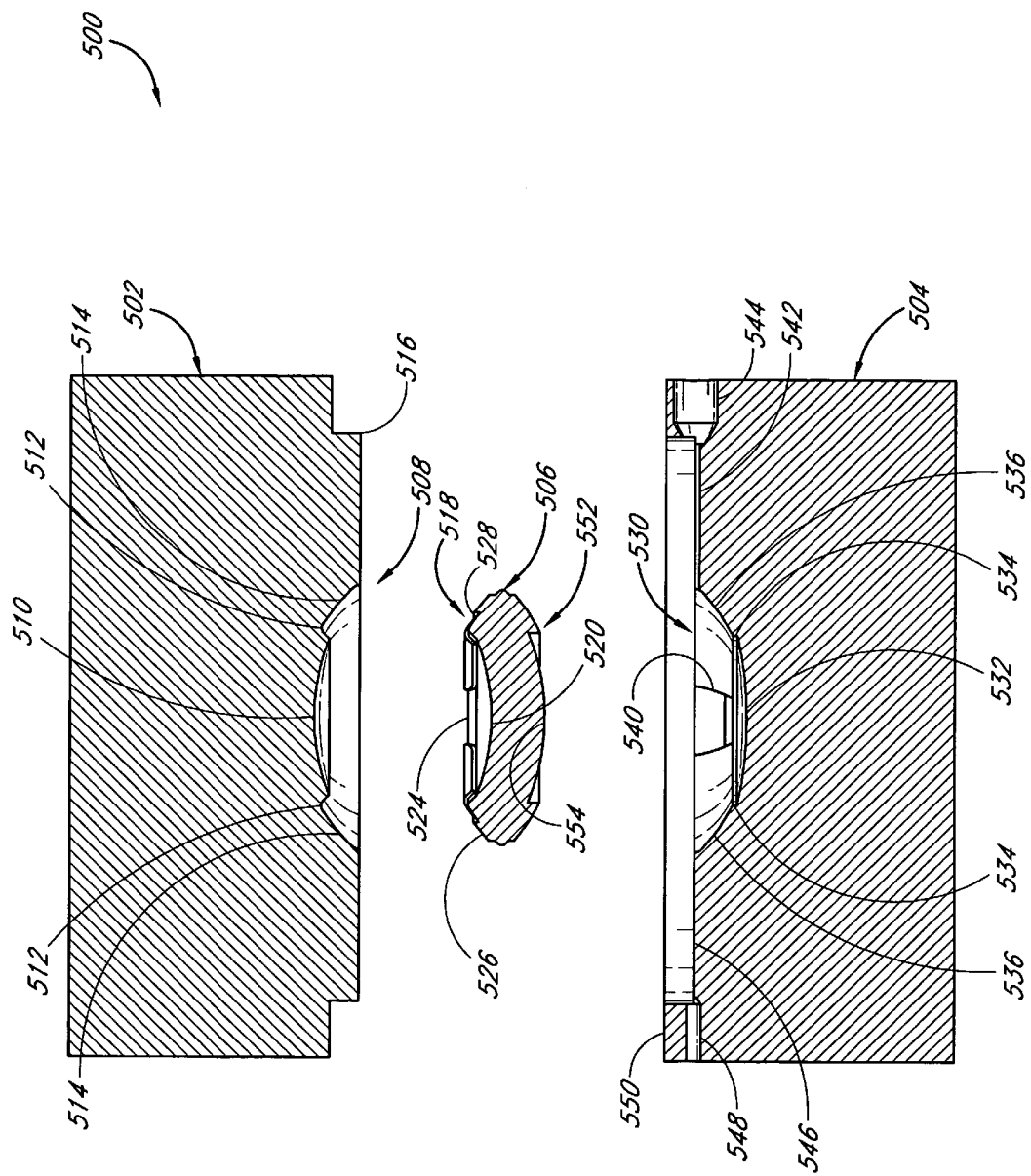
FIG. 24 is a side sectional view of the mold system.
Figure 25:
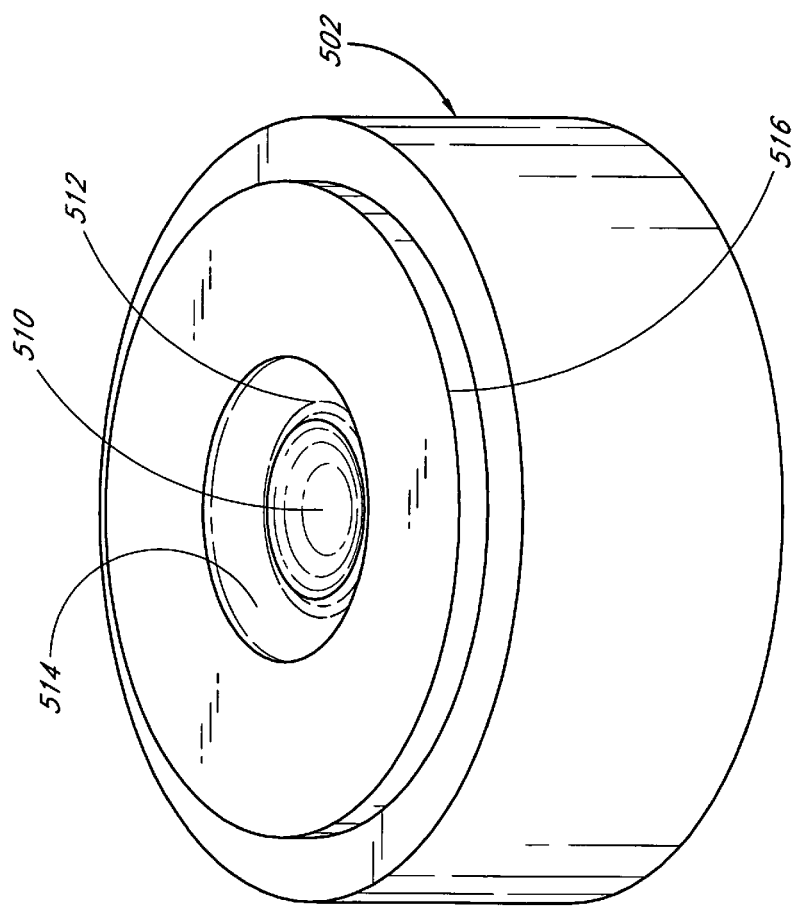
FIG. 25 is a perspective view of a first mold portion.
Figure 26:
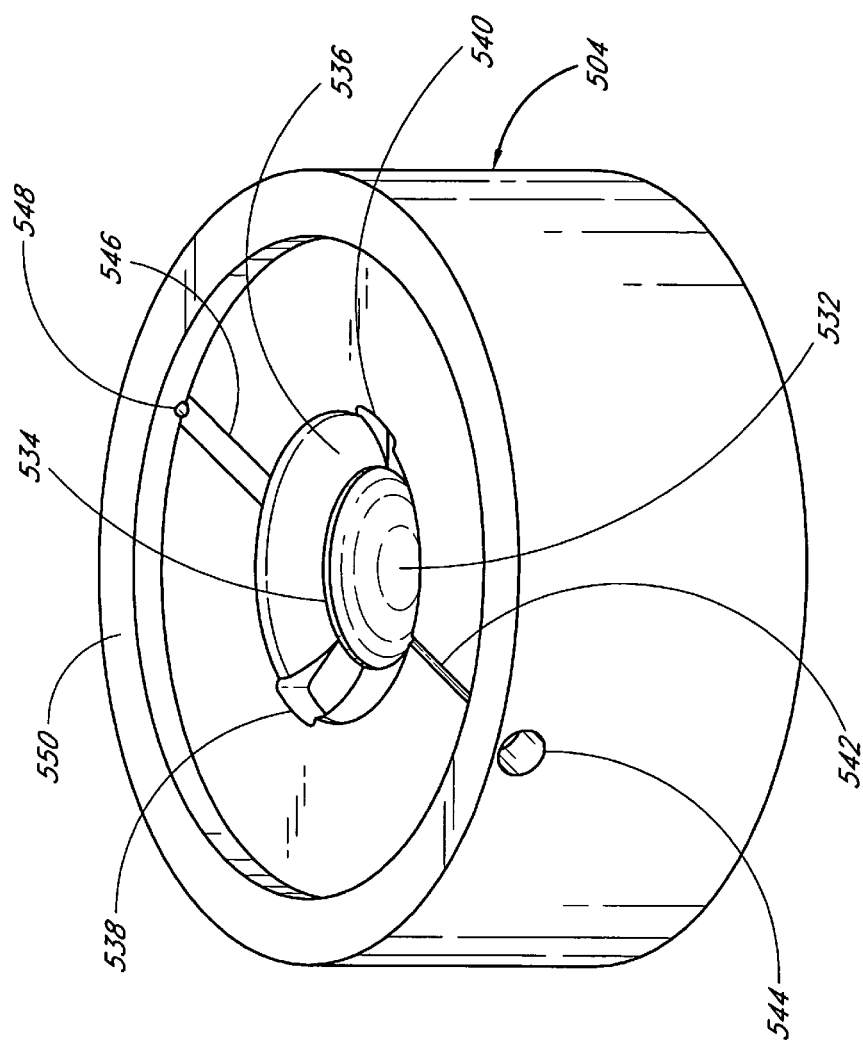
FIG. 26 is a perspective view of a second mold portion.
Figure 27:
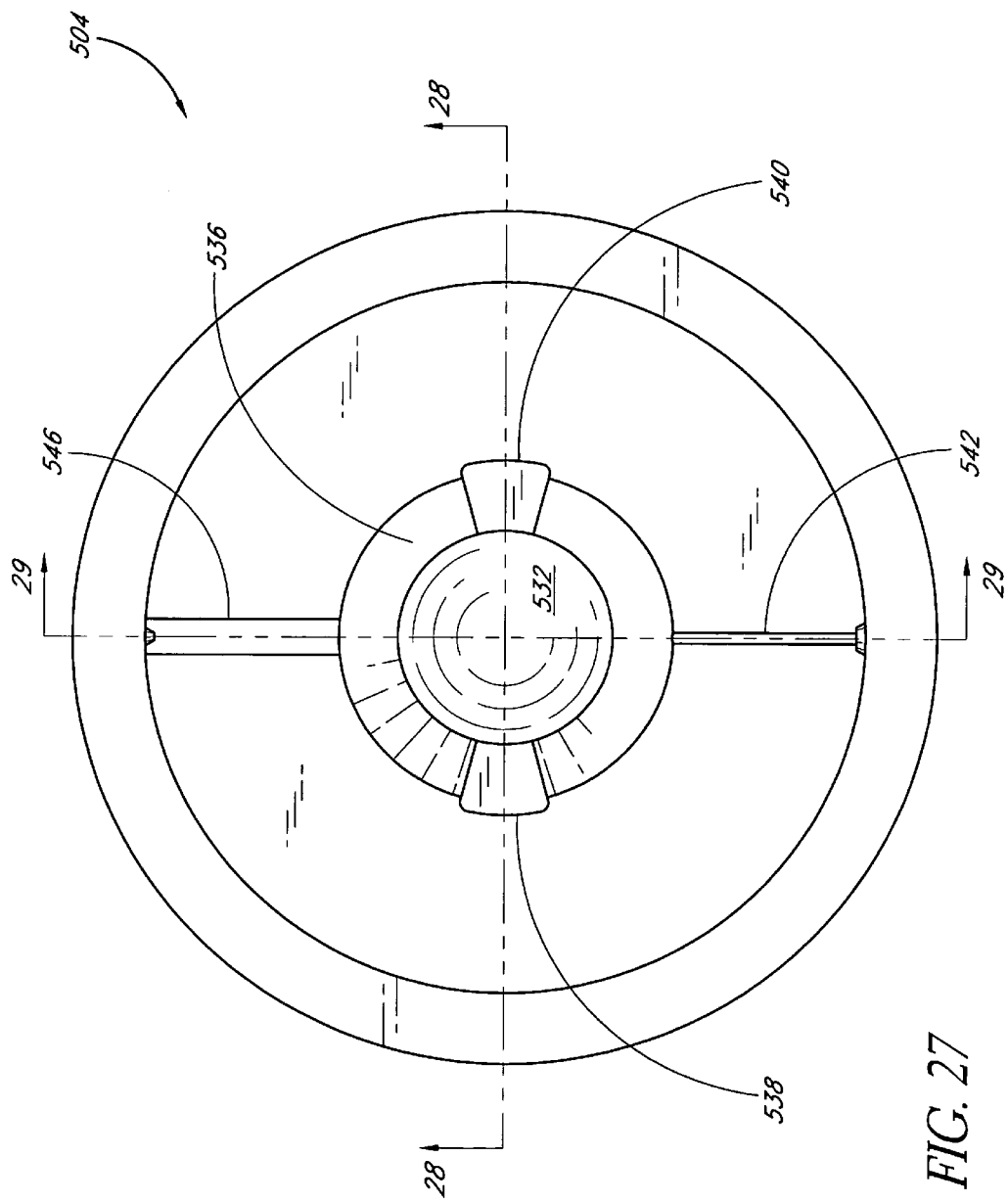
FIG. 27 is a top view of the second mold portion.
Figure 28:
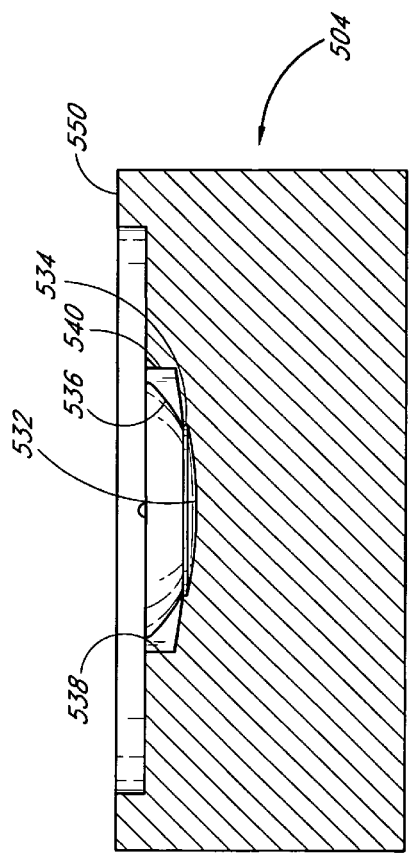
FIG. 28 is a side sectional view of the second mold portion.
Figure 29:
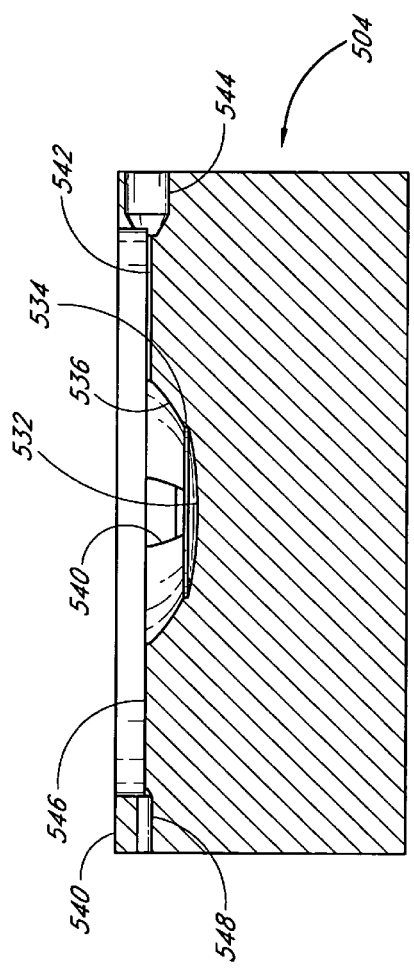
FIG. 29 is another side sectional view of the second mold portion.
Figure 30:
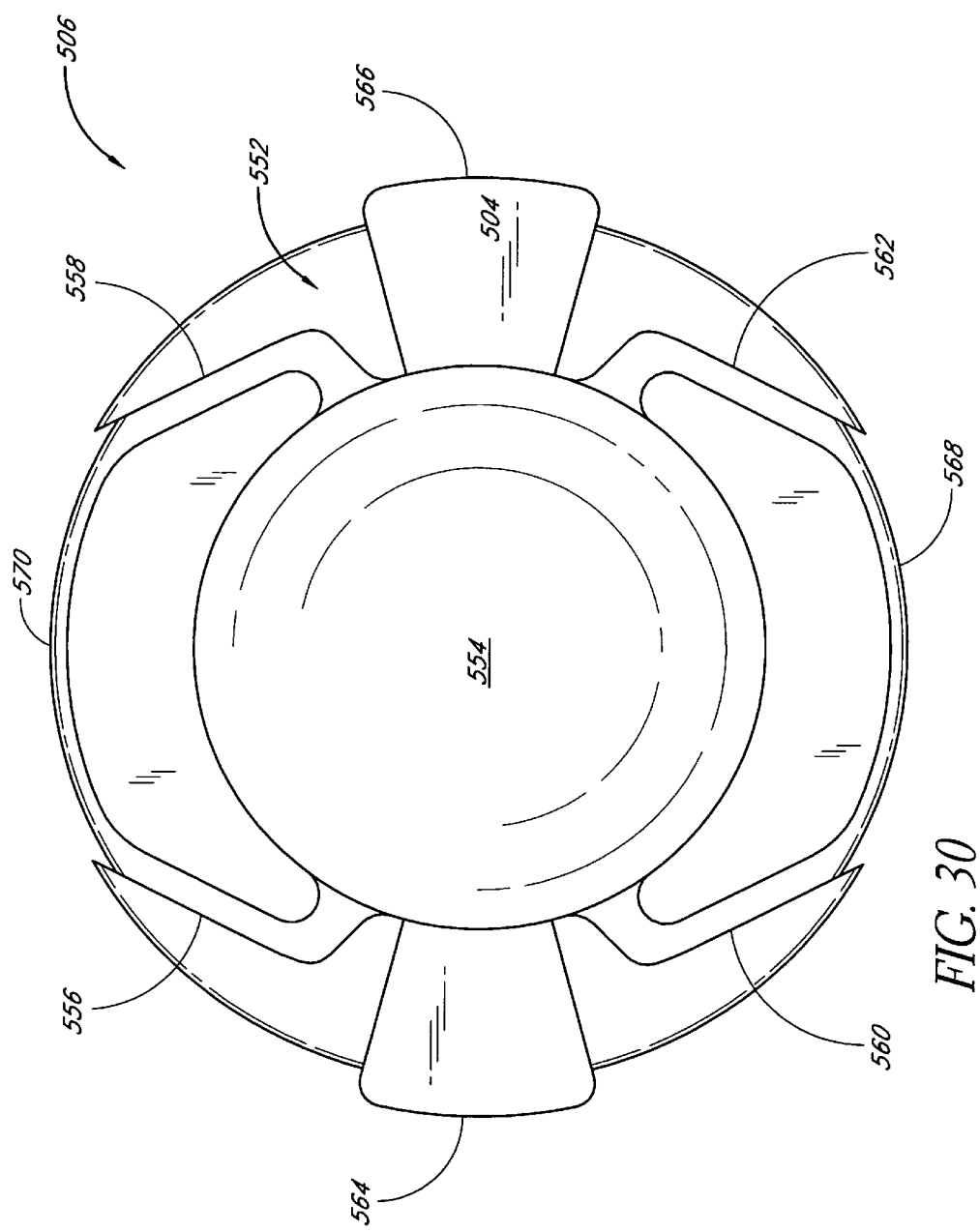
FIG. 30 is a bottom view of a center mold portion.
Figure 31:
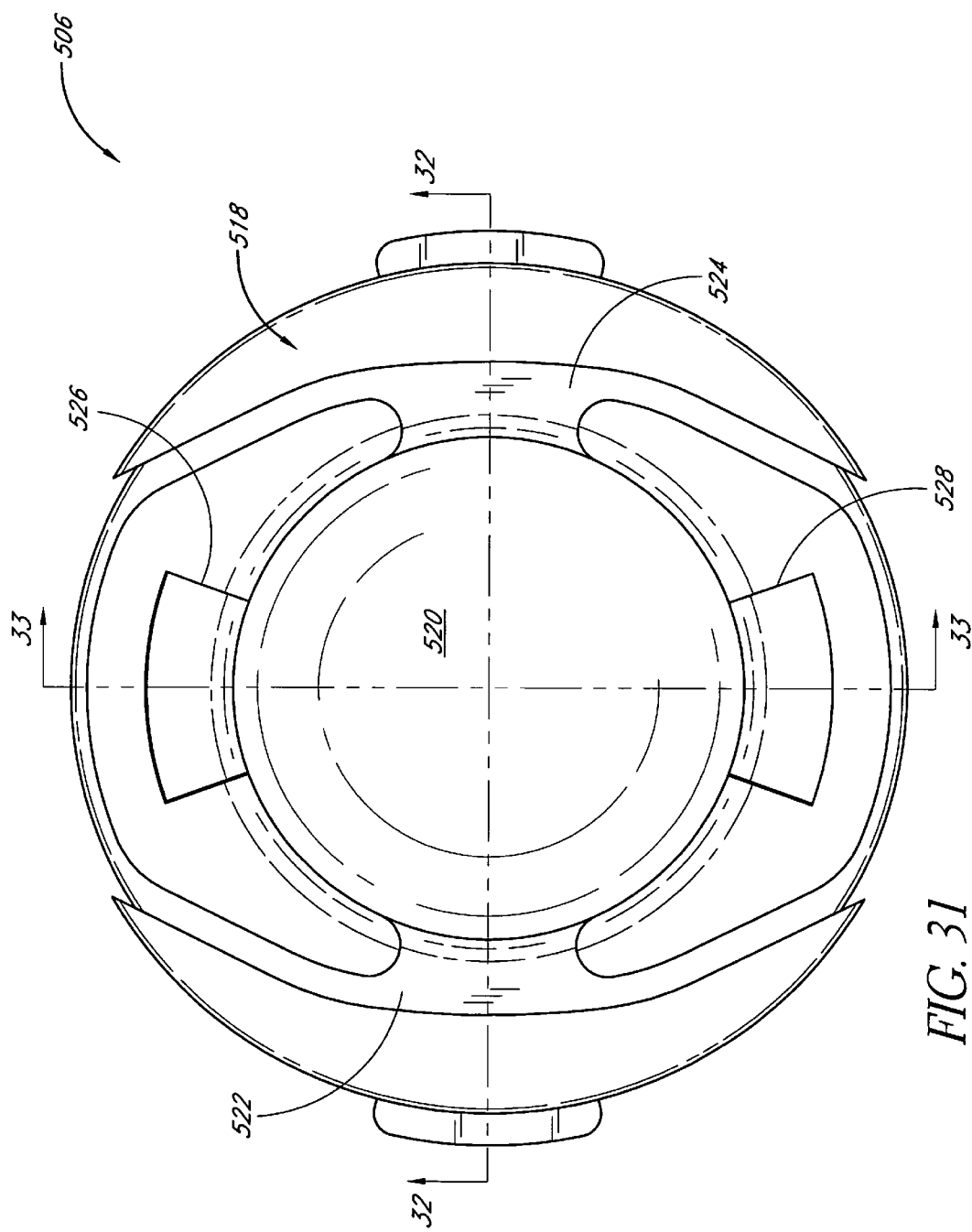
FIG. 31 is a top view of the center mold portion.
Figure 33:
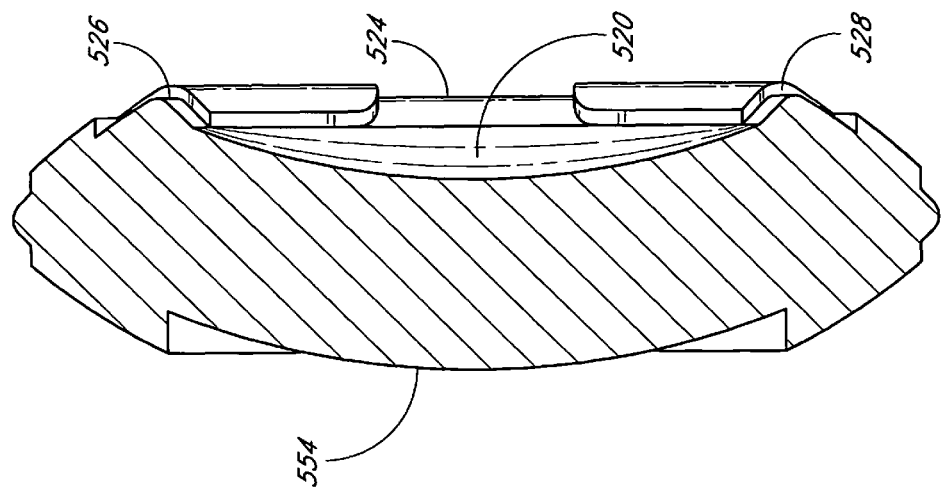
FIG. 33 is another sectional view of the center mold portion.
Figure 32:
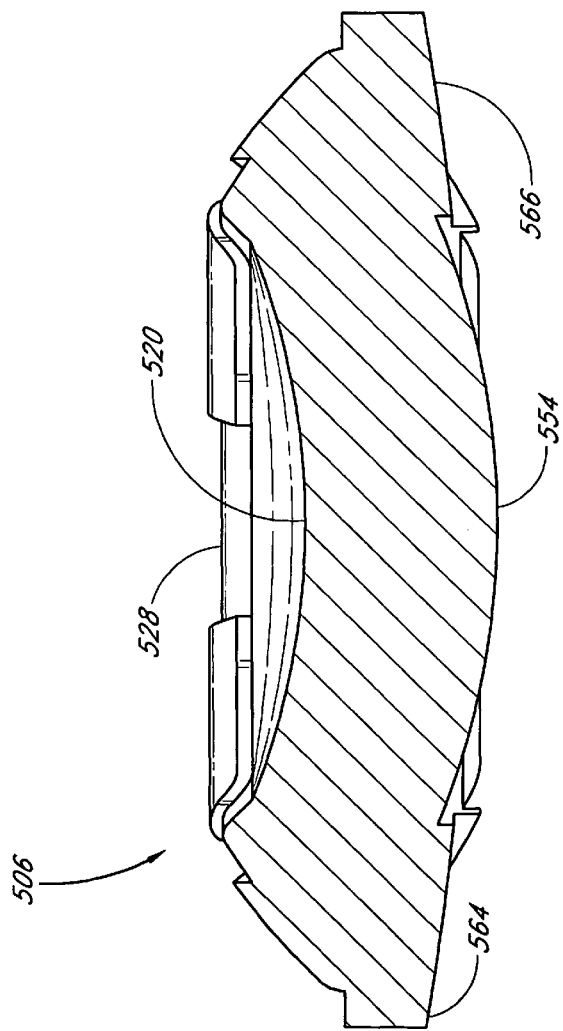
FIG. 32 is a sectional view of the center mold portion.

As depicted in FIG. 22A, one or more stop members or separation members 190 may be located where appropriate on the anterior and/or posterior biasing elements 108, 120 to limit the convergent motion of the anterior and posterior viewing elements 106, 118, and preferably prevent contact therebetween. As the lens system 100 moves toward the unaccommodated position, the stop member(s) located on the anterior biasing element 108 come into contact with the posterior biasing element 120 (or with additional stop member(s) located on thereon), and any stop member(s) located on the posterior biasing element 120 come into contact with the anterior biasing element 108 (or with additional stop member(s) located thereon). The stop members 190 thus define a point or state of maximum convergence (in other words, the unaccommodated state) of the lens system 100/viewing elements 106, 118. Such definition advantageously assists in setting one extreme of the range of focal lengths which the lens system may take on (in those lens systems which include two or more viewing elements having refractive power) and/or one extreme of the range of motion of the lens system 100.

The stop members 190 shown in FIG. 22A are located on the first and second anterior translation members 110, 114 of the anterior biasing element 108 and extend posteriorly therefrom. When the anterior and posterior viewing elements 106, 118 move together, one or more of the stop members 190 will contact the posterior translation member(s) 122, 124, thereby preventing further convergent motion of the viewing elements 106, 118. Of course, in other embodiments the stop member(s) 190 can be in any suitable location on the lens system 100.

FIGS. 44-48 depict another embodiment of the lens system 100 having a number of stop members or separation members 190. In this embodiment the stop members 190 include posts 190a and tabs 190b, although it will be apparent that any number or combination of suitable shapes may be employed for the stop members 190. Each of the stop members 190 has at least one contact surface 191, one or more of which abuts an opposing surface of the lens system 100 when the anterior and posterior viewing elements 106, 118 converge to a minimum separation distance SD (see FIG. 47). In the embodiment shown, one or more of the contact surfaces 191 of the posts 190a are configured to abut an opposing surface defined by a substantially flat anterior perimeter portion 193 of the posterior viewing element 118, when the viewing elements 106, 118 are at the minimum separation distance SD. One or more of the contact surfaces 191 of the tabs 190b are configured to abut opposing surfaces defined by substantially flat anterior faces 195 of the distending members 134, 136, only if the viewing elements 106, 118 are urged together beyond the minimum separation distance SD. This arrangement permits the tabs 190b to function as secondary stop members should the posts 190a fail to maintain separation of the viewing elements.

In other embodiments all of the contact surfaces 191 of the posts 190a and tabs 190b may be configured to contact their respective opposing surfaces when the viewing elements 106, 118 are at the minimum separation distance SD. In still further embodiments, the contact surfaces 191 of the tabs 190b may be configured to contact the opposing surfaces when the viewing elements 106, 118 are at the minimum separation distance SD and the contact surfaces 191 of the posts 190a configured to contact the opposing surfaces only if the viewing elements 106, 118 are urged together beyond the minimum separation distance SD. In one embodiment, the minimum separation distance SD is about 0.1-1.0 mm; in another embodiment the minimum separation distance SD is about 0.5 mm.

Figure 48:
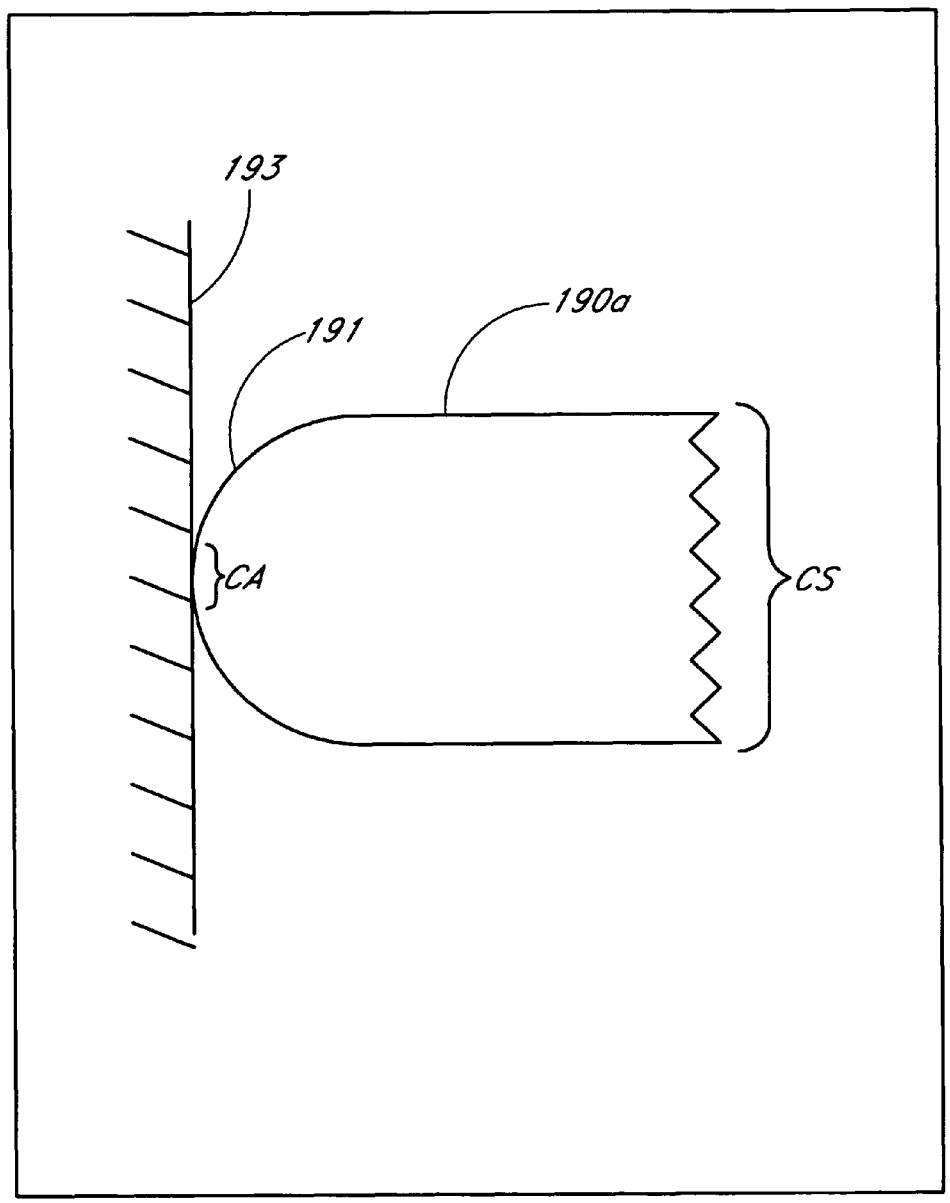
FIG. 48 is a closeup view of the contact between a separation member and an opposing surface.

When one of the contact surfaces abuts one of the opposing surfaces, the two surfaces define a contact area CA (see FIG. 48, depicting an example of a contact area CA defined when the contact surface 191 of a post 190a contacts an opposing surface defined by the perimeter portion 193 of the posterior viewing element 118). Preferably, the contact surface and opposing surface are shaped to cooperatively minimize the size of the contact area, to prevent adhesion between the contact surface and the opposing surface, which is often a concern when one or both of these surfaces has an adhesive affinity for the other. In the embodiment shown, this non-adhesive characteristic is achieved by employing a substantially hemispherical contact surface 191 and a substantially flat opposing surface (perimeter portion 193). Of course, other configurations can be selected for the contact surface(s) 191, including conical, frustoconical, hemicylindrical, pyramidal, or other rounded, tapered or pointed shapes. All of these configurations minimize the contact area CA while permitting the cross-sectional area CS of the stop member 190 (such as the post 190a depicted) to be made larger than the contact area CA, to impart sufficient strength to the stop member despite the relatively small contact area CA. Indeed, when constructing the contact surface(s) 191 any configuration may be employed which defines a contact area CA which is smaller than the cross-sectional area CS of the stop member 190. As further alternatives, the contact surface(s) 191 may be substantially flat and the opposing surface(s) may have a shape which defines, upon contact with the opposing surface, a contact area CA which is smaller than the cross-sectional area CS of the stop member. Thus, the opposing surface(s) may have, for example, a hemispherical, conical, frustoconical, hemicylindrical, pyramidal, or other rounded, tapered or pointed shape.

Other design features of the stop members 190 can be selected to maximize their ability to prevent adhesion of the contact surface(s) to the corresponding opposing surface(s), or adhesion to each other of any part of the anterior and posterior portions 102, 104 of the lens system 100. For example, the contact and opposing surfaces may be formed from dissimilar materials to reduce the effect of any self-adhesive materials employed in forming the lens system 100. In addition the shape and/or material employed in constructing one or more of the stop members 190 can be selected to impart a spring-like quality to the stop member(s) in question, so that when the stop member is loaded in compression as the viewing elements are urged together at the minimum separation distance, the stop member tends to exert a resisting spring force, due to either bending or axial compression (or both) of the stop member, which in turn derive from the elasticity of the material(s) from which the stop member is constructed, or the shape of the stop member, or both. This springlike quality is particularly effective for inhibiting adhesion of areas of the anterior and posterior portions 102, 104 other than the contact surface(s) and opposing surface(s).

As used herein, the term "adhesion" refers to attachment to each other of (i) an area of the anterior portion 102 of the lens system 100 and (ii) a corresponding area of the posterior portion 104 (other than the apices 112, 116), wherein such attachment is sufficiently strong to prevent, other than momentarily, the anterior and posterior viewing elements 106, 118 from moving apart along the optical axis under the biasing force of the anterior and/or posterior biasing elements 108, 120. If the areas in question are formed of different materials, adhesion may occur where at least one of the materials has an adhesive affinity for the other material. If the areas in question are formed of the same material, adhesion may occur where the material has an adhesive affinity for itself.

In the embodiment shown, four posts 190a are positioned near the perimeter of the anterior viewing element 106, equally angularly spaced around the optical axis. In addition, two tabs 190b are located on either side of the anterior viewing element, midway between the apices 112, 116 of the lens system. Naturally, the number, type and/or position of the stop members 190 can be varied while preserving the advantageous function of maintaining separation between the anterior and posterior portions of the lens system.

The illustrated embodiment employs stop members 190 which extend posteriorly from the anterior portion 102 of the lens system 100, so that the contact surfaces 191 are located on the posterior extremities of the stop members 190 and are configured to abut opposing surfaces formed on the posterior portion 104 of the lens system 100. However, it will be appreciated that some or all of the stop members 190 may extend anteriorly from the posterior portion 104 of the lens system 100, so that their contact surfaces 191 are located on the anterior extremities of the stop members 190 and are configured to abut opposing surfaces formed on the anterior portion 102 of the lens system 100.

VI. Mold Tooling

FIGS. 23-34 depict a mold system 500 which is suitable for molding the lens system 100 depicted in FIG. 3-17. The mold system 500 generally comprises a first mold 502, a second mold 504 and a center mold 506. The center mold 506 is adapted to be positioned between the first mold 502 and the second mold 504 so as to define a mold space for injection molding or compression molding the lens system 100. The mold system 500 may be formed from suitable metals, high-impact-resistant plastics or a combination thereof, and can be produced by conventional machining techniques such as lathing or milling, or by laser or electrical-discharge machining. The mold surfaces can be finished or modified by sand blasting, etching or other texturing techniques.

The first mold 502 includes a first mold cavity 508 with a first anterior mold face 510 surrounded by an annular trough 512 and a first perimeter mold face 514. The first mold 502 also includes a projection 516 which facilitates easier mating with the second mold 504.

The center mold 506 includes a first center mold cavity 518 which cooperates with the first mold cavity 508 to define a mold space for forming the anterior portion 102 of the lens system 100. The first center mold cavity 518 includes a central anterior mold face 520 which, upon placement of the center mold 506 in the first mold cavity 508, cooperates with the first anterior mold face 510 to define a mold space for the anterior viewing element 106. In so doing, the first anterior mold face 510 defines the anterior face of the anterior viewing element 106 and the central anterior mold face 520 defines the posterior face of the anterior viewing element 106. In fluid communication with the chamber formed by the first anterior mold face 510 and the central anterior mold face 520 are lateral channels 522, 524 (best seen in FIG. 31) which form spaces for molding the first and second transition members 138, 140, along with the arms 110a, 110b of the first anterior translation member 110 as well as the arms 114a, 114b of the second anterior translation member 114. The first center mold cavity 518 also includes retention member cavities 526, 528 which define spaces for molding the first and second retention members 128, 130 to the anterior viewing element 106.

The second mold 504 includes a second mold cavity 530 with a second posterior mold space 532, a generally cylindrical transition 534 extending therefrom and connecting to a second perimeter mold face 536. Lateral notches 538, 540 (best seen in FIGS. 26 and 27) are formed in the second perimeter mold face 536. The second mold 504 also includes an input channel 542 connected to an input channel opening 544 for introducing material into the mold system 500. Also formed in the second mold 504 is an output channel 546 and an output channel opening 548. A generally cylindrical rim 550 is included for mating with the projection 516 of the first mold 502.

The center mold 506 includes a second center mold cavity 552 which cooperates with the second mold cavity 530 to define a mold space for the posterior portion 104 of the lens system 100. The second center mold cavity 552 includes a central posterior mold face 554 which, upon placement of the center mold 506 in engagement with the second mold cavity 530, cooperates with the second posterior mold face 532 and the transition 534 to define a chamber for forming the posterior viewing element 118. In fluid communication with the chamber formed by the central posterior mold face 554 and the second posterior mold face 532 are lateral channels 556, 558, 560, 562 which provide a mold space for forming the arms 122a, 122b of the first posterior translation member 122 and the arms 124a, 124b of the second posterior translation member 124. The second center mold cavity 552 includes lateral projections 564, 566 which coact with the notches 538, 540 formed in the second mold cavity 530. The chambers formed therebetween are in fluid communication with the chamber defined by the central posterior mold face 554 and the second posterior mold face 532 to form the first and second distending members 134, 136 integrally with the posterior viewing element 118.

The center mold 506 includes a first reduced-diameter portion 568 and a second reduced-diameter portion 570 each of which, upon assembly of the mold system 500, defines a mold space for the apices 112, 116 of the lens system 100.

In use, the mold system 500 is assembled with the center mold 506 positioned between the first mold 502 and the second mold 504. Once placed in this configuration, the mold system 500 is held together under force by appropriate techniques, and lens material is introduced into the mold system 500 via the input channel 542. The lens material then fills the space defined by the first mold 502, second mold 504, and the center mold 506 to take on the shape of the finished lens system 100.

The mold system 500 is then disassembled, and in one embodiment the lens system 100 is left in position on the center mold 506 after removal of the first and second molds 502, 504. This technique has been found to improve the effectiveness of any polishing/tumbling/deflashing procedures which may be performed (see further discussion below). Whether or not these or any other additional process steps are performed, the lens system 100 is preferably removed from the center mold 506 while maintaining the interconnection of the various components of the lens system 100.

In another embodiment, the lens system 100 or a portion thereof is formed by a casting or liquid-casting procedure in which one of the first or second molds is first filled with a liquid and the center mold is placed then into engagement with the liquid-filled mold. The exposed face of the center mold is then filled with liquid and the other of the first and second molds is placed into engagement with the rest of the mold system. The liquid is allowed or caused to set/cure and a finished casting may then removed from the mold system.

The mold system 500 can advantageously be employed to produce a lens system 100 as a single, integral unit (in other words, as a single piece of material). Alternatively, various portions of the lens system 100 can be separately molded, casted, machined, etc. and subsequently assembled to create a finished lens system. Assembly can be performed as a part of centralized manufacturing operations; alternatively, a physician can perform some or all of the assembly before or during the implantation procedure, to select lens powers, biasing members, system sizes, etc. which are appropriate for a particular patient.

The center mold 506 is depicted as comprising an integral unit with first and second center mold cavities 518, 552. Alternatively, the center mold 506 may have a modular configuration whereby the first and second mold cavities 518, 552 may be interchangeable to adapt the center mold 506 for manufacturing a lens system 100 according to a desired prescription or specification, or to otherwise change the power(s) of the lenses made with the mold. In this manner the manufacture of a wide variety of prescriptions may be facilitated by a set of mold cavities which can be assembled back-to-back or to opposing sides of a main mold structure.

Figure 49:
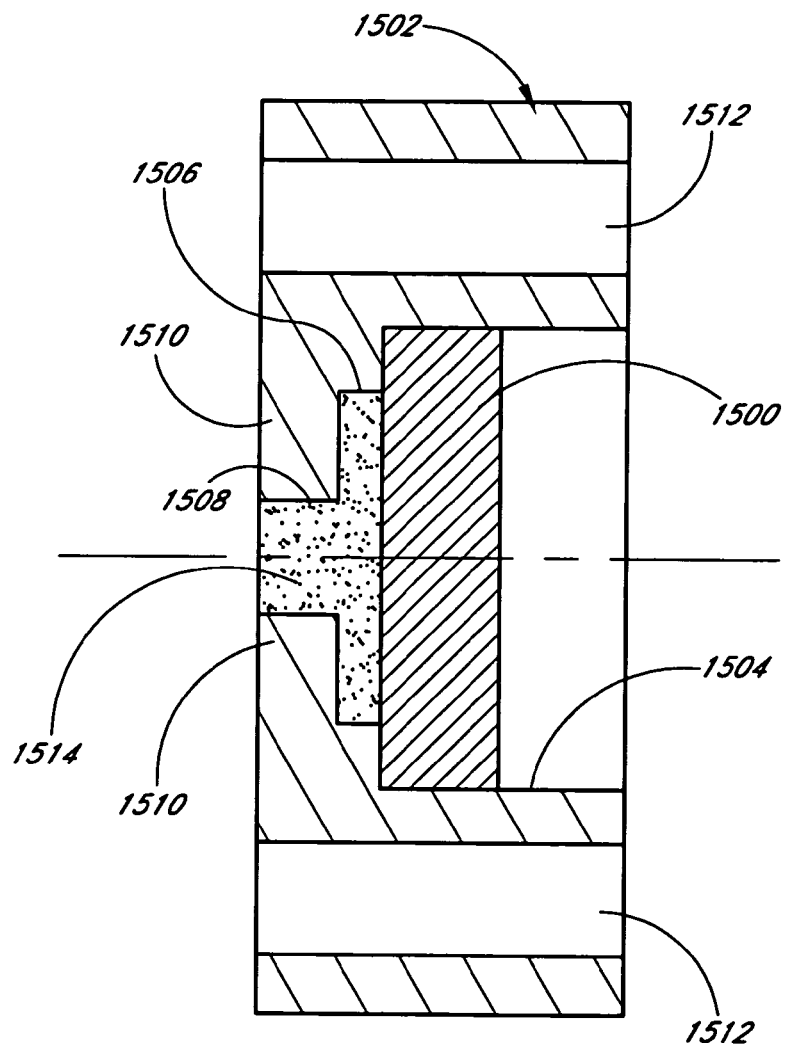
FIG. 49 is a side sectional view of an apparatus and method for manufacturing a center mold.
Figure 50:
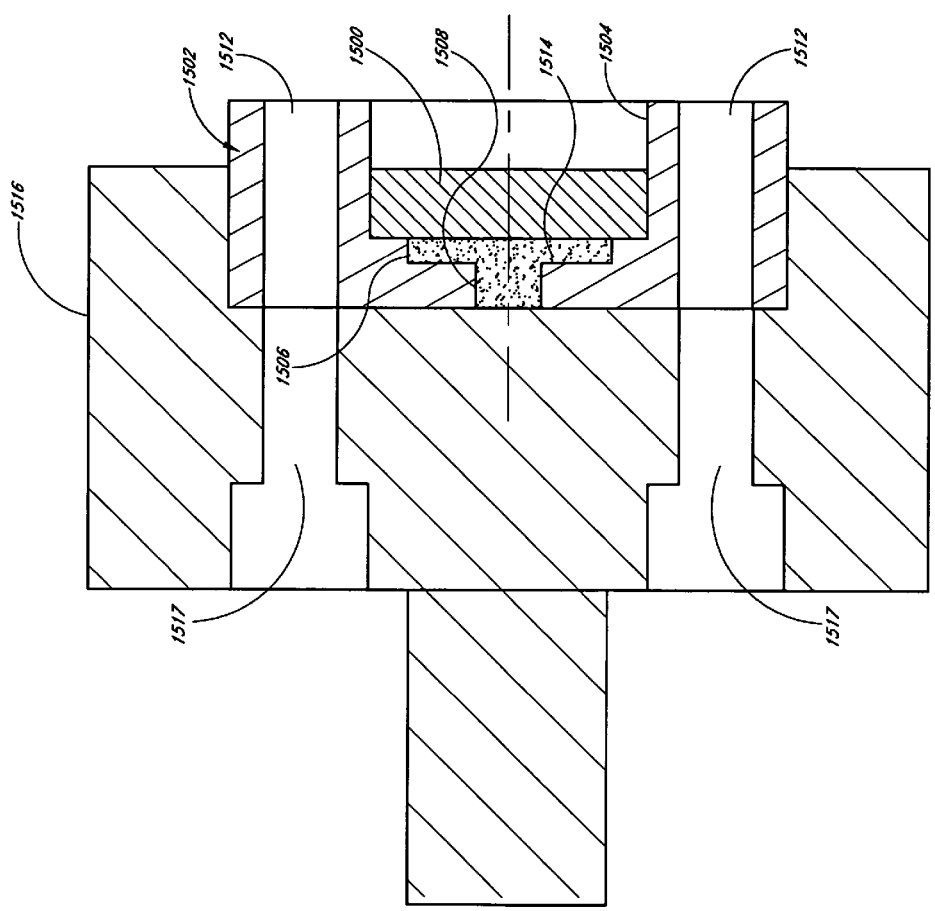
FIG. 50 is another side sectional view of the apparatus and method of FIG. 49.

FIGS. 49-53 depict one embodiment of a method for manufacturing the center mold 506. First, a cylindrical blank 1500 formed from any material (such as Ultem) suitable for use in the mold tooling, is loaded into a holder 1502 as shown in FIG. 49. The holder 1502 has a main chamber 1504 which has an inner diameter substantially similar to that of the blank 1500, a smaller-diameter secondary chamber 1506 rearward of the main chamber 1504, and a passage 1508 located rearward of the secondary chamber 1506 and further defined by an annulus 1510. The holder also includes two or more holder bores 1512 which facilitate attachment of the holder 1502 to a blocker (discussed in further detail below). The blank is "blocked" in the holder by filling the secondary chamber 1506 and passage 1508 with water-soluble wax 1514.

Figure 51:
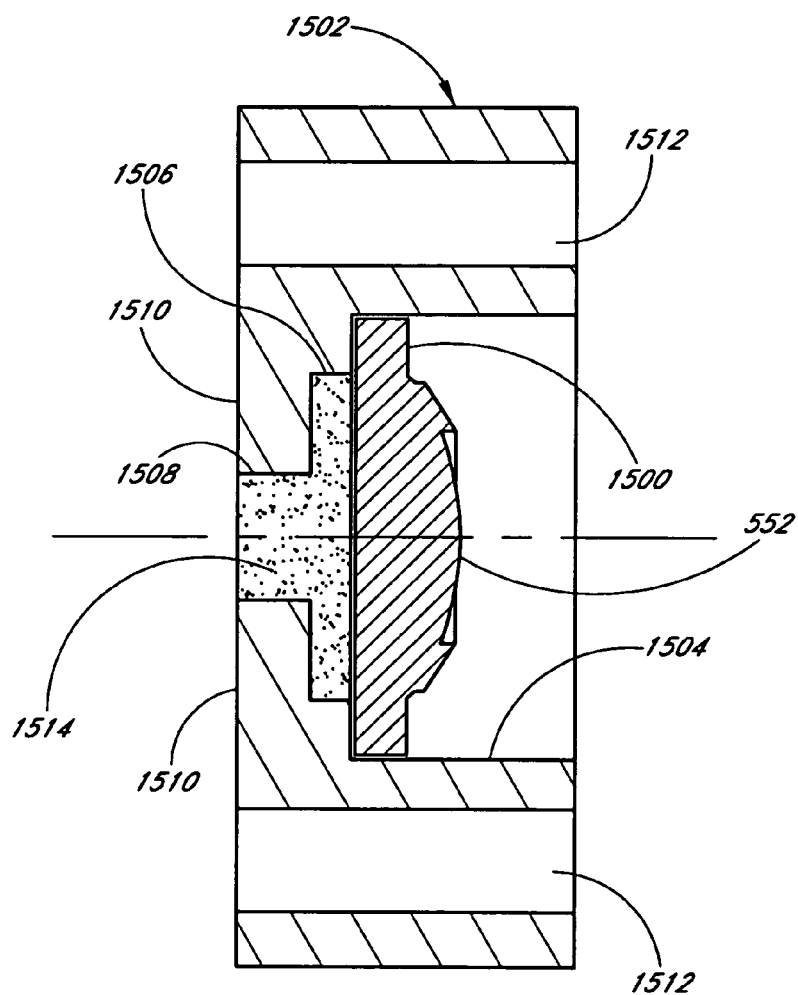
FIG. 51 is another side sectional view of the apparatus and method of FIG. 49.
Figure 52:
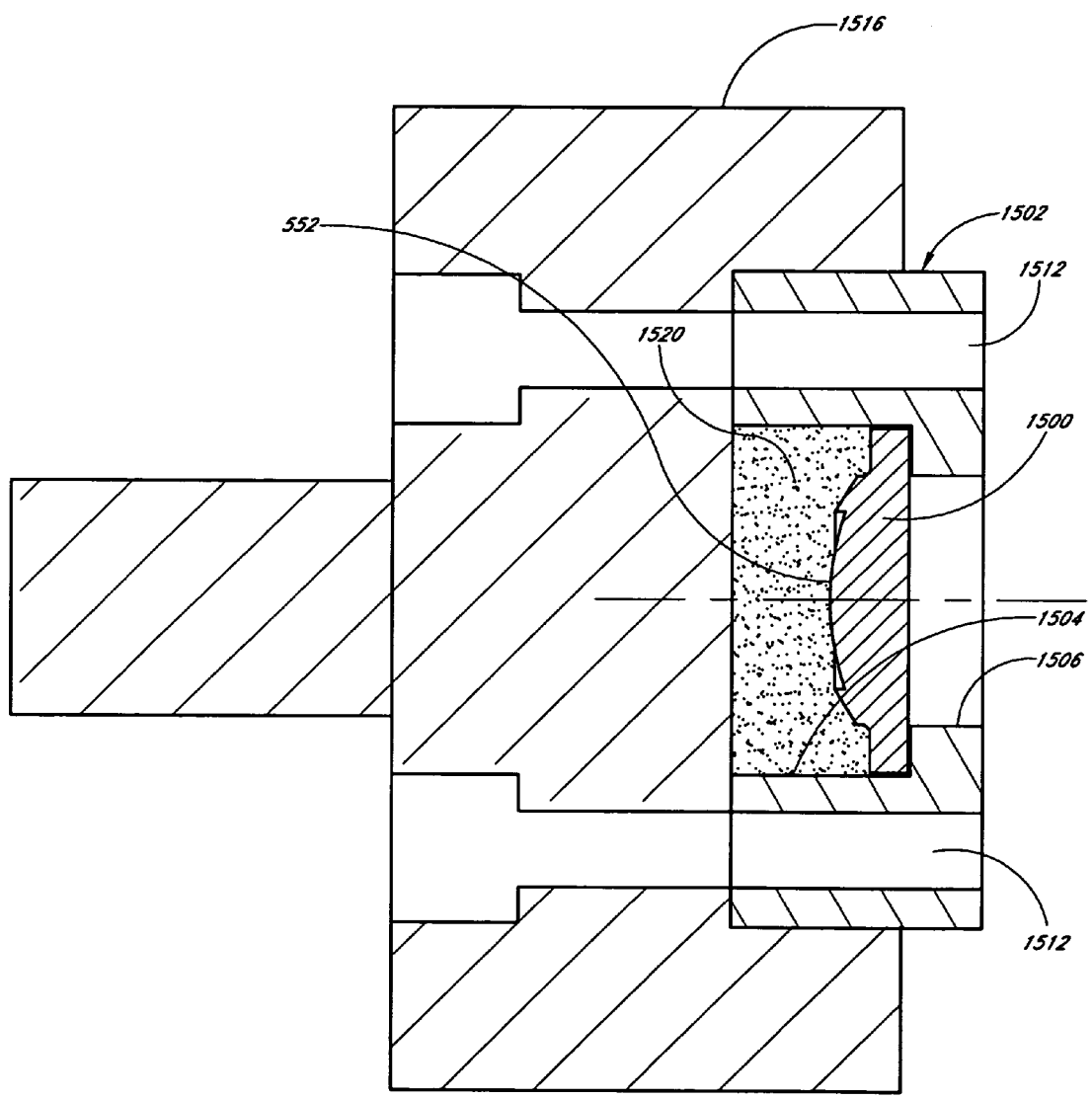
FIG. 52 is another side sectional view of the apparatus and method of FIG. 49.

Once the blank 1500 has been loaded and blocked into the holder 1502, the holder 1502 is secured to a blocker 1516 by bolts or pins (not shown) which fit snugly into the holder bores 1512. The holder bores 1512 align precisely with corresponding blocker bores 1517, by virtue of a snug fit between the blocker bores 1517 and the bolts/pins. The blocker-holder assembly is then loaded into a conventional machine tool, such as a lathe and/or a mill, and one of the first and second center mold cavities 518, 552 (the second cavity 552 is depicted in FIG. 51) is machined from the exposed face of the blank 1500 using conventional machining techniques. The holder 1502 and blank 1500, with the second center mold cavity 552 formed thereon, are then removed from the blocker 1516 as shown in FIG. 51.

Figure 53:
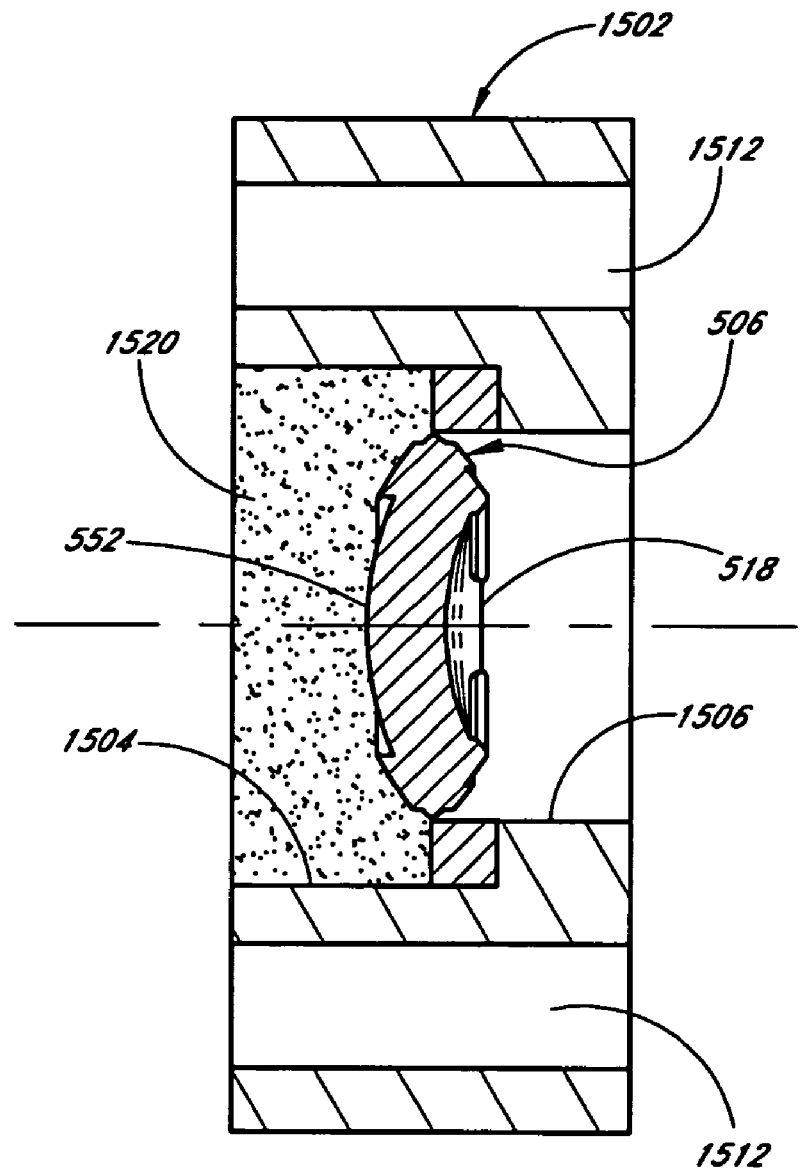
FIG. 53 is another side sectional view of the apparatus and method of FIG. 49.

The main chamber 1504 is then filled with water-soluble wax 1520 forward of the second center mold cavity 552, and the wax 1514 is removed from the secondary chamber 1506 and the passage 1508. Next the holder 1502 is fixed to the blocker 1516 with the as-yet unmodified portion of the blank 1500 facing outward. Upon re-loading the holder-blocker assembly into the machine tool, a portion of the annulus 1510 is then cut away to facilitate tool access to the blank 1500. A series of machining operations are then performed on the blank 1500 until the remaining mold cavity (the first center mold cavity 518 is depicted in FIG. 53) has been formed. The completed center mold 506 may then be removed from the holder 1502.

The machining technique depicted in FIGS. 49-53 is advantageous in that it facilitates fabrication of the center mold 506 (with both the first and second center mold cavities 518, 552) from a single piece of material. While it is possible to machine the first and second center mold cavities 518, 552 from separate pieces of material which are subsequently glued together, such assembly creates a seam in the center mold which can retain contaminants and introduce those contaminants into the mold when forming the lens system 100. In addition, the assembly of the center mold 506 from two halves introduces errors wherein the first and second center mold cavities 518, 552 may be angularly shifted with respect to each other about the optical axis, or wherein the mold cavities 518, 552 are non-concentric (i.e., shifted with respect to each other in a direction orthogonal to the optical axis). The method depicted in FIGS. 49-53 eliminates these problems by retaining the blank 1500 in the holder 1502 throughout the fabrication process and by enforcing precise axial alignment, via forced alignment of the bores 1512 with the blocker bores 1517, when machining of both mold cavities.

In another embodiment, the center mold 506 is formed by a molding process rather than by machining. The center mold 506 may be molded from any of the materials disclosed herein as suitable for forming the lens system 100 itself, including but not limited to silicone, acrylics, polymethylmethacrylate (PMMA), block copolymers of styrene-ethylene-butylene-styrene (C-FLEX) or other styrene-base copolymers, polyvinyl alcohol (PVA), polyurethanes, hydrogels or any other moldable polymers or monomers.

The lens system which is formed when employing the molded center mold 506 may itself be molded from the same material as the center mold 506. For example, the center mold 506 may be molded from silicone, and then the lens system 100 may be molded from silicone by using the mold system 500 with the molded silicone center mold 506.

The center mold 506 can be molded by any suitable conventional techniques. A polished, optical quality initial mold set can be used to make center molds which in turn will produce lens systems with optical quality surfaces on the posterior face of the anterior optic, and the anterior face of the posterior optic. Alternatively (or additionally), the molded center mold can be polished and/or tumbled to produce an optically-accurate center mold.

Figure 54:
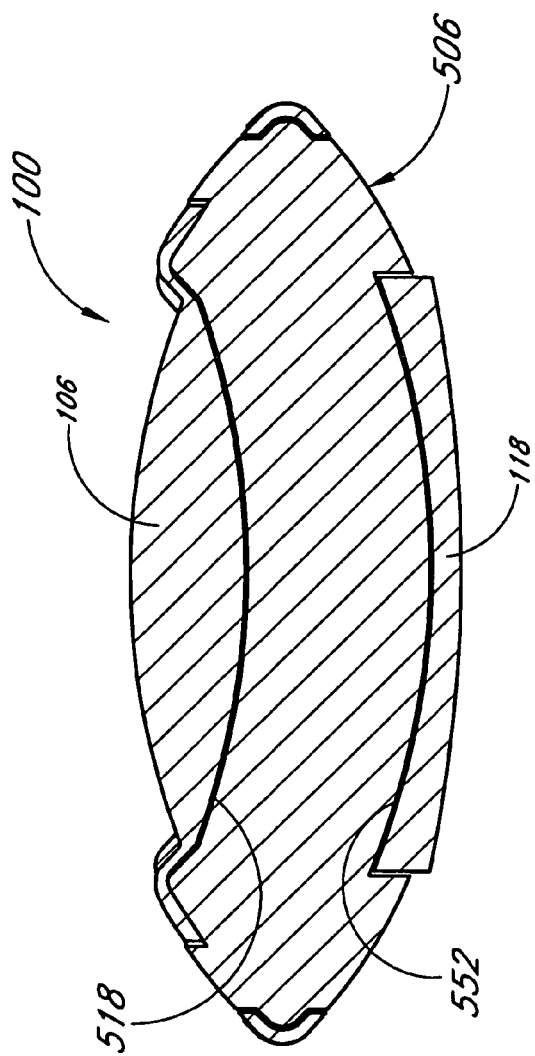
FIG. 54 is a side sectional view of the lens system in position on the center mold.

The molded center mold 506 offers several advantages over a machined center mold. First, it is quicker, cheaper and easier to produce the center mold in large quantities by molding instead of machining. This in turn facilitates leaving the lens system in position on the center mold (see FIG. 54) while the lens system is tumbled, polished and/or deflashed, without incurring undue expense. The presence of the center mold between the optics increases the effectiveness of the tumbling/polishing/deflashing by increasing the hoop strength of the lens system, so that the energy of the impacting tumbling beads is not dissipated in macroscopic deformation of the lens system. Molding also permits softer materials to be employed in forming the center mold, and a softer center mold is more resistant to damage from deflashing tools and processes, resulting in fewer center molds lost to such process-related damage.

VII. Materials/Surface Treatments

Preferred materials for forming the lens system 100 include silicone, acrylics, polymethylmethacrylate (PMMA), block copolymers of styrene-ethylene-butylene-styrene (C-FLEX) or other styrene-base copolymers, polyvinyl alcohol (PVA), polyurethanes, hydrogels or any other suitable polymers or monomers. In addition, any portion of the lens system 100 other than the optic(s) may be formed from stainless steel or a shape-memory alloy such as nitinol or any iron-based shape-memory alloy. Metallic components may be coated with gold to increase biocompatibility. Where feasible, material of a lower Shore A hardness such as 15 A may be used for the optic(s), and material of higher hardness such as 35 A may be used for the balance of the lens system 100. Finally, the optic(s) may be formed from a photosensitive silicone to facilitate post-implantation power adjustment as taught in U.S. patent application Ser. No. 09/416,044, filed Oct. 8, 1999, titled LENSES CAPABLE OF POST-FABRICATION POWER MODIFICATION, the entire contents of which are hereby incorporated by reference herein.

Methyl-methylacrylate monomers may also be blended with any of the non-metallic materials discussed above, to increase the lubricity of the resulting lens system (making the lens system easier to fold or roll for insertion, as discussed further below). The addition of methyl-methylacrylate monomers also increases the strength and transparency of the lens system.

The optics and/or the balance of the lens system 100 can also be formed from layers of differing materials. The layers may be arranged in a simple sandwich fashion, or concentrically. In addition, the layers may include a series of polymer layers, a mix of polymer and metallic layers, or a mix of polymer and monomer layers. In particular, a nitinol ribbon core with a surrounding silicone jacket may be used for any portion of the lens system 100 except for the optics; an acrylic-over-silicone laminate may be employed for the optics. A layered construction may be obtained by pressing/bonding two or more layers together, or deposition or coating processes may be employed.

Where desired, the anterior optic may be formed from a material different from that used to form the posterior optic. This may be done to take advantage of differences between the respective materials in refractive index, mechanical properties or resistance to posterior capsule opacification ("PCO"), or to achieve an appropriate balance of mechanical and optical properties. Additionally, the use of differing materials can increase resistance to intra-lenticular opacification ("ILO"). For example, the material forming the posterior optic may be selected for its resistance to PCO, and/or for its rigidity (so as to form a relatively rigid base for the biasing action of the biasing elements 108, 120, thereby maximizing anterior displacement of the anterior biasing element). Thus, the posterior optic may be formed from acrylic; for example, a hydrophobic acrylic. The material forming the anterior optic may be selected for its high index of refraction, to keep to a minimum the size and weight of the anterior optic (and the lens system as a whole), thereby maximizing the range and speed of motion of the anterior optic in response to a given biasing force. To achieve these properties the anterior optic may be formed from silicone; for example, high-refractive-index silicones (generally, silicones with a refractive index greater than about 1.43, or silicones with a refractive index of about 1.46).

In other embodiments, the anterior optic may be formed from any suitable material (including those disclosed herein), and the posterior optic may be formed from any suitable material (including those disclosed herein) other than the material chosen to form the anterior optic. In one embodiment the anterior optic is formed from silicone and the posterior optic is formed from acrylic; in another embodiment the anterior optic is formed from acrylic and the posterior optic is formed from silicone.

The optics may be considered to be formed from different polymeric materials where no more than about 10 mole percent of recurring units of the polymer employed in the anterior optic are the same as the primary recurring units of the polymer employed in the posterior optic; and/or where no more than about 10 mole percent of recurring units of the polymer employed in the posterior optic are the same as the primary recurring units of the polymer employed in the anterior optic. In general, these conditions are desirable in order for the two materials to have sufficiently different material properties. As used herein, a "primary" recurring unit of a given polymer is the recurring unit which is present in such polymer in the greatest quantity by mole percentage.

In another embodiment, the optics may be considered to be formed from different polymeric materials where no more than about 10 mole percent of recurring units of the polymer employed in the anterior optic are of the same type as the primary recurring units of the polymer employed in the posterior optic; and/or where no more than about 10 mole percent of the recurring units of the polymer employed in the posterior optic are of the same type as the primary recurring units of the polymer employed in the anterior optic. As used herein, recurring units of the same "type" are in the same chemical family (i.e., having the same or similar functionality) or where the backbone of the polymers formed by such recurring units is essentially the same.

In one embodiment, portions of the lens system 100 other than the optic(s) are formed from a shape-memory alloy. This embodiment takes advantage of the exceptional mechanical properties of shape-memory alloys and provides fast, consistent, highly responsive movement of the optic(s) within the capsular bag while minimizing material fatigue in the lens system 100. In one embodiment, one or both of the biasing elements 108, 120 are formed from a shape-memory alloy such as nitinol or any iron-based shape-memory alloy. Due to the flat stress-strain curve of nitinol, such biasing elements provide a highly consistent accommodation force over a wide range of displacement. Furthermore, biasing elements formed from a shape-memory alloy, especially nitinol, retain their spring properties when exposed to heat (as occurs upon implantation into a human eye) while polymeric biasing elements tend to lose their spring properties, thus detracting from the responsiveness of the lens system. For similar reasons, it is advantageous to use shape-memory alloys such as those discussed above in forming any portion of a conventional (non-accommodating) intraocular lens, other than the optic.

Where desired, various coatings are suitable for components of the lens system 100. A heparin coating may be applied to appropriate locations on the lens system 100 to prevent inflammatory cell attachment (ICA) and/or posterior capsule opacification (PCO); naturally, possible locations for such a coating include the posterior biasing element 120 and the posterior face of the posterior viewing element 118. Coatings can also be applied to the lens system 100 to improve biocompatibility; such coatings include "active" coatings like P-15 peptides or RGD peptides, and "passive" coatings such as heparin and other mucopolysaccharides, collagen, fibronectin and laminin. Other coatings, including hirudin, teflon, teflon-like coatings, PVDF, fluorinated polymers, and other coatings which are inert relative to the capsular bag may be employed to increase lubricity at locations (such as the optics and distending members) on the lens system which contact the bag, or Hema or silicone can be used to impart hydrophilic or hydrophobic properties to the lens system 100.

It is also desirable subject the lens system 100 and/or the mold surfaces to a surface passivation process to improve biocompatibility. This may be done via conventional techniques such as chemical etching or plasma treatment.

Furthermore, appropriate surfaces (such as the outer edges/surfaces of the viewing elements, biasing elements, distending members, retention members, etc.) of the lens system 100 can be textured or roughened to improve adhesion to the capsular bag. This may be accomplished by using conventional procedures such as plasma treatment, etching, dipping, vapor deposition, mold surface modification, etc. As a further means of preventing ICA/PCO, a posteriorly-extending perimeter wall (not shown) may be added to the posterior viewing element 118 so as to surround the posterior face of the posterior optic. The wall firmly engages the posterior aspect of the capsular bag and acts as a physical barrier to the progress of cellular ingrowth occurring on the interior surface of the capsular bag. Finally, the relatively thick cross-section of the preferred anterior viewing element 118 (see FIGS. 9, 10) ensures that it will firmly abut the posterior capsule with no localized flexing. Thus, with its relatively sharp rim, the posterior face of the preferred posterior viewing element 118 can itself serve as a barrier to cellular ingrowth and ICA/PCO. In order to achieve this effect, the posterior viewing element 118 is preferably made thicker than conventional intraocular lenses. As an alternative or supplement to a thick posterior viewing element, cell growth may be inhibited by forming a pronounced, posteriorly-extending perimeter rim on the posterior face of the posterior viewing element 118. Upon implantation of the lens system 100, the rim firmly abuts the inner surface of the capsular bag 58 and acts as a physical barrier to cell growth between the posterior face of the posterior viewing element 118 and the capsular bag 58.

The selected material and lens configuration should be able to withstand secondary operations after molding/casting such as polishing, cleaning and sterilization processes involving the use of an autoclave, or ethylene oxide or radiation. After the mold is opened, the lens should undergo deflashing, polishing and cleaning operations, which typically involve a chemical or mechanical process, or a combination thereof. Suitable mechanical processes include tumbling, shaking and vibration; a tumbling process may involve the use of a barrel with varying grades of glass beads, fluids such as alcohol or water and polishing compounds such as aluminum oxides. Process rates are material dependent; for example, a tumbling process for silicone should utilize a 6" diameter barrel moving at 30-100 RPM. It is contemplated that several different steps of polishing and cleaning may be employed before the final surface quality is achieved.

Figure 34:
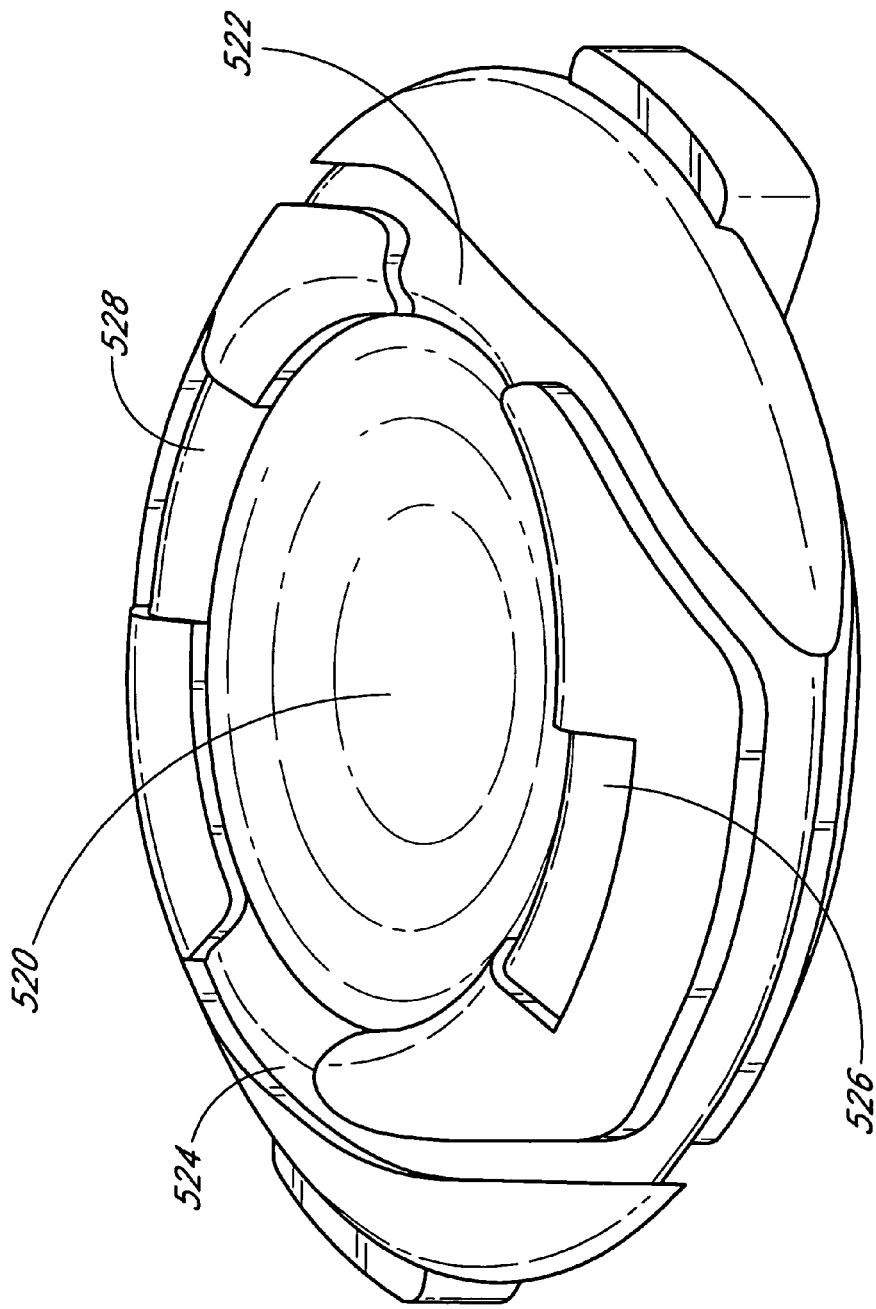
FIG. 34 is a perspective view of the center mold portion.
Figure 34A:
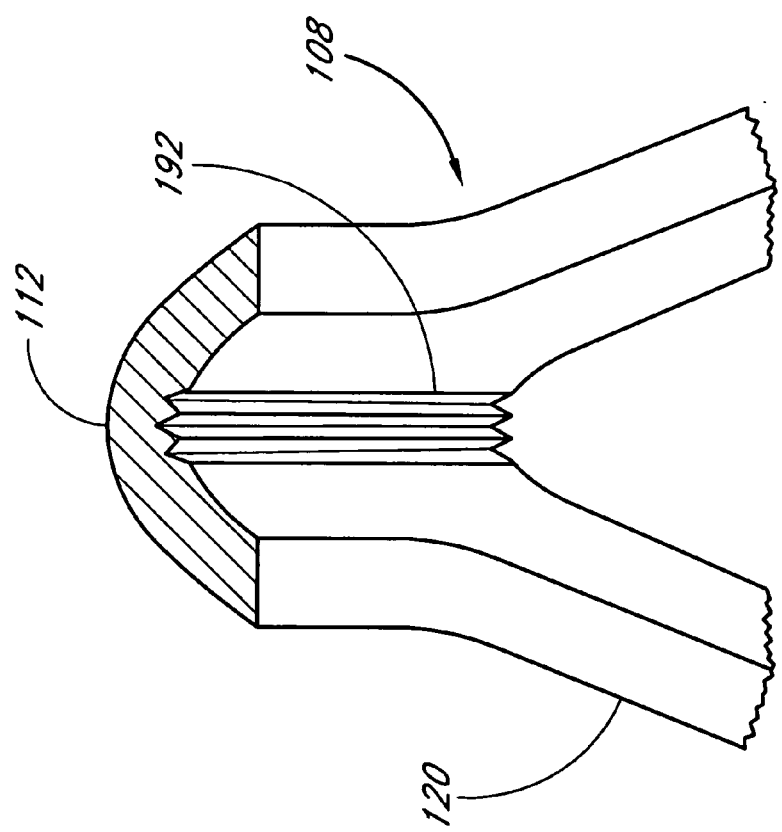
FIG. 34A is a partial cross sectional view of an apex of the lens system, showing a set of expansion grooves formed therein.

In one embodiment, the lens system 100 is held in a fixture to provide increased separation between, and improved process effect on, the anterior and posterior viewing elements during the deflashing/polishing/cleaning operations. In another embodiment, the lens system 100 is everted or turned "inside-out" so that the inner faces of the viewing elements are better exposed during a portion of the deflashing/polishing/cleaning. FIG. 34A shows a number of expansion grooves 192 which may be formed in the underside of the apices 112, 116 of the lens system 100 to facilitate eversion of the lens system 100 without damaging or tearing the apices or the anterior/posterior biasing elements 108, 120. For the same reasons similar expansion grooves may be formed on the opposite sides (i.e., the outer surfaces) of the apices 112, 116 instead of or in addition to the location of grooves on the underside.

A curing process may also be desirable in manufacturing the lens system 100. If the lens system is produced from silicone entirely at room temperature, the curing time can be as long as several days. If the mold is maintained at about 50 degrees C., the curing time is reduced to about 24 hours; if the mold is preheated to 100-200 degrees C. the curing time can be as short as about 3-15 minutes. Of course, the time-temperature combinations vary for other materials.

VIII. Multiple-Piece and Other Embodiments

Figure 35:
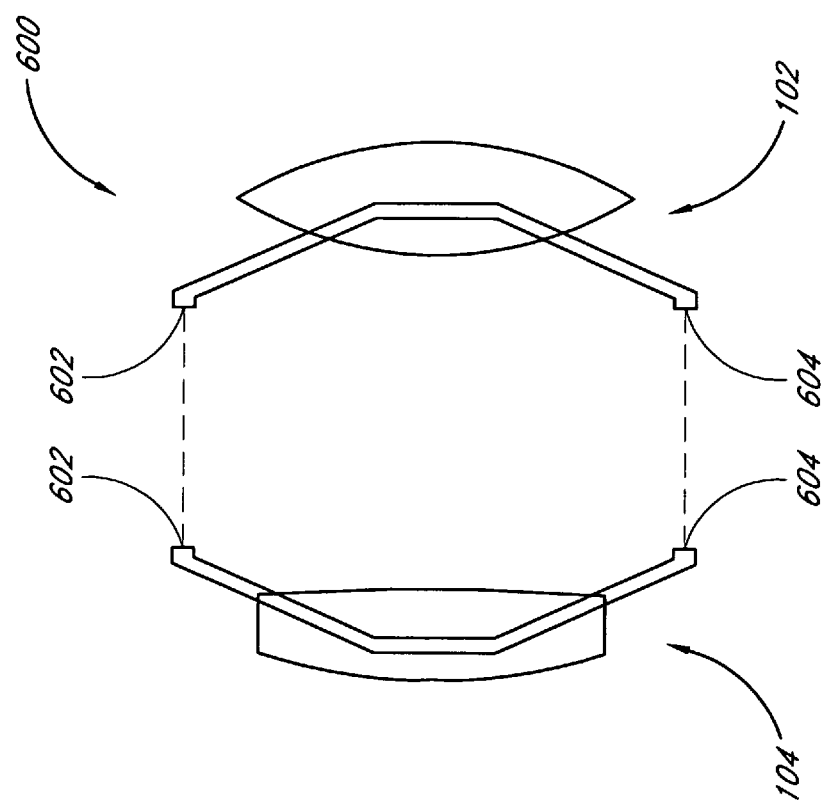
FIG. 35 is a schematic view of another embodiment of the lens system.

FIG. 35 is a schematic view of a two-piece embodiment 600 of the lens system. In this embodiment the anterior portion 102 and the posterior portion 104 are formed as separate pieces which are intended for separate insertion into the capsular bag and subsequent assembly therein. In one embodiment, each of the anterior and posterior portions 102, 104 is rolled or folded before insertion into the capsular bag. (The insertion procedure is discussed in further detail below.) The anterior portion 102 and posterior portion 104 are represented schematically as they may generally comprise any anterior-portion or posterior-portion structure disclosed herein; for example, they may simply comprise the lens system 100 shown in FIGS. 3-17, bisected along the line/plane A-A shown in FIG. 4. The anterior portion 102 and posterior portion 104 of the two-piece lens system 600 will include first and second abutments 602, 604 which are intended to be placed in abutting relation (thus forming the first and second apices of the lens system) during the assembly procedure. The first and second abutments 602, 604 may include engagement members (not shown), such as matching projections and recesses, to facilitate alignment and assembly of the anterior and posterior portions 102, 104.

As a further alternative, the anterior and posterior portions 102, 104 of the lens system 600 may be hingedly connected at one of the abutments 602, 604 and unconnected at the other, to allow sequential (but nonetheless partially assembled) insertion of the portions 102, 104 into the capsular bag. The individual portions may be separately rolled or folded before insertion. The two portions 102, 104 are "swung" together and joined at the unconnected abutment to form the finished lens system after both portions have been inserted and allowed to unfold/unroll as needed.

Figure 36:
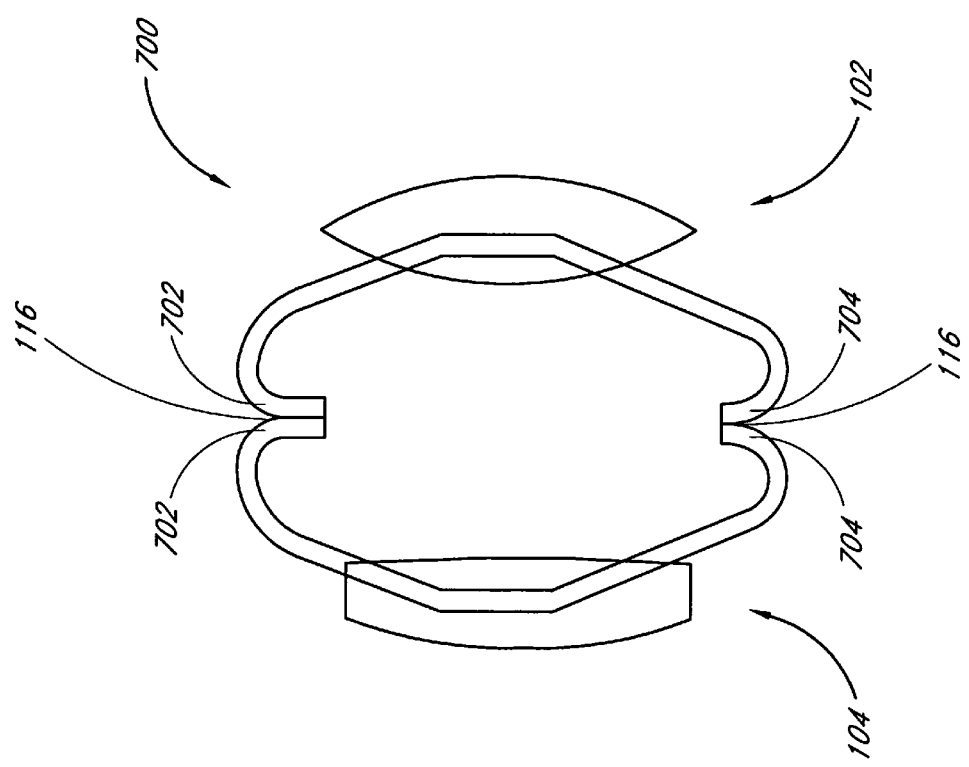
FIG. 36 is a schematic view of another embodiment of the lens system.

FIG. 36 depicts schematically another embodiment 700 of a two-piece lens system. The lens system 700 is desirably similar to the lens system 600 shown in FIG. 35, except for the formation of relatively larger, curled abutments 702, 704 which are assembled to form the apices 112, 116 of the system 700.

Figure 38:
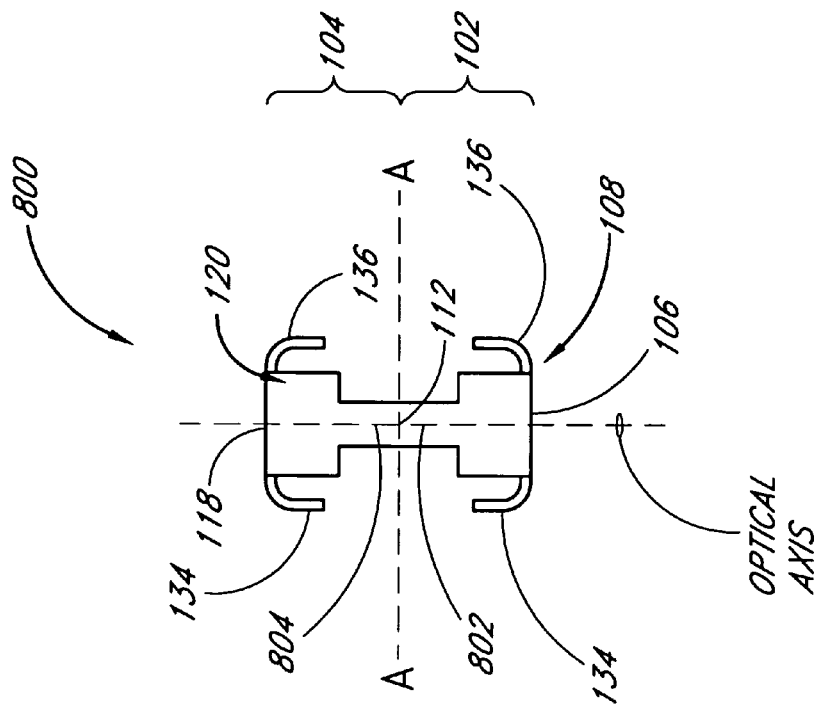
FIG. 38 is a top view of another embodiment of the lens system.
Figure 37:
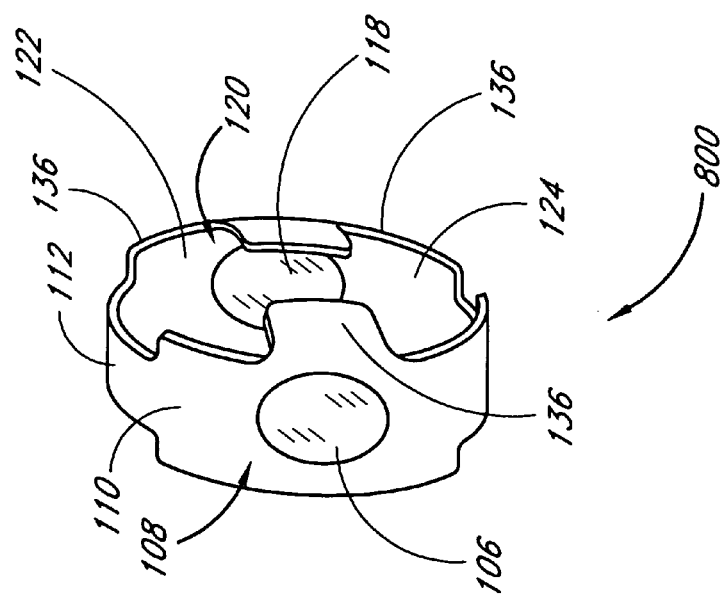
FIG. 37 is a perspective view of another embodiment of the lens system.

FIGS. 37 and 38 show a further embodiment 800 of the lens system, in which the anterior and posterior biasing elements 108, 120 comprise integral "band" like members forming, respectively, the first and second anterior translation members 110, 114 and the first and second posterior translation members 122, 124. The biasing elements 108, 120 also form reduced-width portions 802, 804 which meet at the apices of the lens system 800 and provide regions of high flexibility to facilitate sufficient accommodative movement. The depicted distending portion 132 includes three pairs of distending members 134, 136 which have a curved configuration but nonetheless project generally away from the optical axis.

Figure 38A:
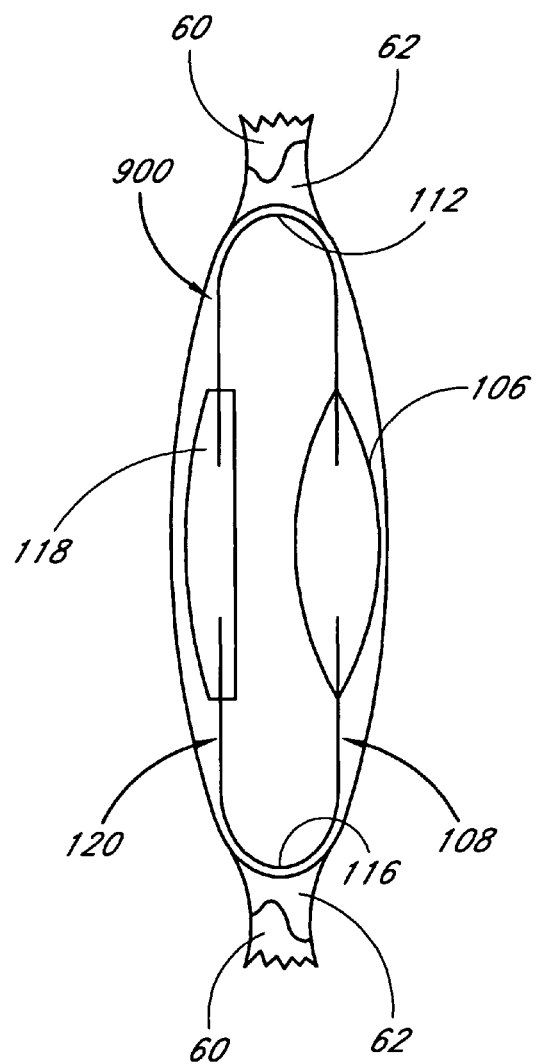
FIG. 38A is a schematic view of another embodiment of the lens system, as implanted in the capsular bag.
Figure 38B:
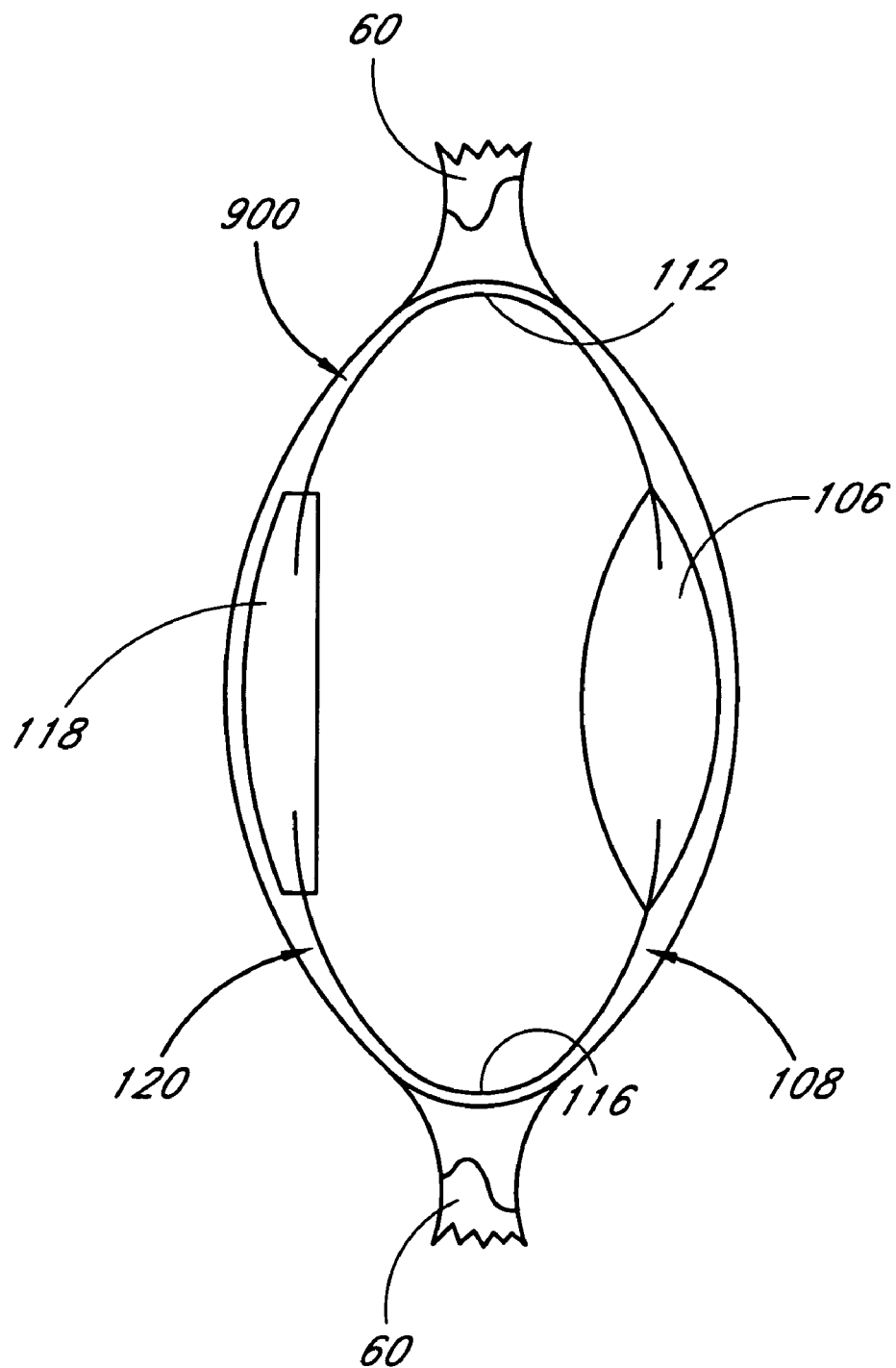
FIG. 38B is a schematic view of the embodiment of FIG. 38A, in the accommodated state.

FIGS. 38A and 38B depict another embodiment 900 of the lens system, as implanted in the capsular bag 58. The embodiment shown in FIGS. 38A and 38B may be similar to any of the embodiments described above, except that the biasing elements 108, 120 are dimensioned so that the apices 112, 116 abut the zonules 62 and ciliary muscles 60 when in the unaccommodated state as seen in FIG. 38A. In addition, the lens system 900 is configured such that it will remain in the unaccommodated state in the absence of external forces. Thus, when the ciliary muscles 60 contract, the muscles 60 push the apices 112, 116 closer together, causing the biasing elements 108, 120 to bow out and the viewing elements 106, 118 to separate and attain the accommodated state as shown in FIG. 38B. When the ciliary muscles 60 relax and reduce/eliminate the force applied to the apices 112, 116 the biasing elements 108, 120 move the lens system 900 to the unaccommodated state depicted in FIG. 38A.

FIGS. 38C and 38D depict biasers 1000 which may be used bias the lens system 100 toward the accommodated or unaccommodated state, depending on the desired operating characteristics of the lens system. It is therefore contemplated that the biasers 1000 may be used with any of the embodiments of the lens system 100 disclosed herein. The bias provided by the biasers 1000 may be employed instead of, or in addition to, any bias generated by the biasing elements 108, 120. In one embodiment (see FIG. 38C), the biasers 1000 may comprise U-shaped spring members having apices 1002 located adjacent the apices 112, 116 of the lens system 100. In another embodiment (see FIG. 38D), the biasers 1000 may comprise any suitable longitudinal-compression springs which span the apices 112, 116 and interconnect the anterior and posterior biasing elements 108, 120. By appropriately selecting the spring constants and dimensions of the biasers 1000 (in the case of U-shaped springs, the apex angle and arm length; in the case of longitudinal-compression springs, their overall length), the biasers 1000 can impart to the lens system 100 a bias toward the accommodated or unaccommodated state as desired.

The biasers 1000 may be formed from any of the materials disclosed herein as suitable for constructing the lens system 100 itself. The material(s) selected for the biasers 1000 may be the same as, or different from, the material(s) which are used to form the remainder of the particular lens system 100 to which the biasers 1000 are connected. The number of biasers 1000 used in a particular lens system 100 may be equal to or less than the number of apices formed by the biasing elements of the lens system 100.

Figure 38E:
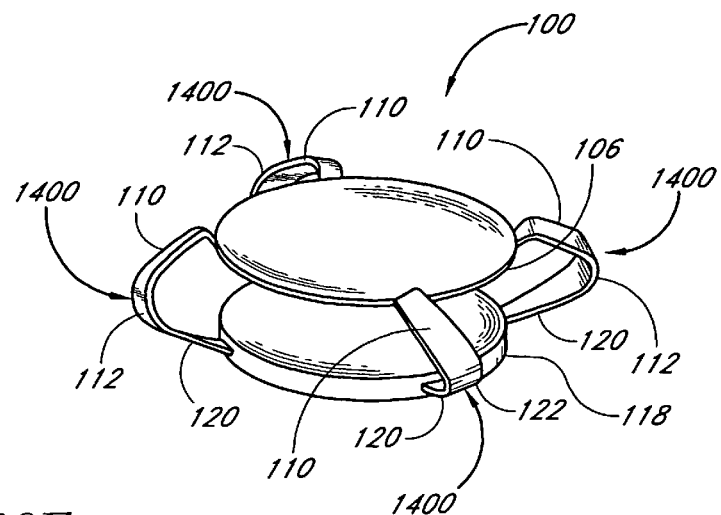
FIG. 38E is a perspective view of another embodiment of the lens system.

FIG. 38E depicts a further embodiment of the lens system 100 in which the anterior translation members 110 and the posterior translation members 120 are paired in a number (in the example depicted, four) of separate positioners 1400 which are radially spaced, preferably equally radially spaced, about the optical axis. In the depicted embodiment, the anterior and posterior translation members 110, 120 connect directly to the periphery of the viewing elements 106, 118; however, in other embodiments any of the connection techniques disclosed herein may be employed. As shown, the anterior translation members 100 preferably extend anteriorly from the periphery of the anterior viewing element before bending and extending posteriorly toward the apex/apices 112. As discussed above, this configuration is advantageous for promotion of fluid flow through an opening formed in the anterior aspect of the capsular bag 58. It has been found that the lens configuration shown in FIG. 38E is well suited for the folding technique shown in FIGS. 40A and 40B below. In additional embodiments, the lens system 100 shown in FIG. 38E may incorporate any other suitable features of the other embodiments of the lens system 100 disclosed herein, such as but not limited to the distending members and/or retention members detailed above.

IX. Implantation Methods

Various techniques may be employed in implanting the various embodiments of the lens system in the eye of a patient. The physician can first access the anterior aspect of the capsular bag 58 via any appropriate technique. Next, the physician incises the anterior of the bag; this may involve making the circular opening 66 shown in FIGS. 21 and 22, or the physician may make a "dumbbell" shaped incision by forming two small circular incisions or openings and connecting them with a third, straight-line incision. The natural lens is then removed from the capsular bag via any of various known techniques, such as phacoemulsification, cryogenic and/or radiative methods. To inhibit further cell growth, it is desirable to remove or kill all remaining epithelial cells. This can be achieved via cryogenic and/or radiative techniques, antimetabolites, chemical and osmotic agents. It is also possible to administer agents such as P15 to limit cell growth by sequestering the cells.

In the next step, the physician implants the lens system into the capsular bag. Where the lens system comprises separate anterior and posterior portions, the physician first folds or rolls the posterior portion and places it in the capsular bag through the anterior opening. After allowing the posterior portion to unroll/unfold, the physician adjusts the positioning of the posterior portion until it is within satisfactory limits. Next the physician rolls/folds and implants the anterior portion in a similar manner, and aligns and assembles the anterior portion to the posterior portion as needed, by causing engagement of mating portions, etc. formed on the anterior and posterior portions.

Where the lens system comprises anterior and posterior portions which are partially assembled or partially integral (see discussion above in the section titled MULTIPLE-PIECE AND OTHER EMBODIMENTS), the physician employs appropriate implantation procedures, subsequently folding/rolling and inserting those portions of the lens system that are separately foldable/rollable. In one embodiment, the physician first rolls/folds one portion of the partially assembled lens system and then inserts that portion. The physician then rolls/folds another portion of the partially assembled lens system and the inserts that portion. This is repeated until the entire system is inside the capsular bag, whereupon the physician completes the assembly of the portions and aligns the lens system as needed. In another embodiment, the physician first rolls/folds all of the separately rollable/foldable portions of the partially assembled lens system and then inserts the rolled/folded system into the capsular bag. Once the lens system is in the capsular bag, the physician completes the assembly of the portions and aligns the lens system as needed.

Figure 39A:
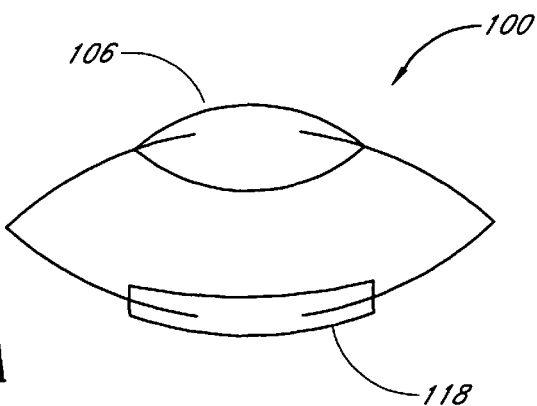
FIGS. 39A-39B are a series of schematic views of an insertion technique for use in connection with the lens system
Figure 39B:
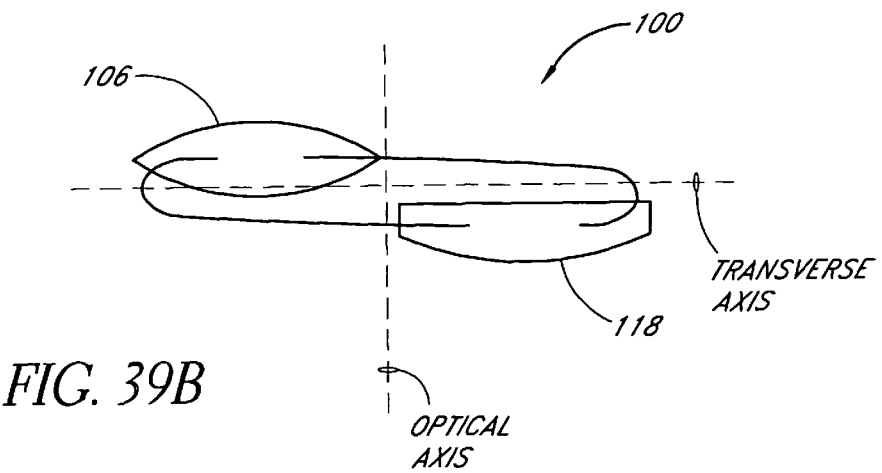

It is contemplated that conventional intraocular lens folding devices, injectors, syringes and/or shooters can be used to insert any of the lens systems disclosed herein. A preferred folding/rolling technique is depicted in FIGS. 39A-39B, where the lens system 100 is shown first in its normal condition (A). The anterior and posterior viewing elements 106, 118 are manipulated to place the lens system 100 in a low-profile condition (B), in which the viewing elements 106, 118 are out of axial alignment and are preferably situated so that no portion of the anterior viewing element 106 overlaps any portion of the posterior viewing element 118, as viewed along the optical axis. In the low-profile position (B), the thickness of the lens system 100 is minimized because the viewing elements 106, 118 are not "stacked" on top of each other, but instead have a side-by-side configuration. From the low-profile condition (B) the viewing elements 106, 118 and/or other portions of the lens system 100 can be folded or rolled generally about the transverse axis, or an axis parallel thereto. Alternatively, the lens system could be folded or rolled about the lateral axis or an axis parallel thereto. Upon folding/rolling, the lens system 100 is placed in a standard insertion tool as discussed above and is inserted into the eye.

When the lens system 100 is in the low-profile condition (B), the system may be temporarily held in that condition by the use of dissolvable sutures, or a simple clip which is detachable or manufactured from a dissolvable material. The sutures or clip hold the lens system in the low-profile condition during insertion and for a desired time after insertion. By temporarily holding the lens system in the low-profile condition after insertion, the sutures or clip provide time for fibrin formation on the edges of the lens system which, after the lens system departs from the low-profile condition, may advantageously bind the lens system to the inner surface of the capsular bag.

The physician next performs any adjustment steps which are facilitated by the particular lens system being implanted. Where the lens system is configured to receive the optic(s) in "open" frame members, the physician first observes/measures/determines the post-implantation shape taken on by the capsular bag and lens system in the accommodated and/or unaccommodated states and select(s) the optics which will provide the proper lens-system performance in light of the observed shape characteristics and/or available information on the patient's optical disorder. The physician then installs the optic(s) in the respective frame member(s); the installation takes place either in the capsular bag itself or upon temporary removal of the needed portion(s) of the lens system from the bag. If any portion is removed, a final installation and assembly is then performed with the optic(s) in place in the frame member(s).

Where the optic(s) is/are formed from an appropriate photosensitive silicone as discussed above, the physician illuminates the optic(s) (either anterior or posterior or both) with an energy source such as a laser until they attain the needed physical dimensions or refractive index. The physician may perform an intervening step of observing/measuring/determining the post-implantation shape taken on by the capsular bag and lens system in the accommodated and/or unaccommodated states, before determining any needed changes in the physical dimensions or refractive index of the optic(s) in question.

Figure 40:
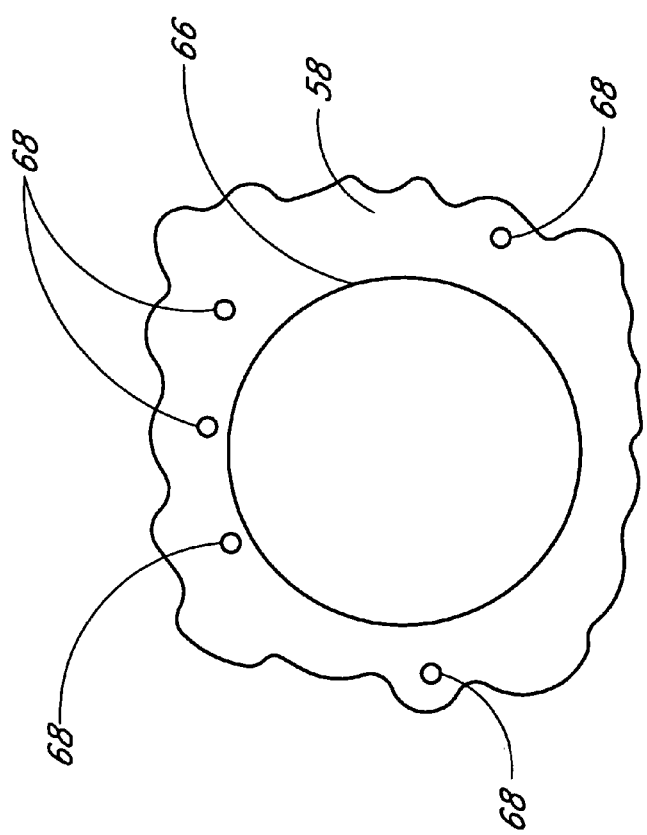
FIG. 40 is a schematic view of fluid-flow openings formed in the anterior aspect of the capsular bag.

FIG. 40 depicts a technique which may be employed during lens implantation to create a fluid flow path between the interior of the capsular bag 58 and the region of the eye anterior of the capsular bag 58. The physician forms a number of fluid-flow openings 68 in the anterior aspect of the capsular bag 58, at any desired location around the anterior opening 66. The fluid-flow openings 68 ensure that the desired flow path exists, even if a seal is created between the anterior opening 66 and a viewing element of the lens system.

Where an accommodating lens system is implanted, the openings 68 create a fluid flow path from the region between the viewing elements of the implanted lens system, and the region of the eye anterior of the capsular bag 58. However, the technique is equally useful for use with conventional (non-accommodating) intraocular lenses.

Figure 40A:
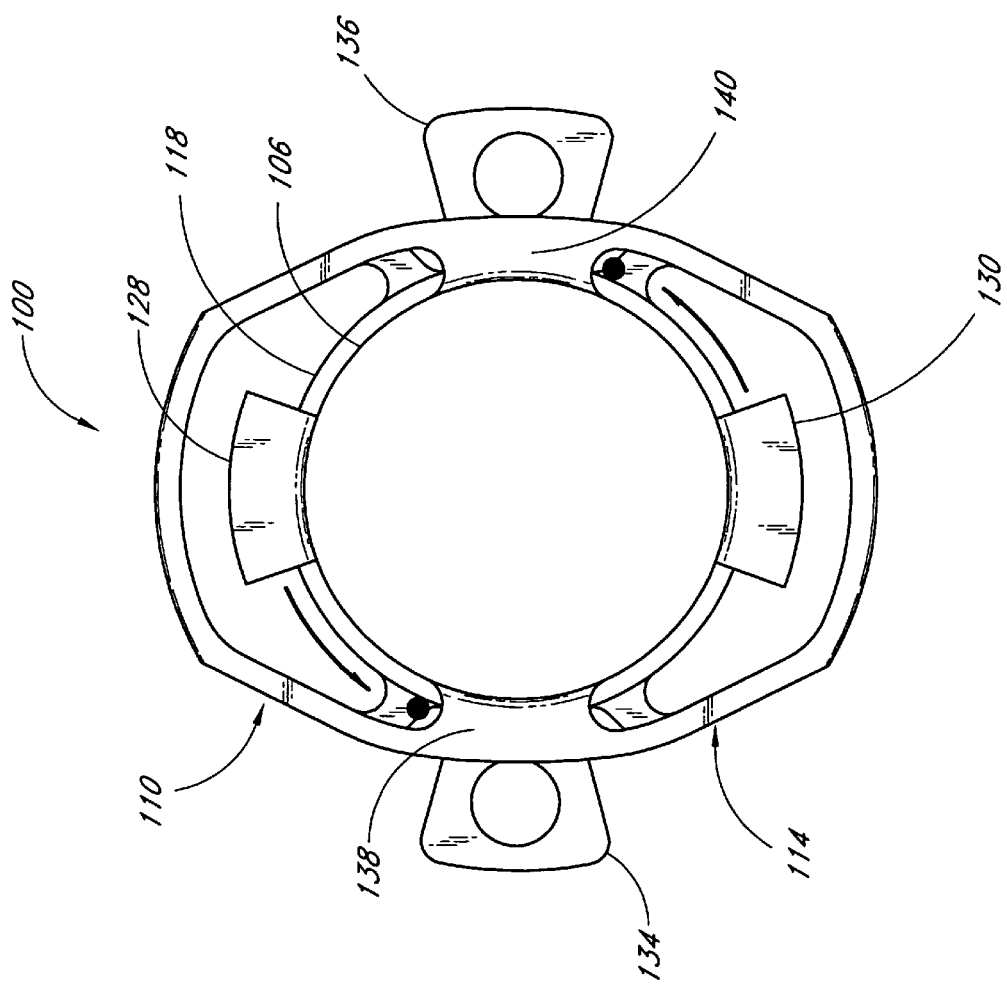
FIG. 40A is a front view of the lens system, illustrating one stage of a folding technique for use with the lens system.
Figure 40B:
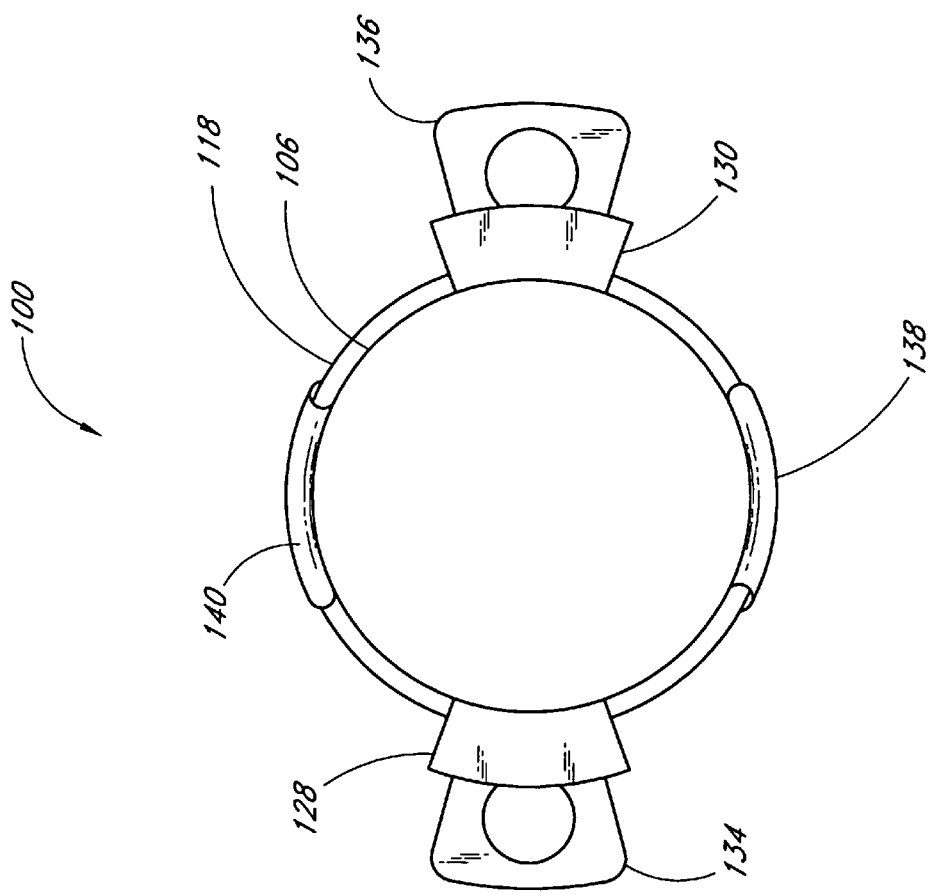
FIG. 40B is a front view of the lens system, illustrating another stage of the folding technique.

FIGS. 40A and 40B illustrate another embodiment of a method of folding the lens system 100. In this method the anterior viewing element 106 is rotated approximately 90 degrees about the optical axis with respect to the posterior viewing element 118. This rotation may be accomplished by applying rotational force to the upper edge of the first transition member 138 and the lower edge of the second transition member 140 (or vice versa), as indicated by the dots and arrows in FIG. 40A, while holding the posterior viewing element 118 stationary, preferably by gripping or clamping the distending members 134, 136. Alternatively, rotational force may be applied in a similar manner to a right edge of one of the retention members 128, 130 and to a left edge of the other of the retention members while holding the posterior viewing element 118 stationary. As still further alternatives, the anterior viewing element 106 could be held stationary while rotational force is applied to the posterior viewing element 118, at an upper edge of one of the distending members 134, 136 and at a lower edge of the other of the distending members; or both the anterior and posterior viewing elements 106, 118 could be rotated with respect to each other.

Preferably, the viewing elements 106, 118 are spread apart somewhat as the rotation is applied to the lens system so that the translation members and apices are drawn into the space between the viewing elements 106, 118 in response to the rotational force. Once the anterior viewing element 106 has been rotated approximately 90 degrees about the optical axis with respect to the posterior viewing element 118, the lens system 100 takes on the configuration shown in FIG. 40B, with the retention members 128, 130 generally radially aligned with the distending members 134, 136 and the translation members and apices disposed between the viewing elements 106, 118. This configuration is advantageous for inserting the lens system 100 into the capsular bag 58 because it reduces the insertion profile of the lens system 100 while storing a large amount of potential energy in the translation members. From the folded configuration the translation members thus exert a high "rebound" force when the lens system has been inserted to the capsular bag 58, causing the lens system to overcome any self-adhesion and spring back to the unfolded configuration shown in FIG. 40A without need for additional manipulation by the physician.

Figure 40C:
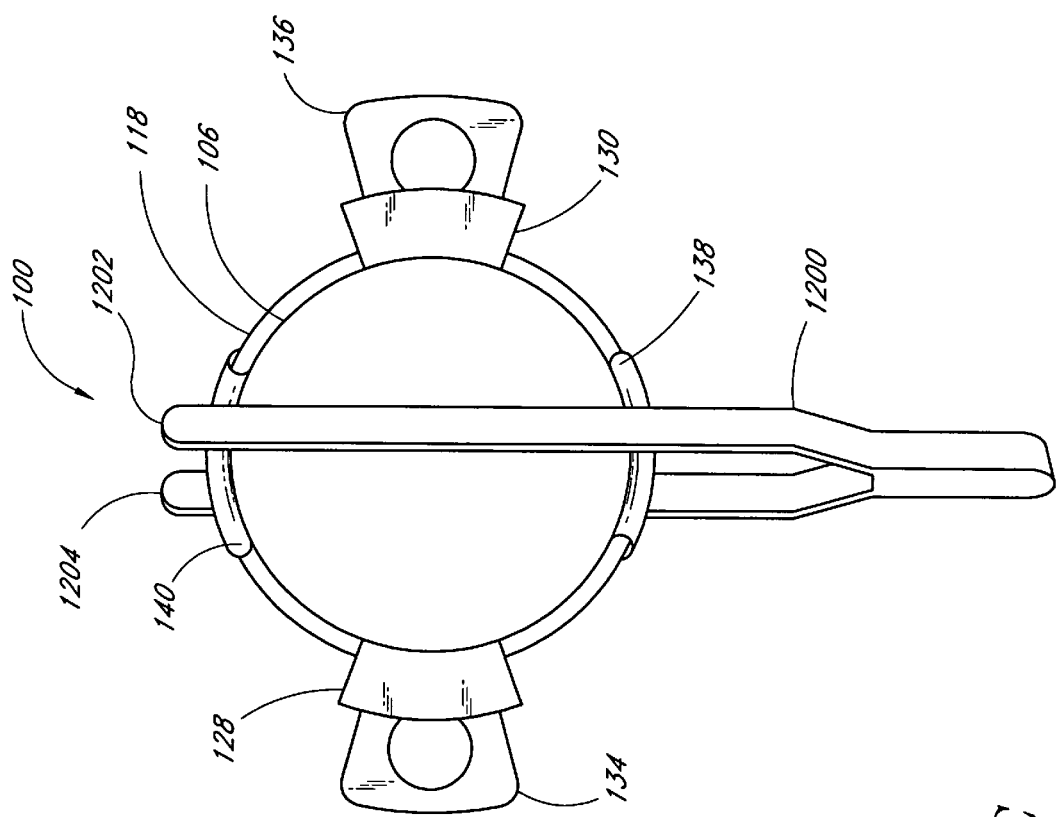
FIG. 40C illustrates another stage of the folding technique.

Once the lens system 100 is in the folded configuration shown in FIG. 40B, it may be further folded and/or inserted into the capsular bag 58 by any suitable methods presently known in the art or hereafter developed. For example, as shown in FIG. 40C the folding method may further comprise inserting the folded lens system 100 between the prongs 1202, 1204 of a clip 1200, preferably with the prongs 1202, 1204 oriented to extend along the transition members 138, 140, or along the retention members 128, 130 and the distending members 134, 136.

FIGS. 40D-40F illustrate the use of jaws 1250, 1252 of a pliers or forceps to fold the lens system 100 as it is held in the clip 1200. (FIGS. 40D-40F show an end view of the clip-lens system assembly with the jaws 1250, 1252 shown in section for clarity.) As shown in FIGS. 40D and 40E, the edges of the jaws 1250, 1252 are urged against one of the anterior and posterior viewing elements 106, 118 while the jaws 1250, 1252 straddle the prong 1202 of the clip 1200. The resulting three-point load on the lens system 1200 causes it to fold in half as shown in FIG. 40E. As the lens system 100 approaches the folded configuration shown in FIG. 40F, the jaws 1250, 1252 slide into a pincer orientation with respect to the lens system 100, characterized by contact between the inner faces 1254, 1256 of the jaws 1250, 1252 and the anterior viewing element 106 or posterior viewing element 118. With such a pincer orientation established, the forceps may be used to grip and compress the lens system with inward-directed pressure and the clip 1200 can be withdrawn, as shown in FIG. 40F. With the lens system 100 thus folded, it can be inserted to the capsular bag 58 by any suitable method presently known in the art or hereafter developed.

Figure 40G:
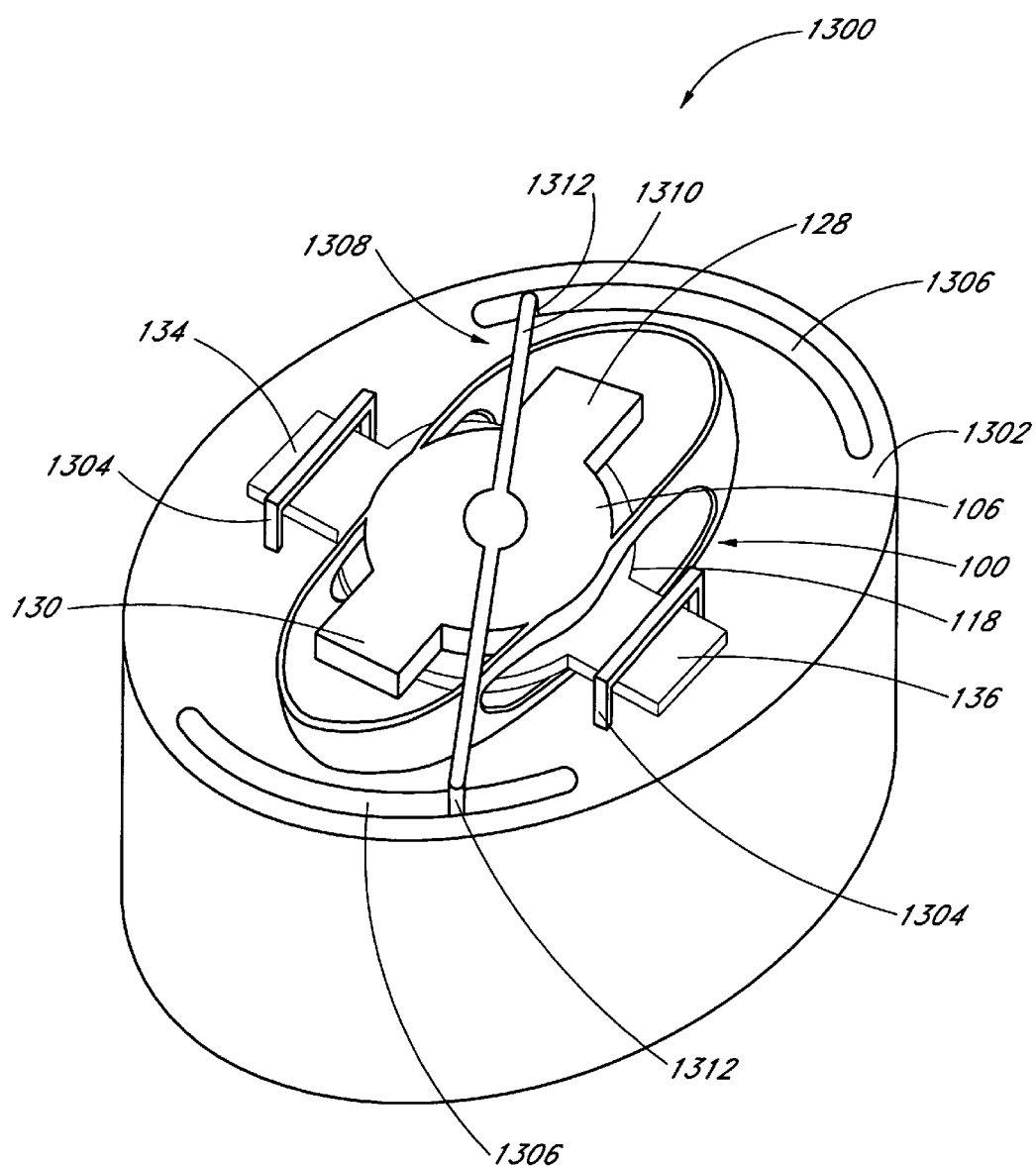
FIG. 40G is a perspective view of a folding tool for use with the lens system.

FIG. 40G depicts a folding tool 1300 which may be employed to fold the lens system 100 as discussed above in connection with FIGS. 40A and 40B. The tool 1300 includes a base 1302 with brackets 1304 which hold the lens system 100 to the base 1302 by gripping the distending members 134, 136. Formed within the base 1302 are arcuate guides 1306. The tool further comprises a rotor 1308 which in turn comprises a horizontal rod 1310 and integrally formed vertical rods 1312. The vertical rods 1312 engage the arcuate guides 1306, both of which have a geometric center on the optical axis of the lens system 100. The vertical rods 1312 and the arcuate guides 1306 thus coact to allow the horizontal rod to rotate at least 90 degrees about the optical axis of the lens system 100. The horizontal rod 1310 is fixed with respect to the anterior viewing element 106 of the lens system 100 so as to prevent substantially no relative angular movement between the rod 1310 and the anterior viewing element 106 as the rod 1310 (and, in turn, the anterior viewing element 106) rotates about the optical axis of the lens system 100. This fixed relationship may be established by adhesives and/or projections (not shown) which extend downward from the horizontal rod 1308 and bear against the upper edge of one of the transition members 138, 140 and against the lower edge of the other of the transition members as shown in FIG. 40A. As an alternative or as a supplement to this arrangement, the projections may bear against the retention members 128, 130 in a similar manner as discussed above.

Thus, when the rotor 1308 is advanced through its range of angular motion about the optical axis of the lens system 100, it forces the anterior viewing element 106 to rotate in concert therewith about the optical axis, folding the lens system as discussed above in connection with FIGS. 40A and 40B. It is further contemplated that the folding tool 1300 may comprise the lower half of a package in which the lens system is stored and/or shipped to a customer, to minimize the labor involved in folding the lens system at the point of use. Preferably, the lens system is stored in the tool 1300 in the unfolded configuration, so as to avoid undesirable deformation of the lens system.

X. Thin Optic Configurations

In some circumstances it is advantageous to make one or more of the optics of the lens system relatively thin, in order to facilitate rolling or folding, or to reduce the overall size or mass of the lens system. Discussed below are various optic configurations which facilitate a thinner profile for the optic; any one of these configurations may be employed as well as any suitable combination of two or more of the disclosed configurations.

One suitable technique is to employ a material having a relatively high index of refraction to construct one or more of the optics. In one embodiment, the optic material has an index of refraction higher than that of silicone. In another embodiment, the material has an index of refraction higher than about 1.43. In further embodiments, the optic material has an index of refraction of about 1.46, 1.49 or 1.55. In still further embodiments, the optic material has an index of refraction of about 1.43 to 1.55. By employing a material with a relatively high index of refraction, the curvature of the optic can be reduced (in other words, the radius/radii of curvature can be increased) thereby reducing the thickness of the optic without loss of focal power.

Figure 41:
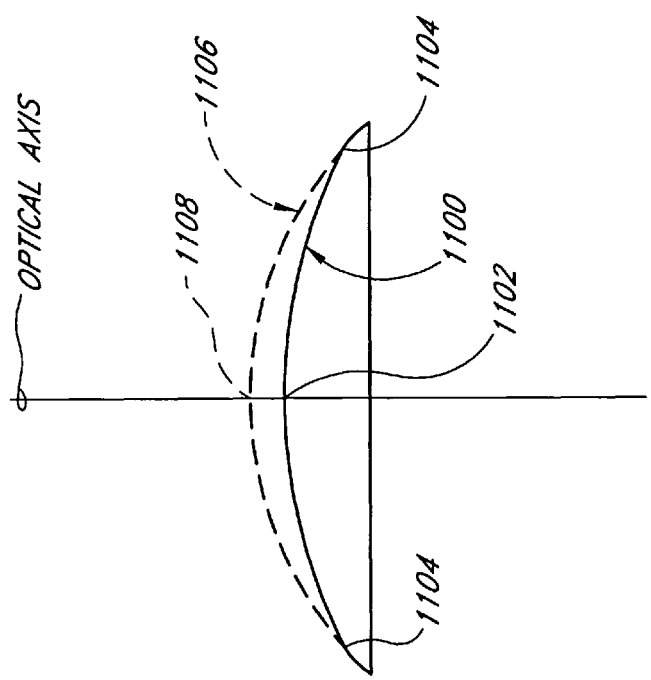
FIG. 41 is a sectional view of an aspheric optic for use with the lens system.

A thinner optic can also be facilitated by forming one or more of the surfaces of one or more of the optics as an aspheric surface, while maintaining the focal power of the optic. As shown in FIG. 41, an aspheric, convex optic surface 1100 can be formed with the same radius of curvature (as a comparable-power spherical surface) at the vertex 1102 of the surface 1100 and a longer radius of curvature (with a common center point) at its periphery 1104, creating a thinner optic without sacrificing focal power. This contrasts with a spherical optic surface 1106, which is thicker at its vertex 1108 than is the aspheric surface 1102. In one embodiment, the thickness of the optic is reduced by about 19% at the vertex relative to a comparable-power spherical optic. It is contemplated that thinner, aspheric concave optic surfaces may be used as well. A further advantage of an aspheric optic surface is that it provides better image quality with fewer aberrations, and facilitates a thinner optic, than a comparable spherical surface.

Figure 42:
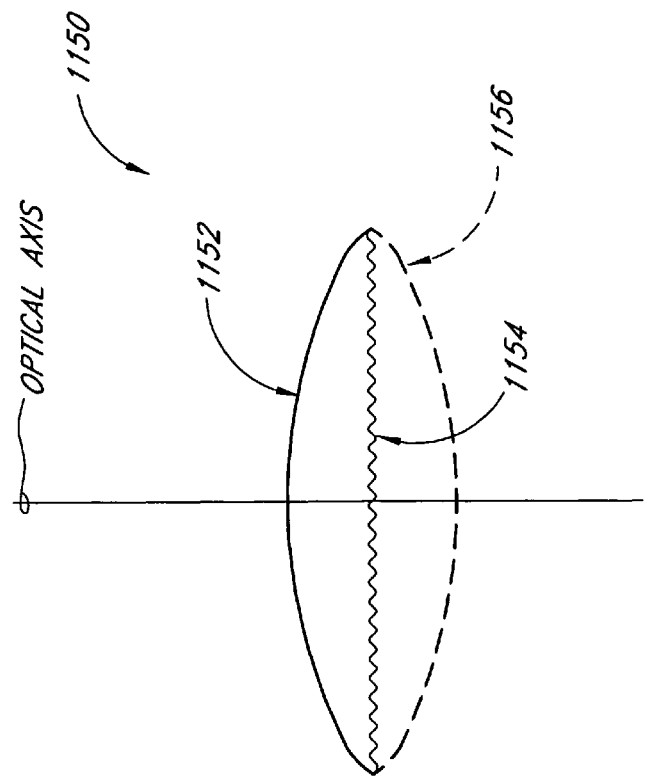
FIG. 42 is a sectional view of an optic having a diffractive surface for use with the lens system.

FIG. 42 depicts a further strategy for providing a thinner optic 1150. The optic 1150 has a curved (spherical or aspheric) optic surface 1152 and a flat or planar (or otherwise less curved than a comparable refractive surface) diffractive optic surface 1154 in place of a second curved surface 1156. The diffractive optic surface 1154 can comprise any suitable diffraction grating, including the grooved surface depicted or any other diffractive surface presently known or hereafter developed, including holographic optical elements. By appropriately configuring the diffractive surface 1154 as is well known in the art, the optic 1150 can be made thinner than one having both curved surfaces 1152, 1154, while providing the same focal power. The use of the diffractive surface 1154 not only facilitates a thinner optic, but also reduces aberrations in the resulting image.

A further alternative for facilitating a thin, easy-to-fold optic is to employ, in place of a biconvex optic of refractive index greater than aqueous humor (i.e., greater than about 1.336), a biconcave optic of refractive index less than about 1.336, which is thinner at the optical axis than the biconvex optic. By constructing the biconcave optic of material having a refractive index less than about 1.336, the biconcave optic can be made to have the same effective focal power, when immersed in aqueous humor, as a given biconvex optic.

Figure 43:
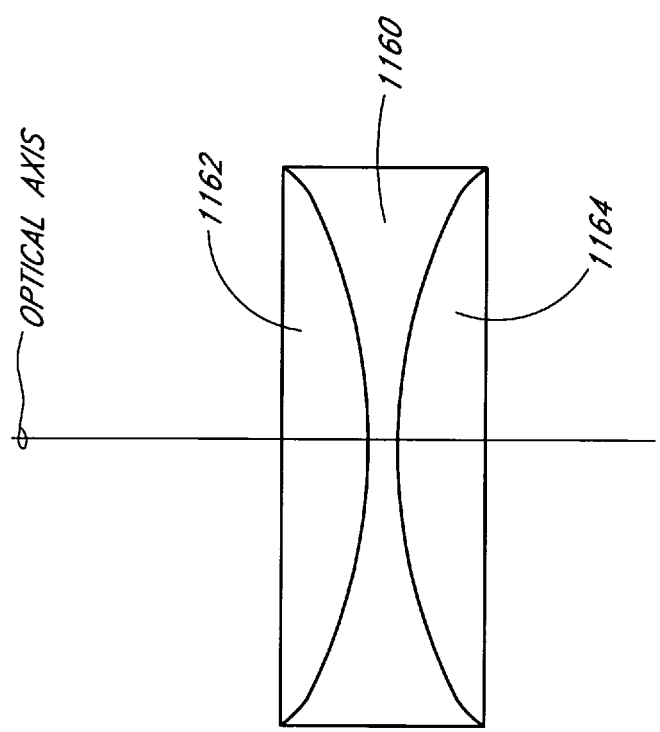
FIG. 43 is a sectional view of a low-index optic for use with the lens system.
Figure 44:
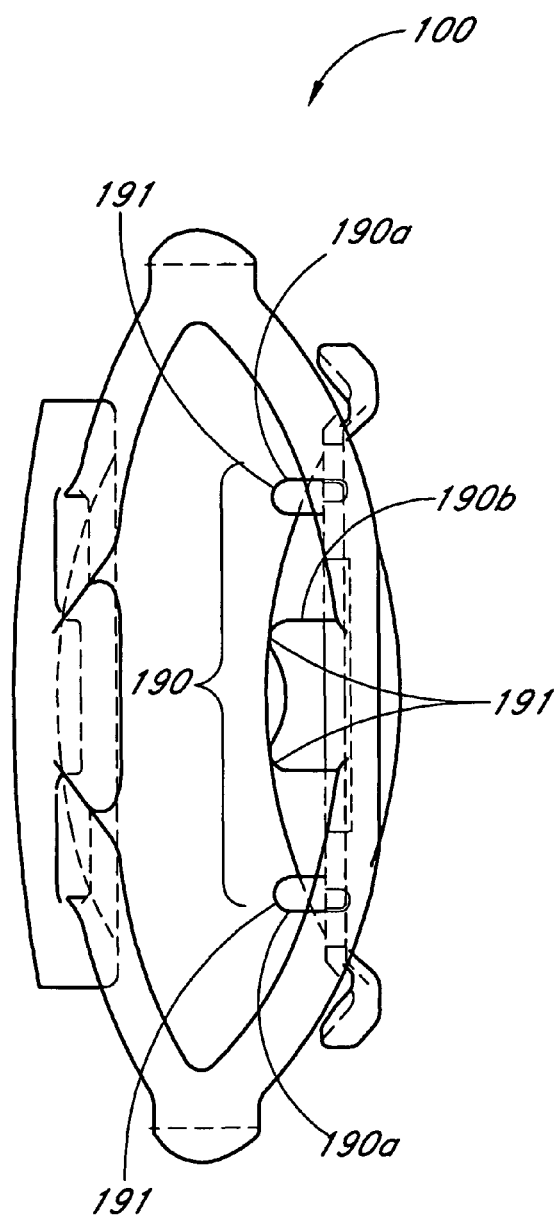
FIG. 44 is a side elevation view of another embodiment of the lens system with a number of separation members.
Figure 45:
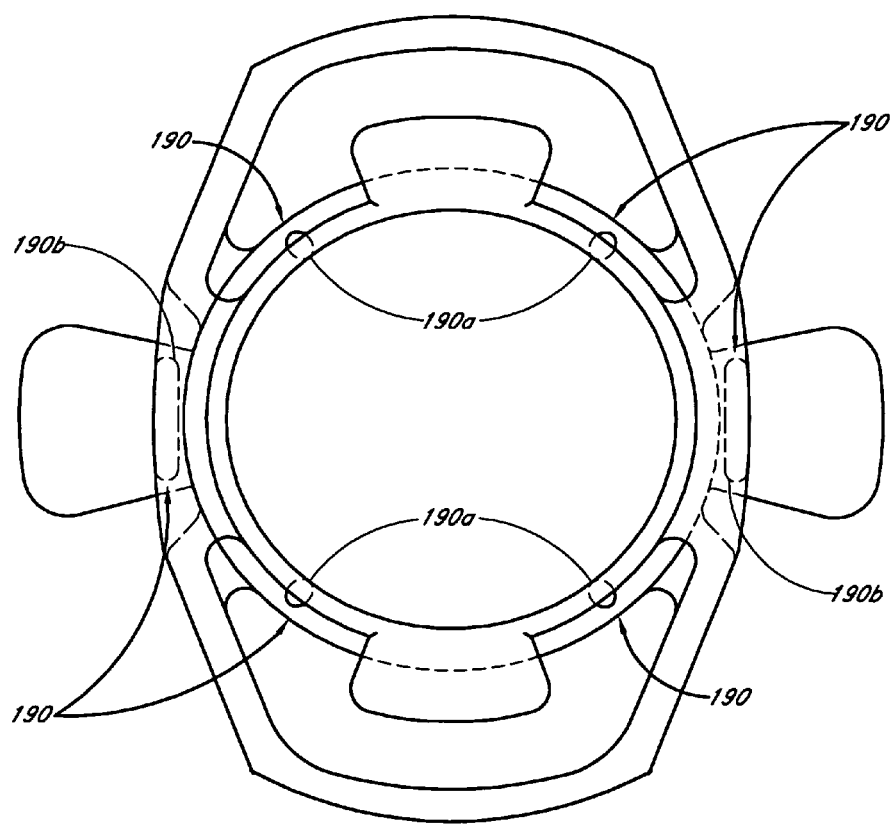
FIG. 45 is a front elevation view of the lens system of FIG. 44.
Figure 46:
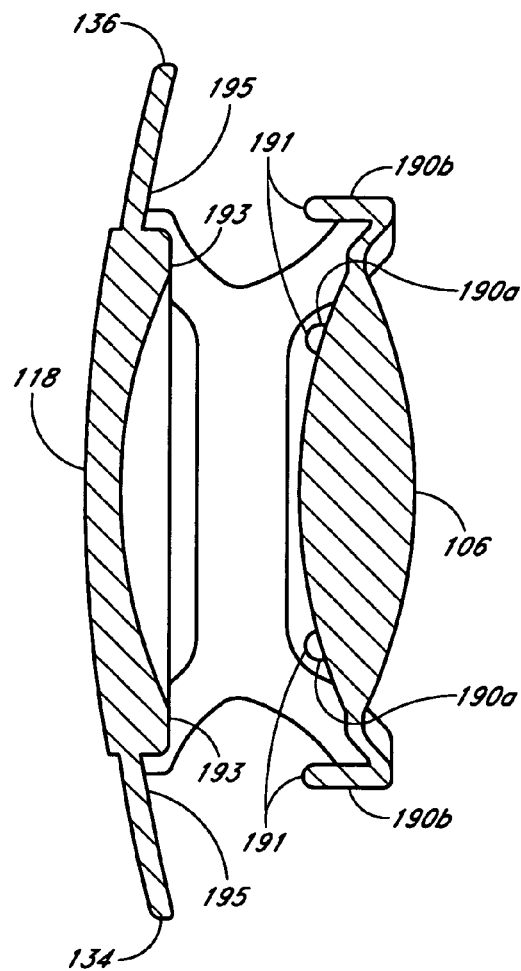
FIG. 46 is an overhead sectional view of the lens system of FIG. 44.
Figure 47:
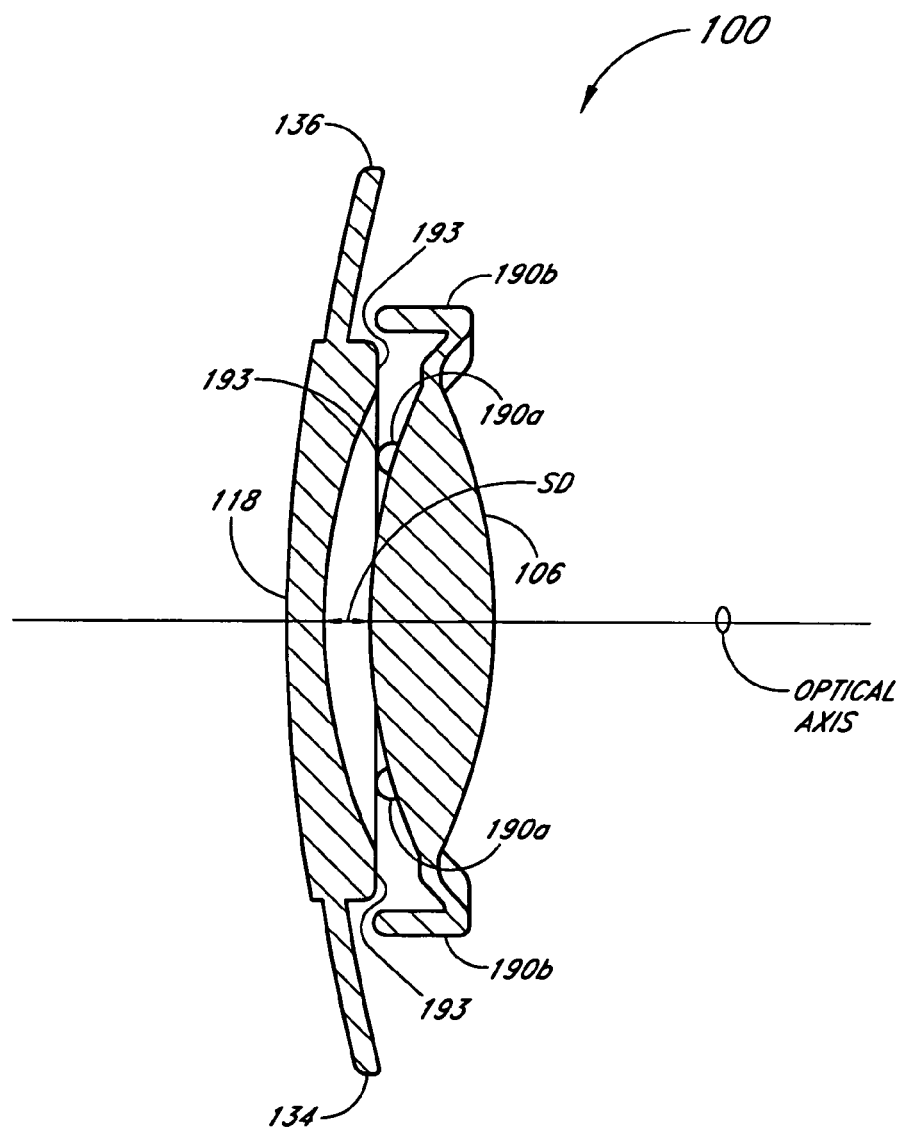
FIG. 47 is an overhead sectional view of the lens system of FIG. 44, with the viewing elements at a minimum separation distance.

Still another alternative thin optic, shown in FIG. 43, is a biconcave optic 1160 of low refractive index (for example, about 1.40 or less or about 1.336 or less) which is clad with first and second cladding portions 1162, 1164 constructed of higher-index material (for example, about 1.43 or greater). Such an optic can be made to have the same effective focal power, when immersed in aqueous humor, as a thicker biconvex optic.

As a further alternative, one or more of the surfaces of the optics may be formed as a multifocal surface, with spherical and/or aspheric focal regions. A multifocal surface can be made with less curvature than a comparable-power single-focus surface and thus allows the optic to be made thinner. The additional foci provide added power which replaces or exceeds the power that is "lost" when the surface is reduced in curvature. In one embodiment, the multifocal optic is constructed as a concentric-ring, refractive optic. In another embodiment, the multifocal optic is implemented as a diffractive multifocal optic.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An accommodating intraocular lens comprising an anterior viewing element, a posterior viewing element, first and second distending members joined to the posterior viewing element and not joined to the anterior viewing element, and a biasing structure, the anterior and posterior viewing elements having refractive power, the biasing structure defining a side opening in the accommodating intraocular lens, the opening extending by a distance greater than a diameter of at least one of the anterior and posterior viewing elements, the biasing structure being configured to move the viewing elements relative to each other along an optical axis between an accommodated state and an unaccommodated state in response to action of a ciliary muscle, the viewing elements being spaced farther apart in the accommodated state than in the unaccommodated state, the biasing structure being formed of silicone, at least one of the optics being formed of acrylic, the diameter extending transverse to and intersecting the optical axis of the lens, said distending members being substantially separate from the biasing structure, a first end of each of said distending members being fixed relative to the posterior viewing element, a second end of each of said distending members extending anteriorly of the posterior viewing element and radially outwardly away from the optical axis beyond a perimeter of the posterior viewing element.

2. The accommodating intraocular lens of claim 1, wherein said first and second distending members are arranged 180 degrees apart about the optical axis.

3. The accommodating intraocular lens of claim 1, wherein said first distending member further comprises an opening to permit cellular ingrowth by adjacent portions of a lens capsule.

4. The accommodating intraocular lens of claim 1, wherein an outermost portion of said first distending member is adapted to remain at a substantially constant distance from said optical axis as said viewing elements move relative to each other.

5. The accommodating intraocular lens of claim 1, wherein said biasing structure comprises an anterior biasing element and a posterior biasing element, said biasing elements being joined at first and second apices, said first and second apices being spaced from said optical axis of said lens, said first distending member is configured to distort a lens capsule such that the shape of the capsule is asymmetric about a plane perpendicular to the optical axis and passing through said apices.

6. The accommodating intraocular lens of claim 1, wherein said biasing structure comprises an anterior biasing element and a posterior biasing element, said biasing elements being joined at first and second apices, said first and second apices being spaced from said optical axis of said lens, and said first and second distending members being located angularly midway between said apices about said optical axis of said lens.

7. The accommodating intraocular lens of claim 1, wherein said biasing structure comprises an anterior biasing element and a posterior biasing element, said biasing elements being joined at first and second apices, said apices being intersected by a transverse plane of said lens, said second end of said each distending member being closer to the transverse plane, as measured along a direction generally parallel to the optical axis of the lens while said lens is viewed from the side, when said viewing elements are in said unaccommodated state, than when said viewing elements are in said accommodated state.

8. An accommodating intraocular lens comprising a first optic, a second optic, first and second distending members joined to the first optic and not joined to the second optic, and a biasing structure, the lens comprising silicone, the optics being formed of an optic material having an index of refraction higher than that of said silicone, the biasing structure defining a side opening in the accommodating intraocular lens, the side opening extending by a distance greater than a diameter of at least one of the first and second optics, wherein said intraocular lens is biased toward an accommodated state, the diameter extending transverse to and intersecting an optical axis of the lens, said distending members being substantially separate from the biasing structure, a first end of each of said distending members being fixed relative to the first optic, a second end of each of said distending members extending anteriorly of the first optic and radially outwardly away from the optical axis of the accommodating intraocular lens beyond a perimeter of the first optic.

9. The accommodating intraocular lens of claim 8, wherein said first and second distending members are arranged 180 degrees apart about the optical axis of said lens.

10. The accommodating intraocular lens of claim 8, wherein said first distending member further comprises an opening to permit cellular ingrowth by adjacent portions of a lens capsule.

11. The accommodating intraocular lens of claim 8, wherein an outermost portion of said first distending member is adapted to remain at a substantially constant distance from said optical axis of said lens as said optics move relative to each other.

12. The accommodating intraocular lens of claim 8, wherein said biasing structure comprises an anterior biasing element and a posterior biasing element, said biasing elements being joined at first and second apices, said first and second apices being spaced from said optical axis of said lens, said first distending member is configured to distort a lens capsule such that the shape of the capsule is asymmetric about a plane perpendicular to the optical axis of said lens and passing through said apices.

13. The accommodating intraocular lens of claim 8, wherein said biasing structure comprises an anterior biasing element and a posterior biasing element, said biasing elements being joined at first and second apices, said first and second apices being spaced from said optical axis of lens, and said first and second distending members being located angularly midway between said apices about the optical axis of said lens.

14. The accommodating intraocular lens of claim 8, wherein said biasing structure comprises an anterior biasing element and a posterior biasing element, said biasing elements being joined at first and second apices, said apices being intersected by a transverse plane of said lens, said second end of said each distending member being closer to the transverse plane, as measured along a direction generally parallel to optical axis of said lens while said lens is viewed from the side, when said optics are in said unaccommodated state, than when said optics are in said accommodated state.

15. An accommodating intraocular lens having an optical axis, comprising:
an anterior optic having positive refractive power and a posterior optic having negative refractive power, said posterior optic configured to engage a capsular bag of an eye upon implantation therein;
an anterior biasing element and a posterior biasing element;
first and second distending members joined to the posterior optic and not joined to the anterior optic, said distending members being substantially separate from the anterior and posterior biasing elements, a first end of each of said distending members being fixed relative to the posterior optic, a second end of each of said distending members extending radially outwardly away from an optical axis beyond a perimeter of the posterior optic;
wherein the anterior biasing element and the posterior biasing element are joined at first and second apices which are spaced radially from said optical axis, and wherein at least respective portions of the anterior and posterior optics are disposed on opposite sides of a line passing through the first and second apices;
wherein the optics comprise an optic material having an index of refraction of about 1.49; and
wherein the lens comprises silicone.

16. The accommodating intraocular lens of claim 15, wherein said first and second distending members are arranged 180 degrees apart about optical axis of said lens.

17. The accommodating intraocular lens of claim 15, wherein said first distending member further comprises an opening to permit cellular ingrowth by adjacent portions of the capsular bag.

18. The accommodating intraocular lens of claim 15, wherein an outermost portion of said first distending member is adapted to remain at a substantially constant distance from said optical axis of said lens as said optics move relative to each other.

19. The accommodating intraocular lens of claim 15, wherein said biasing elements are joined at said first and second apices, said first distending member is configured to distort the capsular bag such that the shape of the capsular bag is asymmetric about a plane perpendicular to the optical axis of said lens and passing through said apices.

20. The accommodating intraocular lens of claim 15, wherein said biasing elements are joined at said first and second apices, said first and second apices being spaced from said optical axis of said lens, and said first and second distending members being located angularly midway between said apices about said optical axis of said lens.

21. The accommodating intraocular lens of claim 15, wherein said biasing elements are joined at said first and second apices, said apices being intersected by a transverse plane of said lens, said second end of said each distending member being closer to the transverse plane, as measured along a direction generally parallel to the optical axis of the lens while said lens is viewed from the side, when said optics are in said unaccommodated state, than when said optics are in said accommodated state.

* * * * *